United States Patent
Zhang et al.

(10) Patent No.: US 11,834,432 B2
(45) Date of Patent: Dec. 5, 2023

(54) SUBSTITUTED AMINO SIX-MEMBERED NITRIC HETEROCYCLIC RING COMPOUND AND PREPARATION AND USE THEREOF

(71) Applicant: SHANGHAI INSTITUTE OF MATERIA MEDICA, CHINESE ACADEMY OF SCIENCES, Shanghai (CN)

(72) Inventors: Ao Zhang, Shanghai (CN); Meiyu Geng, Shanghai (CN); Li Xing, Shanghai (CN); Jing Ai, Shanghai (CN); Zilan Song, Shanghai (CN); Xia Peng, Shanghai (CN); Wangting Gu, Shanghai (CN); Jian Ding, Shanghai (CN)

(73) Assignee: SHANGHAI INSTITUTE OF MATERIA MEDICA, CHINESE ACADEMY OF SCIENCES, Shanghai (CN)

(*) Notice: Subject to any disclaimer, the term of this patent is extended or adjusted under 35 U.S.C. 154(b) by 0 days.

(21) Appl. No.: 15/998,927

(22) PCT Filed: Feb. 17, 2017

(86) PCT No.: PCT/CN2017/073966
§ 371 (c)(1),
(2) Date: Oct. 9, 2018

(87) PCT Pub. No.: WO2017/140269
PCT Pub. Date: Aug. 24, 2017

(65) Prior Publication Data
US 2020/0172510 A1   Jun. 4, 2020

(30) Foreign Application Priority Data

Feb. 19, 2016  (CN) .......................... 201610094401.7

(51) Int. Cl.
| | | |
|---|---|---|
| *C07D 213/75* | (2006.01) | |
| *C07D 401/12* | (2006.01) | |
| *C07D 403/12* | (2006.01) | |
| *C07D 405/12* | (2006.01) | |
| *C07D 413/12* | (2006.01) | |
| *C07D 413/14* | (2006.01) | |
| *C07D 417/12* | (2006.01) | |
| *C07D 417/14* | (2006.01) | |
| *A61P 35/00* | (2006.01) | |
| *A61K 31/4427* | (2006.01) | |
| *A61K 31/4439* | (2006.01) | |

(Continued)

(52) U.S. Cl.
CPC ............ *C07D 401/12* (2013.01); *A61P 35/00* (2018.01); *C07D 213/75* (2013.01); *C07D 403/12* (2013.01); *C07D 405/12* (2013.01); *C07D 413/14* (2013.01); *C07D 417/14* (2013.01)

(58) Field of Classification Search
CPC .. C07D 401/12; C07D 403/12; C07D 413/14; C07D 405/12; C07D 417/14; C07D 213/75; C07D 413/12; C07D 417/12; A61P 35/00; A61K 31/4427; A61K 31/4439; A61K 31/444; A61K 31/4433; A61K 31/4409; A61K 31/496; A61K 31/506; A61K 31/5355; A61K 31/5377; A61K 31/4545; A61K 31/44
See application file for complete search history.

(56) References Cited

U.S. PATENT DOCUMENTS

2010/0004438 A1* 1/2010 Matsuyama ......... A61K 31/496
540/575

FOREIGN PATENT DOCUMENTS

| CN | 101687801 | * | 4/2008 |
| CN | 101365682 A | | 2/2009 |

(Continued)

OTHER PUBLICATIONS

Int'l Search Report dated May 24, 2017 in Int'l Application No. PCT/CN2017/073966.

*Primary Examiner* — Brenda L Coleman
(74) *Attorney, Agent, or Firm* — Panitch Schwarze Belisario & Nadel LLP

(57) ABSTRACT

Provided in the present invention are a substituted amino six-membered nitric heterocyclic ring compound and a preparation and use thereof. In particular, provided in the present invention is a compound as shown by general formula (I) below, wherein the definition of each group is as described in the description. The compound of the present invention has an excellent tyrosine kinase inhibitory activity, and can thus be used to prepare a series of medicines for treating diseases related to tyrosine kinase inhibitory activity.

Formula I

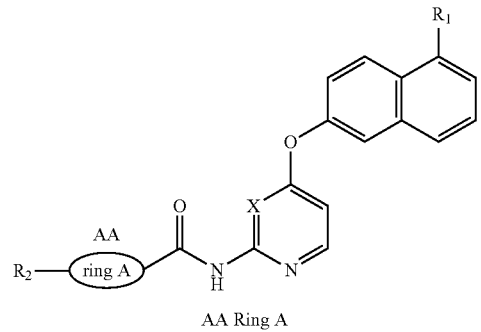

AA Ring A

16 Claims, 1 Drawing Sheet

(51) Int. Cl.
*A61K 31/444* (2006.01)
*A61K 31/4433* (2006.01)
*A61K 31/4409* (2006.01)
*A61K 31/496* (2006.01)
*A61K 31/506* (2006.01)
*A61K 31/5355* (2006.01)
*A61K 31/5377* (2006.01)
*A61K 31/4545* (2006.01)
*A61K 31/44* (2006.01)

(56) References Cited

FOREIGN PATENT DOCUMENTS

| | | |
|---|---|---|
| CN | 101687801 A | 3/2010 |
| WO | 2012040137 A1 | 3/2012 |

\* cited by examiner

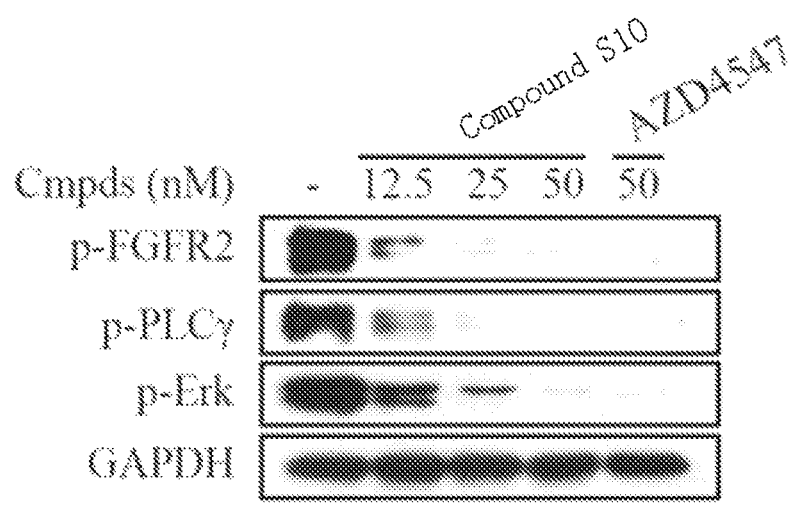

SUBSTITUTED AMINO SIX-MEMBERED NITRIC HETEROCYCLIC RING COMPOUND AND PREPARATION AND USE THEREOF

CROSS-REFERENCE TO RELATED APPLICATION

This application is a Section 371 of International Application No. PCT/CN2017/073966, filed Feb. 17, 2017, which was published in the Chinese language on Aug. 24, 2017, under International Publication No. WO 2017/140269 A1, which claims priority under 35 U.S.C. § 119(b) to Chinese Application No. 201610094401.7, filed Feb. 19, 2016, the disclosures of which are incorporated herein by reference in their entirety.

FIELD OF THE INVENTION

The present invention relates to a substituted aminopyridine compound having tyrosine kinase selective inhibitory activity, and pharmaceutically acceptable salt or solvent, and the preparation process thereof, and the use in the preparation of medicine for preventing or treating fibroblast growth factor receptor-associated diseases such as abnormal proliferation, morphological changes of cells, and hyperkinesia, as well as diseases associated with angiogenesis or cancer metastasis, especially for the preparation of medicine for treatment or prevention of tumor growth and metastasis.

BACKGROUND OF THE INVENTION

Fibroblast growth factor receptors (FGFRs) are receptor tyrosine kinases, family members of which include FGFR1, FGFR2, FGFR3, and FGFR4. Their basic structures include extracellular domain, transmembrane region, and tyrosine kinase domain. The extracellular domain is consisted of three immunoglobulin-like domains, including an acidic structural framework, a membrane domain, and a cleavage intracellular tyrosine kinase domain. Like other tyrosine kinases, when the ligand binds to FGFR, the receptor dimerizes, and the formed ternary (FGF-FGFR-HPSG) complex dimerizes to make the structure of the FGFR change, thus causing transfer of intramolecular phosphorylation of the intracellular tyrosine kinase domain and the terminal carboxylic acid moiety, followed by attachment of the FGFR receptor substrate (FRS2α) and phospholipase C (PLCγ) to activate a series of downstream signaling pathways, such as Ras/mitogen-activated protein kinase (MAPK) pathway and phosphoinositide kinase 3 (PI3K)/Akt pathway, which in turn stimulates some physiological processes in the cell, such as cell proliferation, survival, migration and angiogenesis.

FGFR activation is closely related to the occurrence, development and resistance of various tumors. FGFRs participate in tumorigenesis mainly through three mechanisms: chromosomal transtocation, gene mutation, gene amplification or overexpression. The chromosomal translocation of FGFR1 gene or its fusion gene is mainly present in multiple myeloma; both of FGFR2 and FGFR3 mutations are expressed in lung squamous cell carcinoma, and FGFR4 Y367C mutation in transmembrane region enables continuous activation of breast cancer cells. It is reported that FGFR amplification occurs in a variety of different cancers, FGFR1 amplification occurs in patients with rectal cancer, lung cancer and kidney cancer, in addition, in about 10% of breast cancer, especially estrogen receptor-positive patients, FGFR1 8p11-12 site is amplified, while gastric cancer and rectal cancer patients also showed amplification of FGFR2, FGFR3 amplification is most common in patients with bladder cancer. Therefore, studies of inhibitors targeting FGFR kinase are of great importance in the treatment of malignant tumors.

In recent years, the development of small molecule tyrosine kinase inhibitors (TKI), therapeutic target of which is FGFRs, has become a hot spot in anti-tumor drug research. Some FGFR inhibitors have entered the clinical research stage and can be classified as selective FGFR inhibitors or non-selective FGFR inhibitors depending on their range of action. These inhibitors mainly inhibit FGFR activation by targeting the FGFR intracellular kinase domain ATP binding site, and can be applied to tumor types of FGFRs overexpression, FGFRs mutations or expression of FGFR-fusion proteins. AZD4547, BGJ398, LY2874455 and AL-3810 are all selective FGFR inhibitors that have entered clinic and have strong anti-tumor activity. As reported in the literature, AZD-4547, BGJ-398, and AL-3810 are potent inhibitors of FGFR1-3, while LY2874455 is a pan-FGFR inhibitor (acting on FGFR1-4).

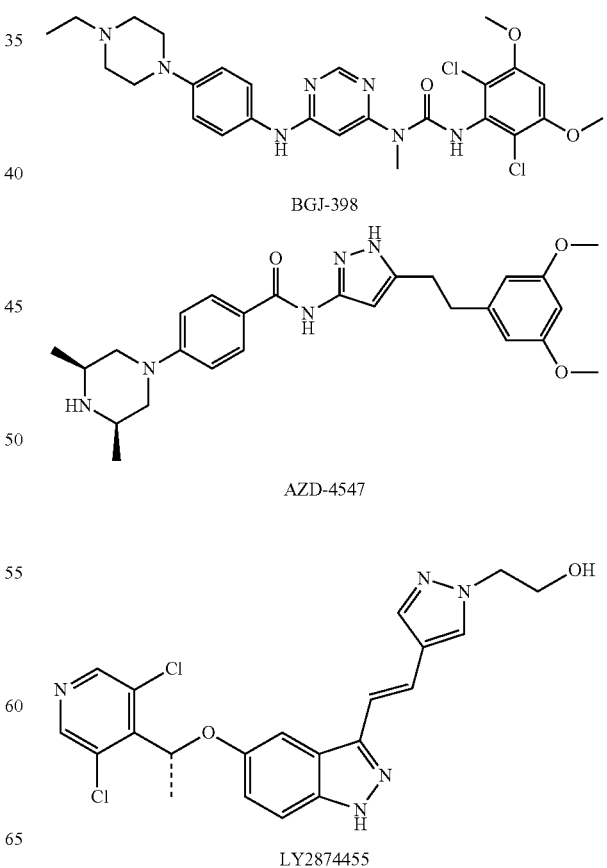

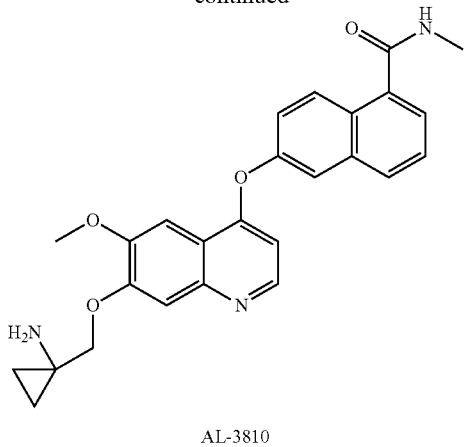

AL-3810

Due to the highly similar structure of PDGFRs, VEGFRs and FGFRs, most FGFR TKIs have inhibitiory activity on PDGFR as well as VEGFR, causing large toxic side effects of FGFR inhibitors. The development of FGFR inhibitors still faces great challenges. In terms of structure, the structure of FGFR inhibitors is very limited.

In summary, there is a need in the art to develop FGFR inhibitors having novel structures.

SUMMARY OF THE INVENTION

The object of the present invention is to provide a novel class of FGFR kinase inhibitors which are structurally novel and have excellent activity.

In the first aspect of the present invention, a compound of the following formula I, or a pharmaceutically acceptable salt thereof is provided:

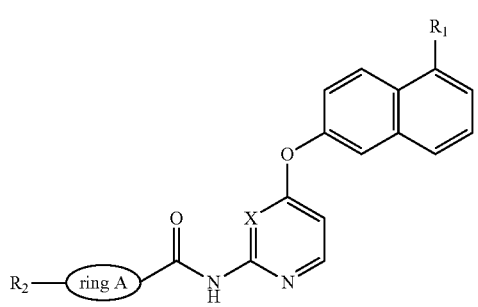

Formula I wherein:
X is selected from the group consisting of CH and N;
Ring A may be selected from the group consisting of a substituted or unsubstituted 6-10 membered aryl, substituted and unsubstituted 5-12 membered heteroaryl, wherein "substituted" means that one or more hydrogen atoms on a group are substituted by substituents selected from the group consisting of a C1-C8 alkyl, C1-C8 alkoxy, C1-C8 alkylamino, halogen, halogenated C1-C8 alkyl;
$R_1$ is selected from —CONHR$_3$ or —COOR$_3$;
$R_2$ is selected from the group consisting of a substituted or unsubstituted C1-C8 alkyl, substituted or unsubstituted C1-C8 alkoxy, substituted or unsubstituted 4-10 membered heterocyclic group, substituted or unsubstituted amino, substituted or unsubstituted C1-C8 alkylamino group, —NH-COR$_3$; wherein the substituent group is further substituted by one or more substituents selected from the group consisting of a C1-C8 alkyl, hydroxy, hydroxy C1-C8 alkyl, —COOR$_3$, amino-substituted C3-C10 cycloalkyl group, 4-10 membered heterocycloalkyl group which is unsubstituted or substituted by one or more halogen atoms, hydroxyl or C1-C8 alkyl;
$R_3$ is selected from hydrogen, C1-C8 alkyl, C2-C10 alkenyl.

In another preferred embodiment, in the compound I, ring A is selected from a substituted or unsubstituted 6-10 membered aryl, substituted or unsubstituted 5-10 membered heteroaryl.

In another preferred embodiment, in the compound I, ring A is selected from a substituted or unsubstituted 6-10 membered aryl, substituted or unsubstituted 5-6 membered heteroaryl.

In another preferred embodiment, in the compound I, ring A is a substituted or unsubstituted group selected from the group consisting of a benzene ring, naphthalene ring, pyridine ring, pyrazine ring, thiophene ring, furan ring, imidazole ring, pyrrole ring, oxazole ring, thiazole ring, pyrazole ring, indole ring, pyrimidine ring, benzofuran ring, benzo thiazole ring, benzimidazole ring, quinoline ring, isnquinoline ring;

In another preferred embodiment, in the compound I, ring A is selected from the group consisting of a substituted or unsubstituted benzene ring, substituted or unsubstituted thiazole ring, substituted or unsubstituted oxazole ring, substituted or unsubstituted pyrimidine ring.

In another preferred embodiment, in the formula I compound, $R_2$ is selected from the group consisting of a substituted or unsubstituted C1-C4 alkyl, substituted or unsubstituted C1-C4 alkoxy, substituted or unsubstituted 5-6 membered heterocyclic group, substituted or unsubstituted amino, substituted or unsubstituted C1-C4 alkylamino group, —NHCOR$_3$; wherein "substituted" means that the group is further substituted by one or more substituents selected from the group consisting of a C1-C8 alkyl, hydroxy, hydroxy C1-C8 alkyl, —COOR$_3$, amino-substituted C3-C10 cycloalkyl, 4-10 membered heterocycloalkyl which is unsubstituted or substituted by one or more halogen atoms, hydroxyl or C1-C8 alkyl.

In another preferred embodiment, in the formula I compound, $R_3$ is selected from hydrogen, C1-C6 alkyl, C2-C6 alkenyl.

In another preferred embodiment, in the formula I compound, $R_3$ is selected from hydrogen, C1-C4 alkyl, C2-C4 alkenyl.

In another preferred embodiment, in the formula I compound, $R_3$ is selected from hydrogen, methyl, ethenyl.

In another preferred embodiment, the compound is selected from the group consisting of: compound S1, S2, S3, S4, S5, S6, S7, S8, S9, S10, S11, S12, S13, S14, S15, S16, S17, S18, S19, S20, S21, S22, S23 and S24.

In the second aspect of the present invention, the preparation method of compound of the first aspect of the present invention is provided, which comprises the following steps:

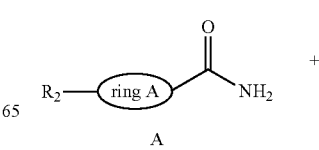

A

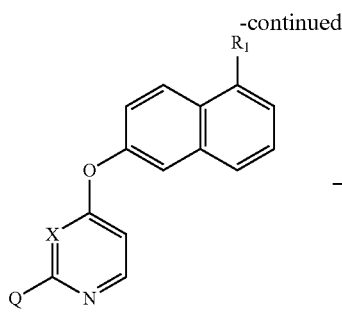

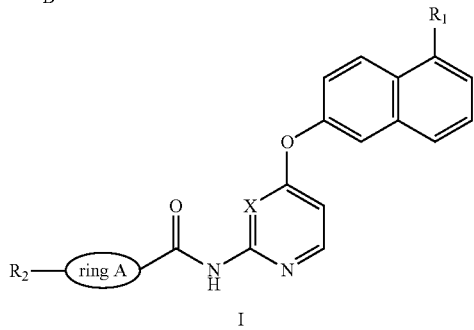

In an inert solvent, formula A compound reacts with formula B compound to obtain formula I compound;

wherein Q is a leaving group, preferably halogen; ring A, X, R1 and R2 are defined as in the first aspect of the invention.

In another preferred embodiment, the reaction is conducted in the presence of $Pd_2(dba)_3$ [Tris(dibenzylideneacetone)dipalladium], Xantphos[9,9-Dimethyl-4,5-bis(diphenylphosphino)xanthenes], or cesium carbonate.

In another preferred embodiment, the reaction comprises: dissolving the compound A, compound B (1.0-1.5 eq), $Pd_2(dba)_3$ [Tris(dibenzylideneacetone)dipalladium] (0.05-0.2 eq), Xantphos[9,9-Dimethyl-4,5-bis(diphenylphosphino)xanthenes] (0.1-0.5 eq) and cesium carbonate (1-3 eq) in an inert solvent, and reacting under protection of nitrogen In another preferred embodiment, the inert solvent is 1,4-dioxane.

In another preferred embodiment, the reaction is carried out at 100° C.

In another preferred embodiment, the reaction time of the process is 1-10 h.

In another preferred embodiment, after the reaction is completed, dichloromethane and water are used for extraction, and the organic phase is washed with saturated brine and dried over anhydrous sodium sulfate, and then the mixed sample is purified through column to give the compound.

In the third aspect of the present invention, a pharmaceutical composition is provided, comprising: a therapeutically effective amount of the compound of the first aspect of the present invention, or a pharmaceutically acceptable salt, prodrug, hydrate or solvate thereof, and optionally a pharmaceutically acceptable carrier or excipient.

In another preferred embodiment, the pharmaceutical composition is a pharmaceutical composition for treating a tumor, or a pharmaceutical composition for treating a disease associated with tyrosine kinase (preferably FGFR, more preferably FGFR1) activity.

In another preferred embodiment, the pharmaceutical composition is used to treat diseases associated with abnormal expression of FGF/FGFR signaling pathway.

In the fourth aspect of the present invention, the use of compound of the first aspect of the invention, or a pharmaceutically acceptable salt, prodrug, hydrate or solvate thereof is provided, for the preparation of medicine for the prevention and/or treatment of FGFR related diseases.

In another preferred embodiment, the tumor-related disease is selected from the group consisting of breast cancer, lung cancer, bladder cancer, gastric cancer, pancreatic cancer, prostate cancer, colon cancer, myeloma, liver cancer, melanoma, head and neck cancer, thyroid cancer, renal cell carcinoma, glioblastoma, and testicular cancer; preferably breast cancer, non-small cell lung cancer, bladder cancer, stomach cancer, pancreatic cancer, prostate cancer, colon cancer, multiple myeloma, liver cancer, melanoma, head and neck cancer, thyroid cancer, renal cell carcinoma, glioblastoma, and testicular cancer; more preferably non-small cell lung cancer, gastric cancer, multiple myeloma.

In the fifth aspect of the present invention, a protein tyrosine kinase enzyme activity inhibitor is provided, comprising an inhibitory effective amount of the compound according to the first aspect of the invention, or a pharmaceutically acceptable salt, prodrug, hydrate or solvent thereof.

In the sixth aspect of the present invention, a pharmaceutical composition for treating diseases associated with cancer or protein tyrosine kinase activity is provided, wherein the pharmaceutical composition comprises a therapeutically effective amount of a compound according to the first aspect of the invention, or a pharmaceutically acceptable salt, prodrug, hydrate or solvent thereof as an active ingredient.

In the seventh aspect of the present invention, a method for treating or preventing cancer or a disease associated with protein tyrosine kinase activity is provided, comprising: administering a therapeutically or prophylactically effective amount of compound according to the first aspect of the invention, or a pharmaceutically acceptable salt, prodrug, hydrate or solvate thereof, or a pharmaceutical composition according to the invention to a subject to be treated or prevented.

It should be understood that, in the present invention, each of the technical features specifically described above and below (such as those in the Examples) can be combined with each other, thereby constituting new or preferred technical solutions which need not be specified again herein.

DESCRIPTION OF THE DRAWINGS

The FIGURE shows inhibition result on FGFR2 and phosphorylation of downstream signaling molecules in SNU16 gastric cancer cell strain by S10.

EMBODIMENTS FOR CARRYING OUT THE INVENTION

After long-term and intensive research, the present inventors have unexpectedly discovered that a compound with a novel structure and aminopyridine core can be obtained by replacing a quinoline in the framework of the literature-reported FGFR inhibitor AL-3810 with an aminopyridine. On the above basis, a new class of aminopyridine derivatives with better FGFR inhibitory activity and metabolic properties can be obtained by introducing aromatic rings substituted with different water-soluble groups. The present invention is completed on this basis.

Terms

As used herein, the term "heterocyclic group" is a cyclic group having 1, 2, 3, 4 or 5 heteroatoms selected from the group consisting of O, N and S.

Herein, the alkyl group is preferably an aliphatic alkyl group, and may be a linear alkyl group, a branched alkyl group, a spirocycloalkyl group, a bridged cycloalkyl group, an olefin alkyl group, an alkyne group, a cycloalkyl group, cycloalkenyl, cycloalkynyl, alkoxyalkyl, alkoxyalkyl, cycloalkylalkyl, including without limitation: methyl, ethyl, n-propyl, isopropyl, n-butyl, iso-butyl, tert-butyl, cyclopropyl, cyclobutane, cyclopentyl, cyclohexane, allyl, propargyl, cyclobutenyl, cyclohexenyl. An expression of "C1-C8" is intended to include a corresponding group having 1, 2, 3, 4, 5, 6, 7 or 8 carbon atoms, for example, "C1-C8 alkyl" means an alkyl group having 1, 2, 3, 4, 5, 6, 7 or 8 carbon atoms, "C2-C10 alkenyl" means an alkenyl group having 2, 3, 4, 5, 6, 7, 8, 9 or 10 carbon atoms.

Herein, the alkenyl group is preferably vinyl group, propenyl group, butenyl group, styryl group, phenylpropenyl group, or the like.

Herein, the cycloalkyl group may be saturated or partially unsaturated monocyclic or polycyclic cyclic hydrocarbon substituent including 3 to 20 carbon atoms, preferably including 3 to 12 carbon atoms, more preferably, a cycloalkyl group including 3 to 10 carbon atoms. Non-limiting examples of monocyclic cycloalkyl groups include cyclopropyl, cyclobutyl, cyclopentenyl, cyclohexyl, cyclooctyl and the like; and polycyclic cycloalkyl groups Include spiro, fused or bridged cycloalkyl.

The heterocyclic group refers to a saturated or partially saturated monocyclic or polycyclic cyclic substituent including 4- to 10-membered heterocyclic group, and the heterocyclic group is a saturated or unsaturated monocyclic ring, paracyclic ring, spiro ring, fused ring, bridged ring which comprises one or more hetero atoms (nitrogen, oxygen or sulfur), or the like. The heterocyclic group described herein includes, but is not limited to, a group selected from the group consisting of morpholine ring, piperidine ring, piperazine ring, N-alkyl or acyl substituted piperazine ring, homopiperazine ring, N-alkyl or acyl substituted homopiperazine ring, pyrrole, tetrahydropyrrole, 7H-purine, and the like.

The aryl group refers to a 6 to 10 membered per-carbon monocyclic or fused polycyclic ring (that is, a ring sharing a pair of adjacent carbon atoms), and the group has a conjugated n-electron system, such as phenyl group or naphthyl. The aryl ring may be fused to a heterocyclyl, heteroaryl or cycloalkyl ring, non-limiting examples including benzimidazole, benzothiazole, benzoxazole, benzisoxazole, benzopyrazol, quinoline, benzoindoles, benzodihydrofuran.

The heteroaryl group refers to a heteroaromatic system comprising 1 to 4 heteroatoms and 5 to 14 ring atoms, wherein the heteroatoms include oxygen, sulfur and nitrogen. The heteroaryl group is preferably 5- or 6-membered, such as furyl, thienyl, pyridyl, pyrrolyl, N-alkylpyrrolyl, pyrimidinyl, pyrazinyl, imidazolyl, tetrazolyl, and the like. The heteroaryl group can be fused to aryl group, heterocyclic group or cycloalkyl ring, wherein the ring to which the parent structure is attached is a heteroaryl ring.

Unless otherwise stated, the structural formula described herein is intended to include all tautomeric, optical, and stereoisomeric forms (e.g., enantiomers, diastereomers, geometric isomers or conformations), for example, R, S configurations containing asymmetric centers, (Z), (E) isomers of double bonds, and conformers of (Z), (E). Therefore, a single stereochemical isomer, tautomer or enantiomer, diastereomer or geometric isomer or conformers or mixture of tautomers of the compounds of the invention all fall within the scope of the invention.

The term "tautomer" means that structural isomers having different energies can exceed the low energy barrier, thereby transforming between each other. For example, proton tautomers (i.e., proton shifts) include interconversions by proton transfer, such as 1H-carbazole and 2H-carbazole, 1H-benzo[d]imidazole and 3H-benzo[d]imidazole. The valence tautomers include interconversion through some bonding electron recombination.

Herein, a pharmaceutically acceptable salt is not particularly limited, preferably include: inorganic acid salts, organic acid salts, alkyl sulfonates, and arylsulphonates; the inorganic acid salts include hydrochlorides, hydrobromides, nitrates, sulfates, phosphates, etc.; the organic acid salts include formates, acetates, propionates, benzoates, maleates, fumarates, succinates, tartrates, citrates, etc.; the alkyl sulfonates include methyl sulfonates, ethyl sulfonates, etc.; the aryl sulfonates include benzene sulfonates, p-toluene sulfonates, and the like.

Herein, a pharmaceutically acceptable solvate of the compound represented by the general formula (I) is not particularly limited, and preferably includes a solvate of a compound represented by the general formula (I) with solvents such as water, ethanol, isopropanol, diethyl ether, acetone.

Compound of Formula (I)

The inventors has designed and synthesized a series of novel compounds by studying the structure-activity relationship between the crystal structure of FGFR and other tyrosine kinase inhibitors. After screening these compounds by molecular, cellular and animal models, it is found that the compounds can significantly inhibit FGFR kinase activity at molecular level. Also, it can significantly inhibit FGFR-induced proliferation of various cancer cells at cell level, and can significantly inhibit tumor growth in animals.

In particular, the invention provides a compound of formula I, or a pharmaceutically acceptable salt thereof:

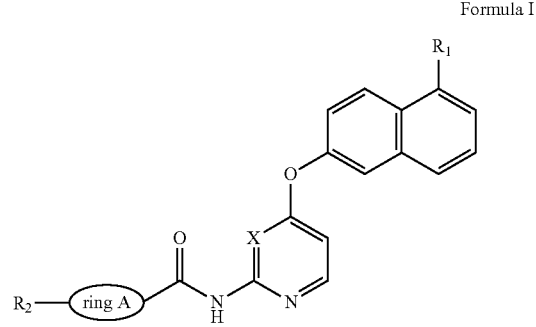

Formula I

In another preferred embodiment, in the compound, any one of X, ring A, $R_1$, $R_2$, and $R_3$ is a corresponding group in the specific compound described in the examples.

Preferably, the aminopyridine compound of the formula (I) of the present invention is selected from the compounds of Table I below:

TABLE 1
| Compound | Structure |
| --- | --- |
| S1 | 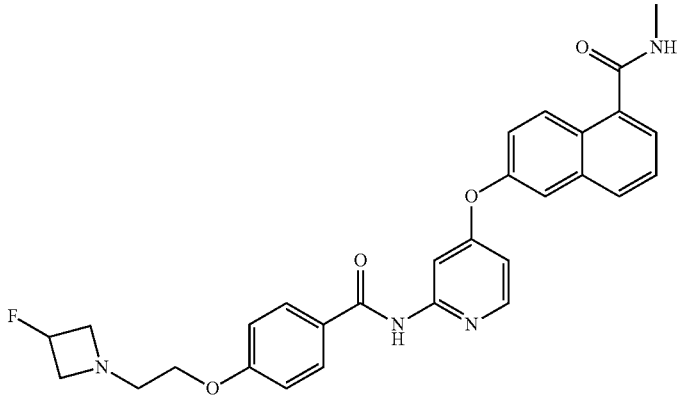 [SMILES: CNC(=O)c1cccc2cc(Oc3ccnc(NC(=O)c4ccc(OCCN5CC(F)C5)cc4)c3)ccc12] |
| S2 | 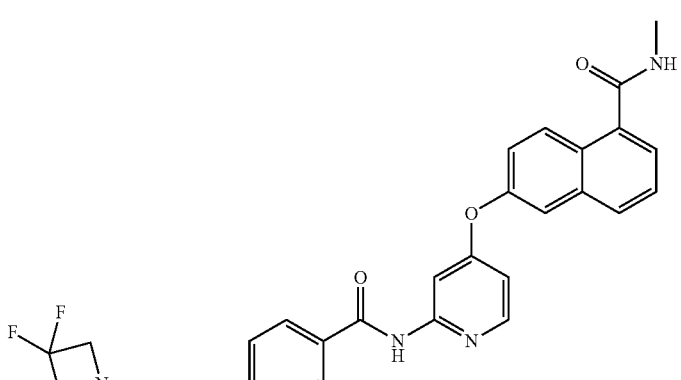 |
| S3 | 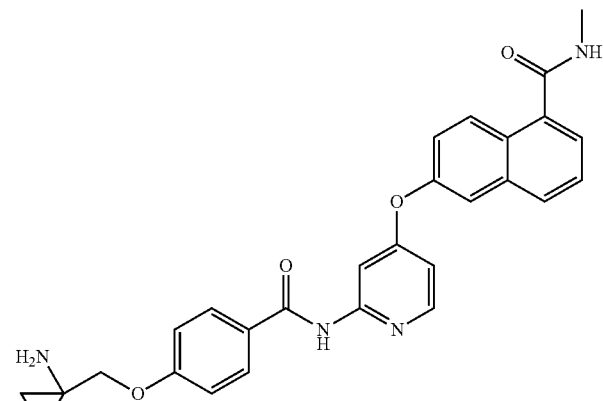 |

TABLE 1-continued

| Compound | Structure |
|---|---|
| S4 | 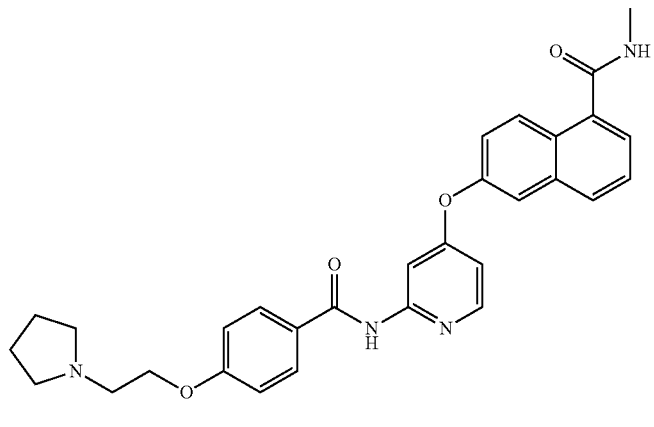 [SMILES: CNC(=O)c1cccc2cc(Oc3ccnc(NC(=O)c4ccc(OCCN5CCCC5)cc4)c3)ccc12] |
| S5 | 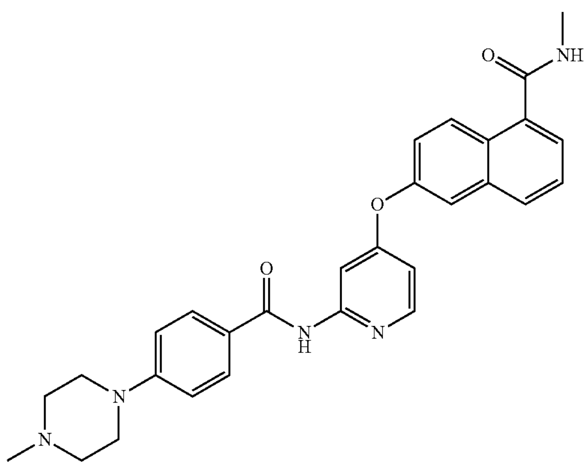 |
| S6 | 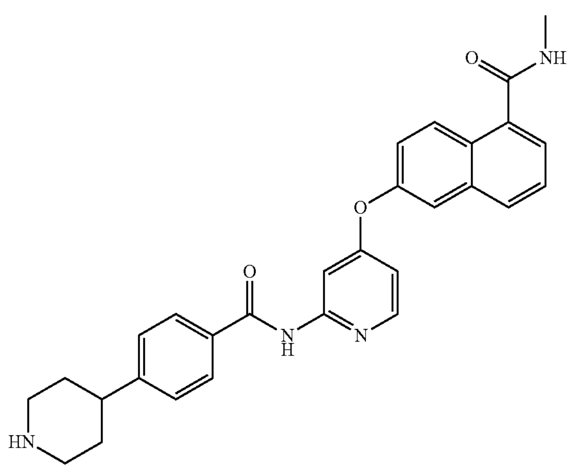 [SMILES: CNC(=O)c1cccc2cc(Oc3ccnc(NC(=O)c4ccc(C5CCNCC5)cc4)c3)ccc12] |

TABLE 1-continued
| Compound | Structure |
|---|---|
| S7 | 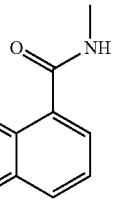 |
| S8 | 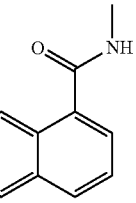 |
| S9 | 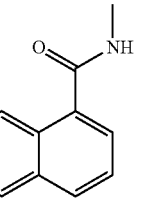 |

TABLE 1-continued
| Compound | Structure |
|---|---|
| S10 | 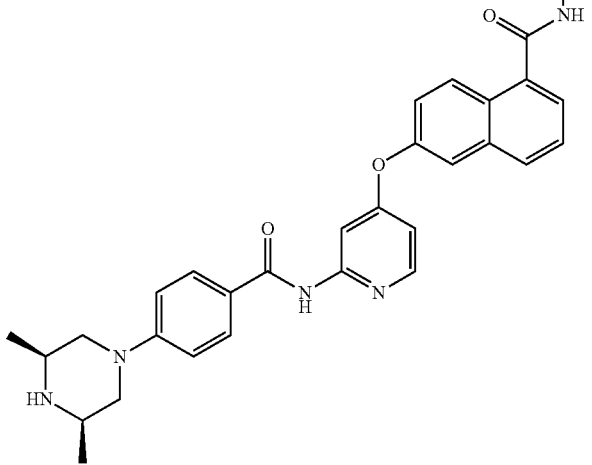 |
| S11 | 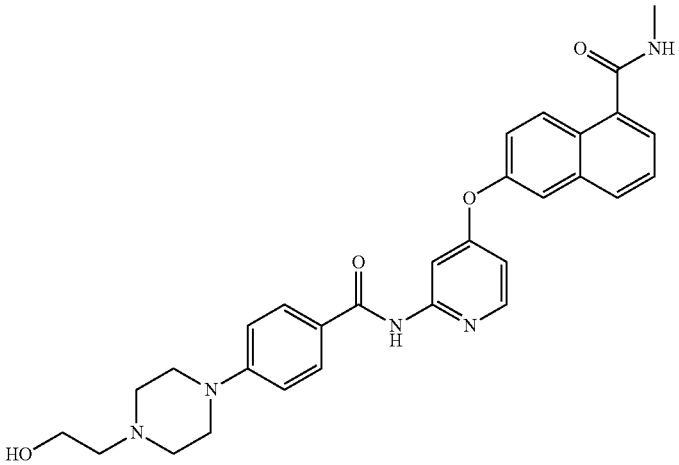 [SMILES: CNC(=O)c1cccc2cc(Oc3ccnc(NC(=O)c4ccc(N5CCN(CCO)CC5)cc4)c3)ccc12] |
| S12 | 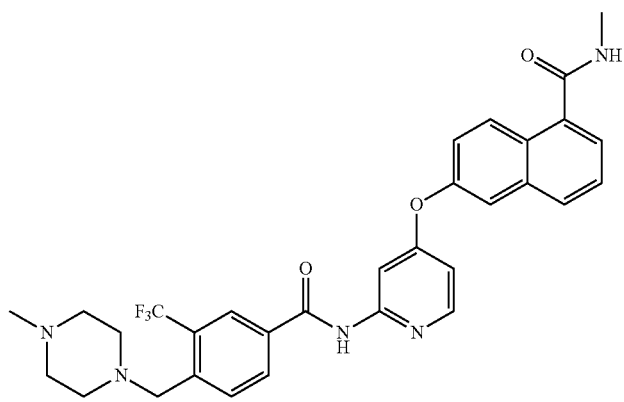 |

TABLE 1-continued
| Compound | Structure |
|---|---|
| S13 | 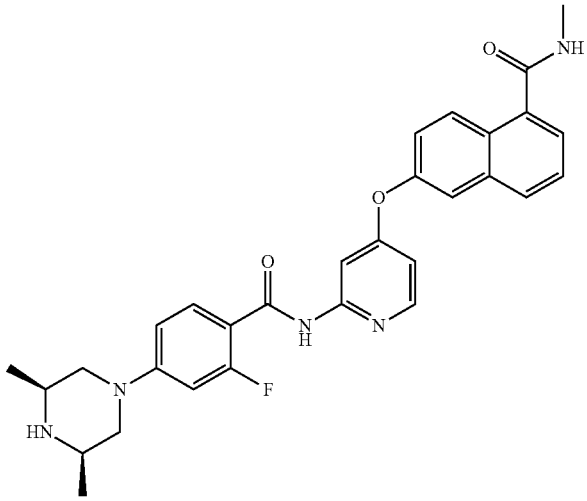 |
| S14 | 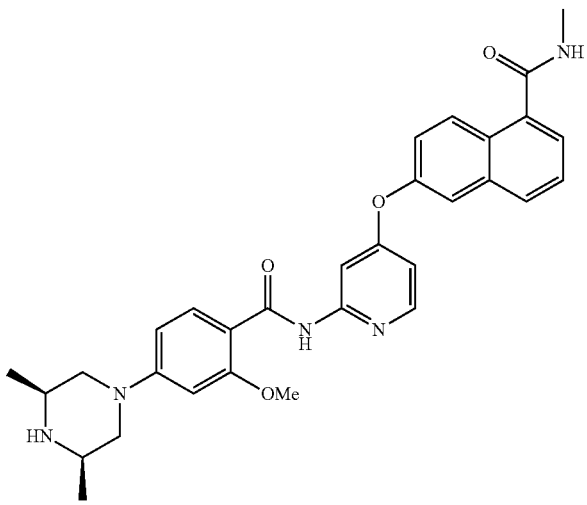 |
| S15 | 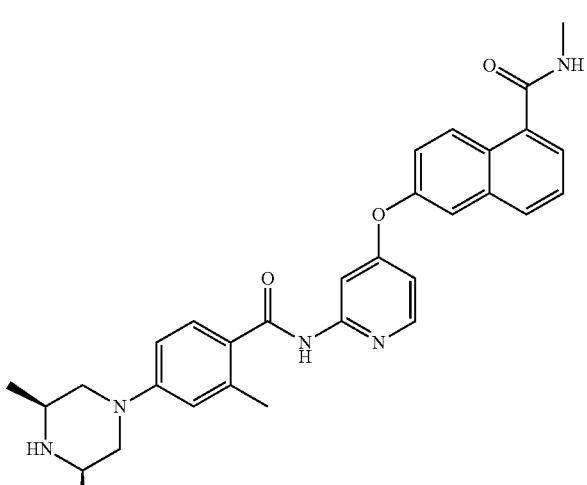 |

TABLE 1-continued
| Compound | Structure |
|---|---|
| S16 | 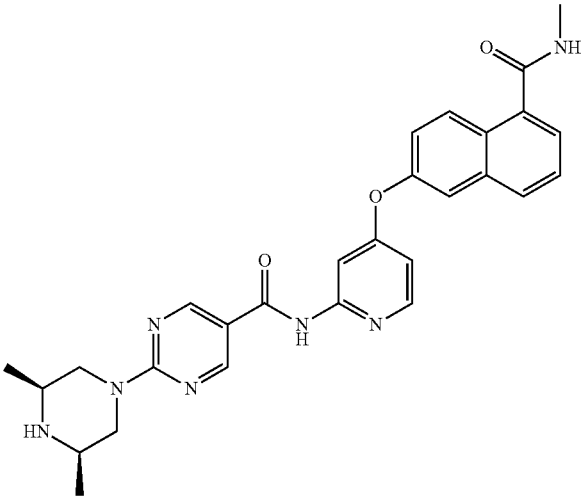 |
| S17 | 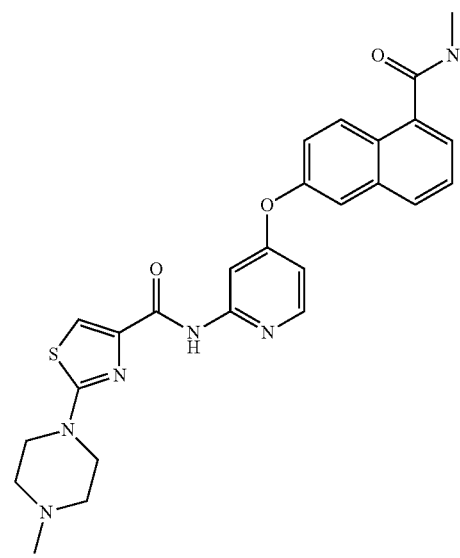 |
| S18 | 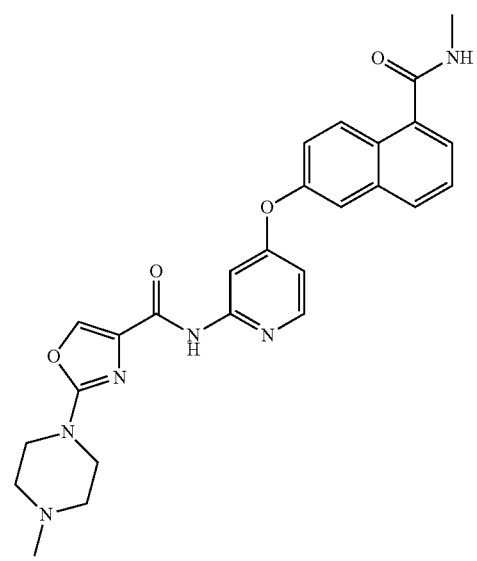 [SMILES: CNC(=O)c1cccc2cc(Oc3ccnc(NC(=O)c4coc(N5CCN(C)CC5)n4)c3)ccc12] |

TABLE 1-continued
| Compound | Structure |
| --- | --- |
| S19 | 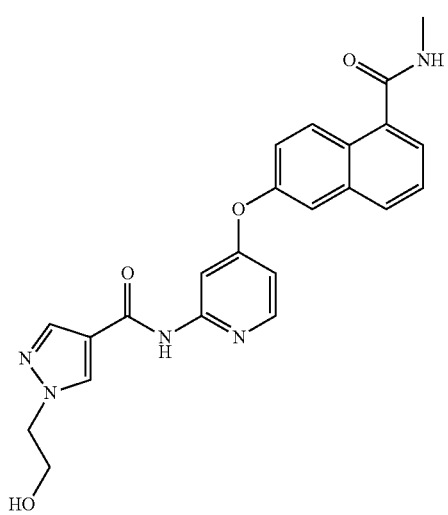 [SMILES: CNC(=O)c1cccc2cc(Oc3ccnc(NC(=O)c4cnn(CCO)c4)c3)ccc12] |
| S20 | 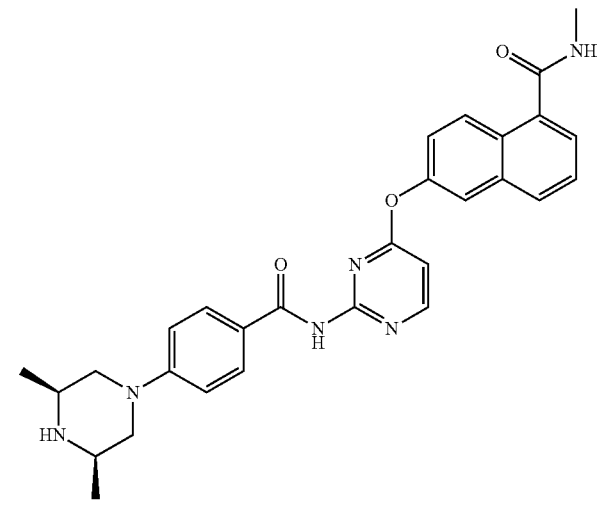 |
| S23 | 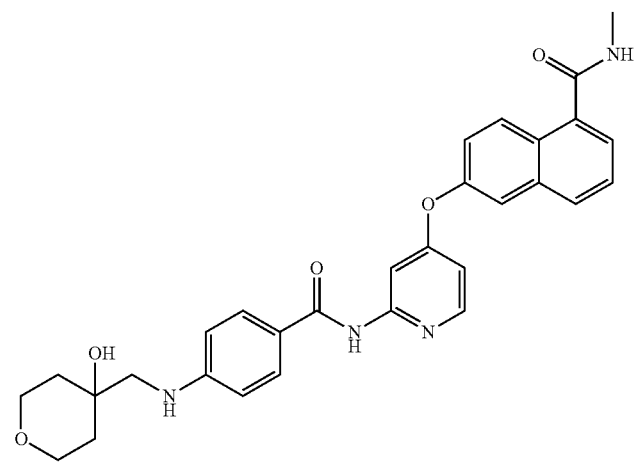 [SMILES: CNC(=O)c1cccc2cc(Oc3ccnc(NC(=O)c4ccc(NCC5(O)CCOCC5)cc4)c3)ccc12] |

TABLE 1-continued

| Compound | Structure |
|---|---|
| S24 | 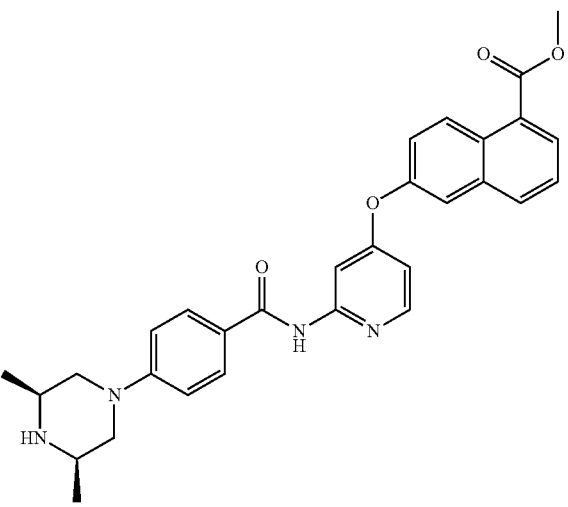 |

Pharmaceutical Composition Containing the Compound of Formula (I)

The present invention also relates to a pharmaceutical composition comprising a therapeutically effective amount of one or more selected from aminopyridine compounds of the formula (I), pharmaceutically acceptable salts, prodrugs, or hydrates or solvates thereof, and optionally, a pharmaceutically acceptable carrier that can be used to treat an associated disease such as cancer or the like. The pharmaceutical composition can be prepared in various forms depending on the route of administration.

One or more of the aminopyridine compound of the formula (I), pharmaceutically acceptable salts, prodrugs, and hydrates or solvates thereof, or the pharmaceutical composition comprising therapeutically effective amount of one or more of the aminopyridine compound (I), pharmaceutically acceptable salts, prodrugs, and hydrates or solvates thereof, can be used as a protein tyrosine kinase inhibitor, especially as FGFR inhibitor for the treatment of cancer. The FGFR preferably comprises FGFR1.

The pharmaceutically acceptable salt of the compound of the present invention can be prepared by direct salt formation reaction between the free base of the compound with an inorganic or organic acid. The inorganic or organic acid may be selected from the group consisting of hydrochloric acid, sulfuric acid, phosphoric acid, nitric acid, hydrofluoric acid, hydrobromic acid, formic acid, acetic acid, picric acid, citric acid, maleic acid, methanesulfonic acid, trifluoromethanesulfonic acid, ethanesulfonic acid and p-toluenesulfonic acid, and the like.

The compounds of the present invention possess outstanding activity of inhibiting FGFR kinase, such as FGFR1 and FGFR2. Therefore, the compound of the present invention, and the crystal forms, pharmaceutically acceptable inorganic or organic salts, hydrates or solvates thereof, and the pharmaceutical composition comprising the compound of the present invention as a main active ingredient can be used for treating, preventing and alleviating diseases related to FGFR activity or expression, for example, prevention and/or treatment of diseases associated with abnormal expression of the FGF/FGFR signaling pathway. According to the prior art, the compound of the present invention can be used to treat the following diseases: tumor-related disease, including breast cancer, lung cancer, bladder cancer, gastric cancer, pancreatic cancer, prostate cancer, colon cancer, multiple myeloma AML, liver cancer, Melanoma, head and neck cancer, thyroid cancer, renal cell carcinoma, glioblastoma, and testicular cancer. Especially, the tumor is selected from the group consisting of breast cancer, non-small cell lung cancer, bladder cancer, gastric cancer, pancreatic cancer, prostate cancer, colon cancer, multiple myeloma, liver cancer, Melanoma, head and neck cancer, thyroid cancer, renal cell carcinoma, glioblastoma, and testicular cancer. Most particularly, the cancer is non-small cell lung cancer, gastric cancer or multiple myeloma.

The pharmaceutical composition of the invention comprises the compound of the present invention or the pharmaceutically acceptable salts thereof in a safe and effective dosage range and pharmaceutically acceptable excipients or carriers. Wherein the "safe and effective dosage" means that the amount of compound is sufficient to significantly ameliorate the condition without causing significant side effects. Generally, the pharmaceutical composition contains 1-2000 mg of compound of the invention per dose, preferably, 5-200 mg of compound of the invention per dose.

Preferably, the "dose" is a capsule or tablet. "Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, for example, starch, lactose, sucrose, glucose, mannitol and silicic acid; (b) binders, for example, hydroxymethyl cellulose, alginates, gelalin, polyvinylpyrrolldone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need thereof, wherein the dose of administration is a pharmaceutically effective dose. For a person weighed 60 kg, the daily dose is usually 1-2000 mg, preferably 5-500 mg. Of course, the particular dose should also depend on various factors, such as the route of administration, patient healthy status, which are well within the skills of an experienced physician.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

I. COMPOUND PREPARATIVE EXAMPLES $^1$H-NMR was measured by Varian Mercury AMX300 model; MS was measured by VG ZAB-HS or VG-7070 model, EI source (70 ev) (if not indicated otherwise); all solvents were re-distilled before use, aqueous free solvents are obtained by drying according to the standard method; except indicated otherwise, all the reactions are carried out under the protection of nitrogen and TLC tracked, and all the post-treatment procedure includes washing with saturated aqueous solution of sodium chloride and drying with anhydrous sodium sulfate; purification of the product, unless otherwise indicated, was conducted with silica gel column chromatography (200-300 mesh); wherein the silica gel (200-300 mesh) was produced by Qingdao Ocean Chemical Plant, and GF254 thin-layer silica gel plate was produced by Yantai Jiangyou Silica Development Co., Ltd.

Preparation Example 1 Preparation of Compound S1

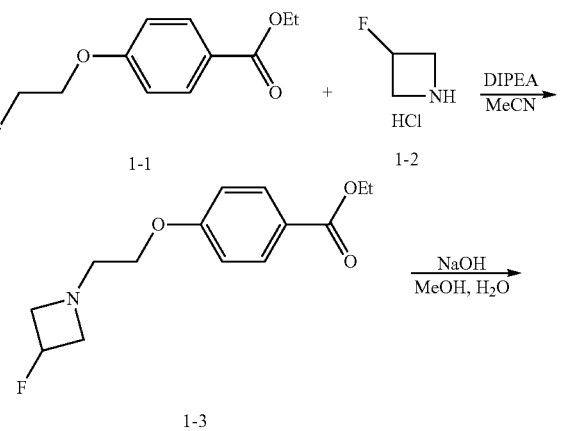

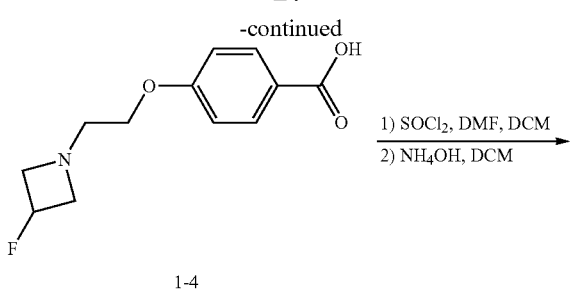

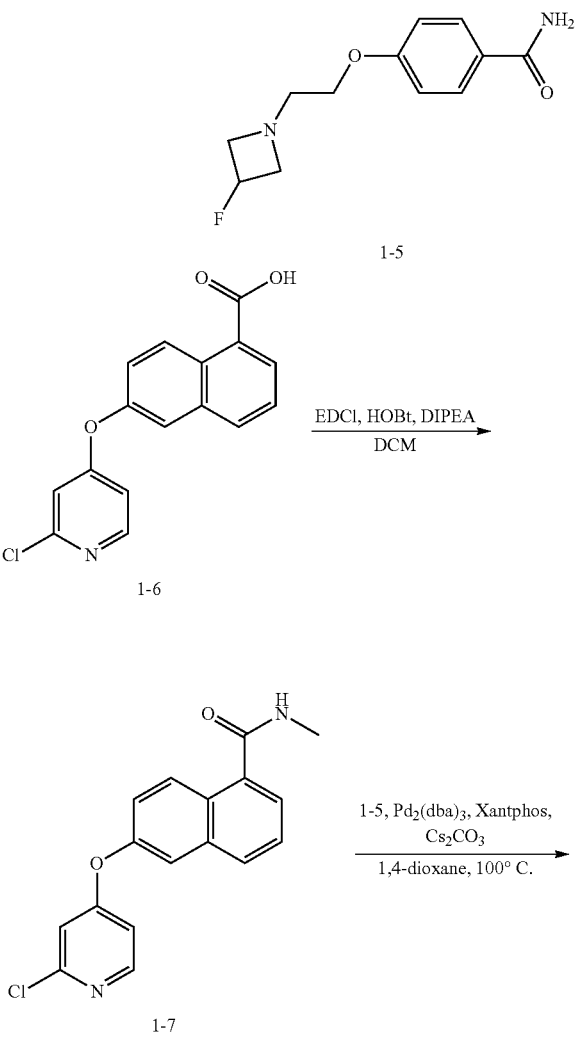

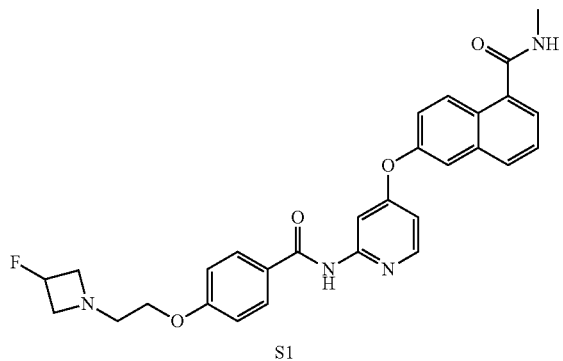 [SMILES: CNC(=O)c1cccc2cc(Oc3ccnc(NC(=O)c4ccc(OCCN5CC(F)C5)cc4)c3)ccc12 ; "S1"]

The synthesis method for compound 1-1 was conducted by referring to the method disclosed in WO2011140009.

Synthesis of Compound 1-3

Compound 1-1, Compound 1-2 (1.5 eq) were weighed in a single-necked flask, dissolved in acetonitrile, then DIPEA was added, and the reaction was carried out at 70° C. overnight. After the reaction was completed, it was extracted with dichloromethane and water, and the organic phase was washed with saturated brine, dried over anhydrous sodium sulfate. The mixture was applied to the column, and eluted by PE:EA=5:1 to provide compound 1-3.

Synthesis of Compound 1-4

Compound 1-3 was dissolved in methanol, and 2 eq aqueous solution of sodium hydroxide was added, and then the reaction mixture was heated at 60° C. for 4 h. After the reaction was completed, the reaction solution was cooled to room temperature, and the pH was adjusted to 5 to 6 with 2N HCl. A large amount of solid was precipitated and suction-filtered to give compound 1-4.

Synthesis of Compound 1-5

Compound 1-5 was dissolved in dichloromethane, DMF [N,N-dimethylformamide] (10 eq), sulfoxide (4 eq) were added in an ice bath, and the mixture was warmed to room temperature for 2 h. After the reaction was completed, the reaction solution was evaporated to dryness in vacuo, dissolved in DCM, and added into a solution of ammonia in dichloromethane cooled to 0° C., and reacted at room temperature for 5 h. After the reaction was completed, it was extracted with dichloromethane and water, and the organic phase was washed with saturated brine, dried over anhydrous sodium sulfate. The mixture was applied to the column and eluted by $CH_2Cl_2$:MeOH=50:1 to provide compound 1-5.

The compound 1-6 was synthesized by referring to *J. Med. Chem.* 2008, 51, 1649-1667.

Synthesis of Compound 1-7

Compound 1-6, methylamine hydrochloride (2.5 eq), EDCl [1-ethyl-(3-dimethylaminopropyl)carbodiimide hydrochloride] (1.5 eq), HOBt [1-Hydroxybenzotriazole] (1 eq) were weighed in a single-necked flask and dissolved in dichloromethane, then DIPEA [diisopropylethylamine] (2.5 eq) was added and allowed to react overnight at room temperature. After the reaction was completed, it was extracted with dichloromethane and water, and the organic phase was washed with saturated brine, dried over anhydrous sodium sulfate. The mixture was applied to the column and eluted by PE:EA (v:v)=1:1 to provide compound 1-7.

The synthesis of compound S1:

Compound 1-5, Compound 1-7 (1.2 eq), $Pd_2(dba)_3$ [tris(dibenzylideneacetone)dipalladium] (0.1 eq), Xantphos [4,5-bisdiphenylphosphine-9, 9-dimethyloxanthene (0.2 eq), cesium carbonate (2 eq) were dissolved in 1,4-dioxane under nitrogen, and reacted at 100° C. for 5 h. After the reaction was completed, it was extracted with dichloromethane and water, and the organic phase was washed with saturated brine, dried over anhydrous sodium sulfate. The mixture was applied to the column and eluted by $CH_2Cl_2$:MeOH=50:1 to provide compound S1. The analysis data of S1: $^1$H NMR (300 MHz, $CDCl_3$) δ 8.66 (s, 1H), 8.39 (d, J=9.1 Hz, 1H), 8.12 (d, J=5.6 Hz, 1H), 8.01 (s, 1H), 7.82 (t, J=8.8 Hz, 3H), 7.56 (s, 2H), 7.45 (t, J=7.6 Hz, 1H), 7.33 (d, J=9.9 Hz, 1H), 6.92 (d, J=8.6 Hz, 2H), 6.66 (d, J=4.2 Hz, 1H), 6.22 (d, J=5.0 Hz, 1H), 5.28-5.18 (m, 0.5H), 5.09-4.97 (m, 0.5H), 4.03 (t, J=5.1 Hz, 2H), 3.85-3.72 (m, 2H), 3.36-3.21 (m, 2H), 3.07 (d, J=4.8 Hz, 3H), 2.92 (t, J=5.0 Hz, 2H).

Preparation Example 2 Preparation of Compound S2

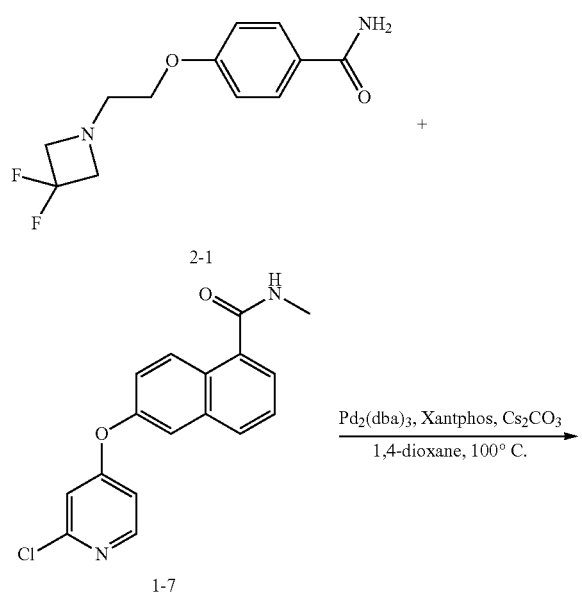

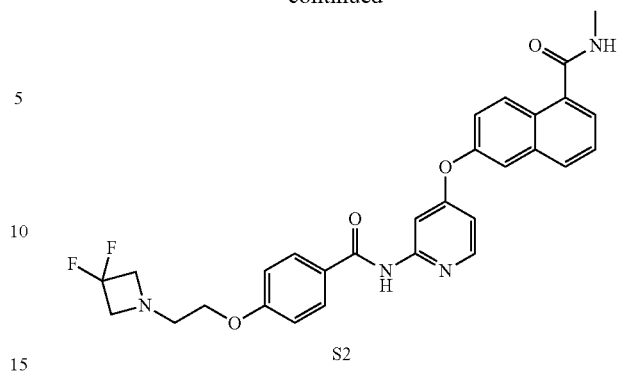

The synthesis of Compound 2-1 was the same to that of compound 1-5.

The synthesis of Compound S2 was the same to that of S1. The analysis data of S2: $^1$H NMR (300 MHz, CDCl$_3$) δ 8.53 (s, 1H), 8.36 (d, J=9.0 Hz, 1H), 8.10 (d, J=5.6 Hz, 1H), 7.98 (s, 1H), 7.79 (t, J=7.7 Hz, 3H), 7.53 (d, J=7.1 Hz, 2H), 7.42 (t, J=7.6 Hz, 1H), 7.34-7.26 (m, 1H), 6.88 (d, J=8.7 Hz, 2H), 6.62 (d, J=4.7 Hz, 1H), 6.01 (s, 1H), 4.03 (t, J=5.0 Hz, 2H), 3.68 (t, J=12.0 Hz, 4H), 3.05 (d, J=4.9 Hz, 3H), 2.94 (t, J=4.9 Hz, 2H).

Preparation Example 3 Preparation of Compound S3

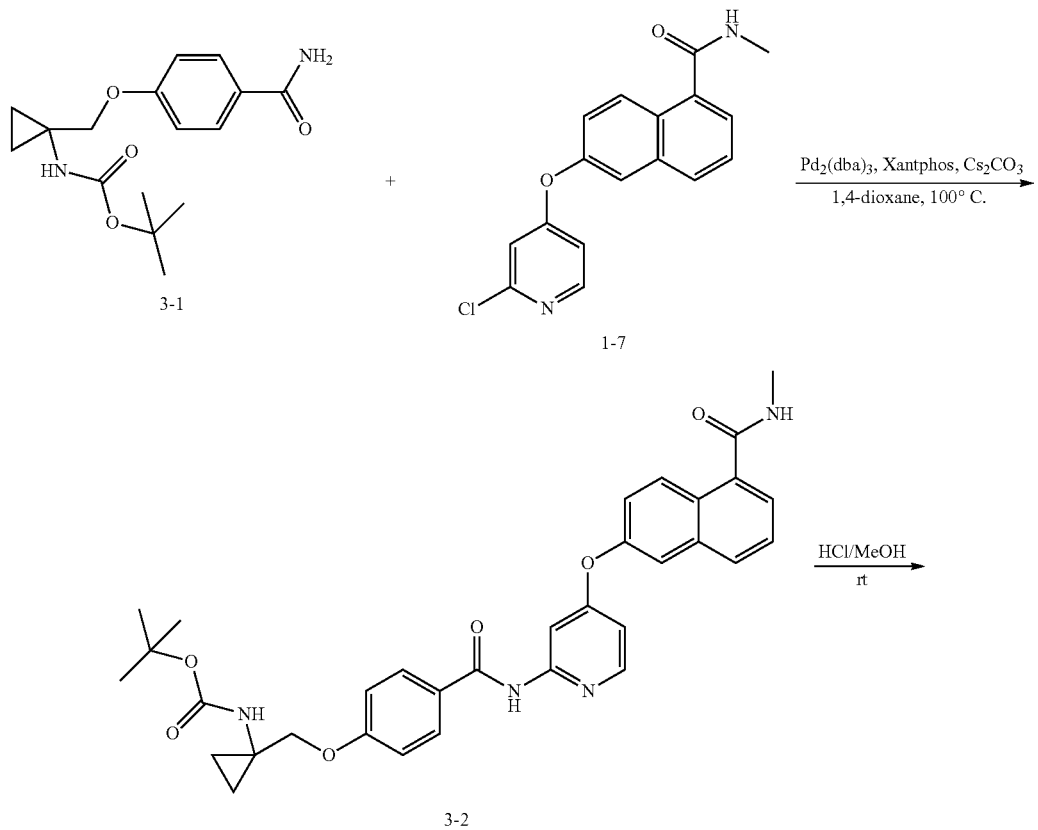

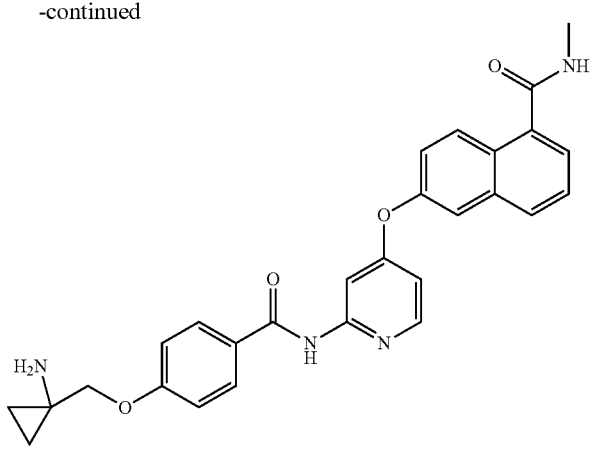

S3

The synthesis of Compound 3-1 was the same as that of compound 1-5.

The synthesis of Compound 3-2 was the same as that of S1.

The synthesis of compound S3:

The compound 3-2 was dissolved in methanol, and a 2N solution of methanolic hydrochloric acid (30 eq) was added and allowed to react at room temperature overnight. After the reaction was completed, the reaction mixture was evaporated to dryness in vacuo and extracted with saturated sodium bicarbonate solution and DCM, the organic phase was washed with saturated brine, dried over anhydrous sodium sulfate. The mixture was applied to the column and eluted by $CH_2Cl_2$:MeOH=30:1 to provide compound S3. The analysis data of S3: $^1$H NMR (300 MHz, $CDCl_3$) δ 8.58 (s, 1H), 8.41 (d, J=9.1 Hz, 1H), 8.15 (d, J=5.1 Hz, 1H), 8.02 (s, 1H), 7.84 (t, J=7.7 Hz, 3H), 7.57 (s, 2H), 7.51-7.42 (m, 1H), 7.35 (d, J=9.7 Hz, 1H), 6.95 (d, J=8.2 Hz, 2H), 6.67 (d, J=5.7 Hz, 1H), 6.12 (s, 1H), 3.88 (s, 2H), 3.09 (d, J=4.0 Hz, 3H), 0.77 (s, 2H), 0.65 (s, 2H).

Preparation Example 4 Preparation of Compound S4

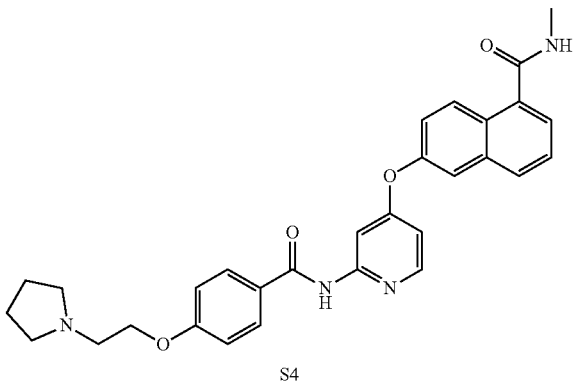

S4

The synthesis of Compound 4-1 was the same as that of 1-5.

The synthesis of Compound S4 was the same as that of S1. The analysis data of S4: $^1$H NMR (300 MHz, $CDCl_3$) δ 8.87 (s, 1H), 8.34 (d, J=9.2 Hz, 1H), 8.06 (d, J=5.6 Hz, 1H), 7.99 (s, 1H), 7.79 (t, J=7.0 Hz, 3H), 7.55-7.46 (m, 2H), 7.40 (t, J=7.6 Hz, 1H), 7.33-7.26 (m, 1H), 6.91 (d, J=8.4 Hz, 2H), 6.62 (d, J=4.9 Hz, 1H), 6.51-6.42 (m, 1H), 4.11 (t, J=5.8 Hz, 2H), 3.00 (d, J=4.7 Hz, 3H), 2.88 (t, J=5.7 Hz, 2H), 2.59 (s, 4H), 2.35 (s, 1H), 1.78 (s, 4H).

Preparation Example 5 Preparation of Compound S5

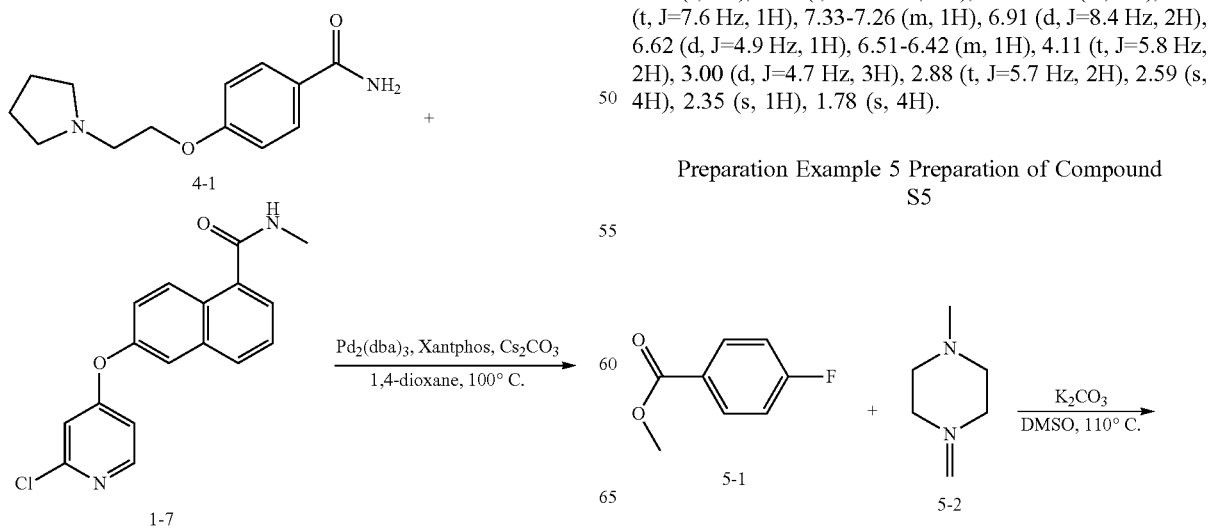

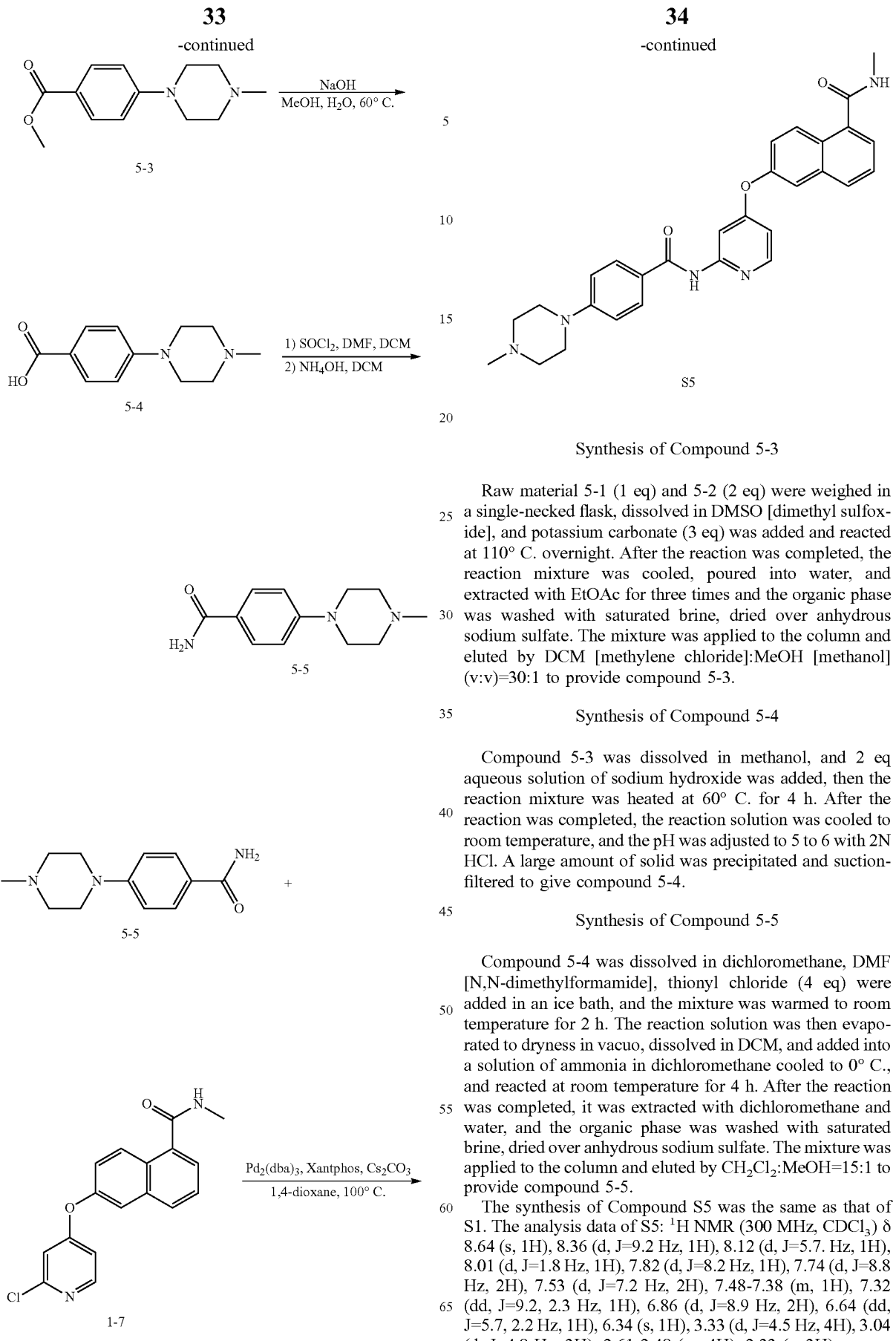

Synthesis of Compound 5-3

Raw material 5-1 (1 eq) and 5-2 (2 eq) were weighed in a single-necked flask, dissolved in DMSO [dimethyl sulfoxide], and potassium carbonate (3 eq) was added and reacted at 110° C. overnight. After the reaction was completed, the reaction mixture was cooled, poured into water, and extracted with EtOAc for three times and the organic phase was washed with saturated brine, dried over anhydrous sodium sulfate. The mixture was applied to the column and eluted by DCM [methylene chloride]:MeOH [methanol] (v:v)=30:1 to provide compound 5-3.

Synthesis of Compound 5-4

Compound 5-3 was dissolved in methanol, and 2 eq aqueous solution of sodium hydroxide was added, then the reaction mixture was heated at 60° C. for 4 h. After the reaction was completed, the reaction solution was cooled to room temperature, and the pH was adjusted to 5 to 6 with 2N HCl. A large amount of solid was precipitated and suction-filtered to give compound 5-4.

Synthesis of Compound 5-5

Compound 5-4 was dissolved in dichloromethane, DMF [N,N-dimethylformamide], thionyl chloride (4 eq) were added in an ice bath, and the mixture was warmed to room temperature for 2 h. The reaction solution was then evaporated to dryness in vacuo, dissolved in DCM, and added into a solution of ammonia in dichloromethane cooled to 0° C., and reacted at room temperature for 4 h. After the reaction was completed, it was extracted with dichloromethane and water, and the organic phase was washed with saturated brine, dried over anhydrous sodium sulfate. The mixture was applied to the column and eluted by $CH_2Cl_2$:MeOH=15:1 to provide compound 5-5.

The synthesis of Compound S5 was the same as that of S1. The analysis data of S5: $^1$H NMR (300 MHz, $CDCl_3$) δ 8.64 (s, 1H), 8.36 (d, J=9.2 Hz, 1H), 8.12 (d, J=5.7. Hz, 1H), 8.01 (d, J=1.8 Hz, 1H), 7.82 (d, J=8.2 Hz, 1H), 7.74 (d, J=8.8 Hz, 2H), 7.53 (d, J=7.2 Hz, 2H), 7.48-7.38 (m, 1H), 7.32 (dd, J=9.2, 2.3 Hz, 1H), 6.86 (d, J=8.9 Hz, 2H), 6.64 (dd, J=5.7, 2.2 Hz, 1H), 6.34 (s, 1H), 3.33 (d, J=4.5 Hz, 4H), 3.04 (d, J=4.8 Hz, 3H), 2.61-2.48 (m, 4H), 2.33 (s, 3H).

Preparation Example 6 Preparation of Compound S6
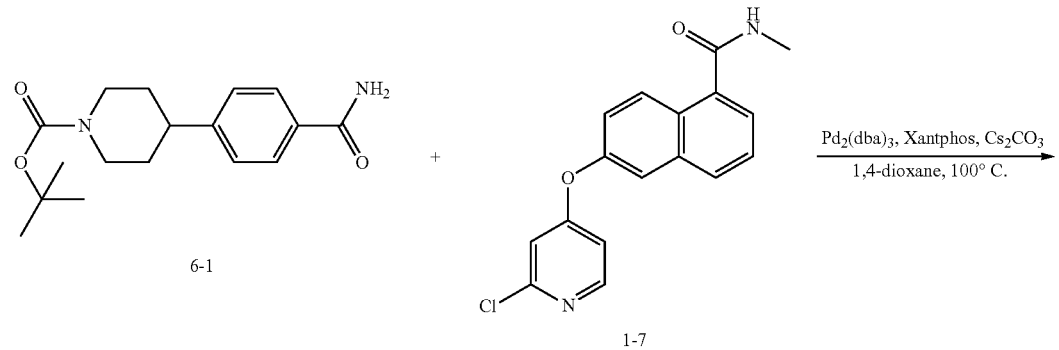
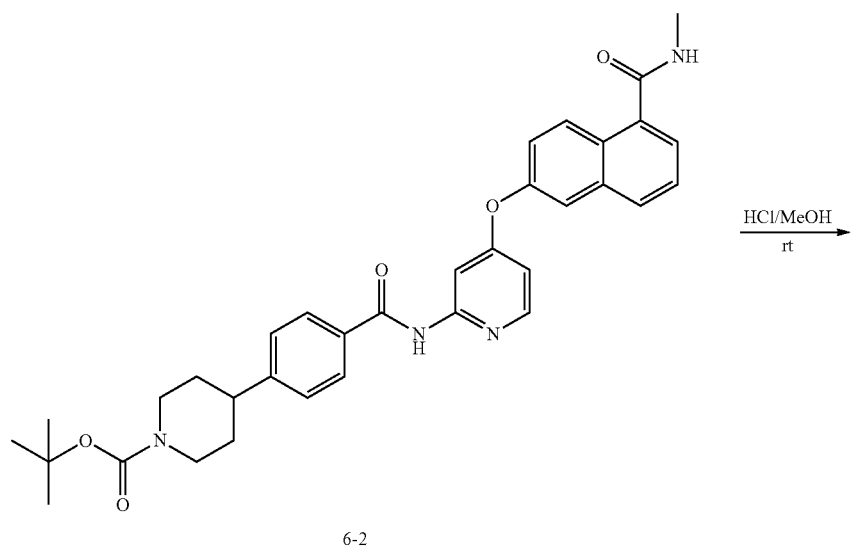
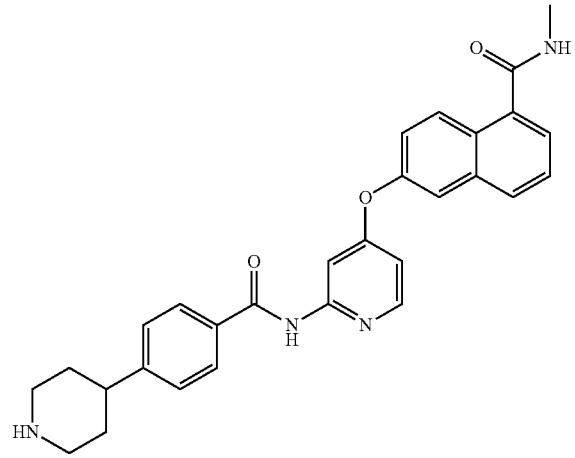

The synthesis of the compound 6-1 was conducted by referring to the method disclosed in WO2001060846.

The synthesis of Compound 6-2 was the same as that of S1.

The synthesis of S6 was the same as that of S3. The analysis data of S6: $^1$H NMR (300 MHz, CDCl$_3$) δ 8.83 (s, 1H), 8.31 (d, J=9.2 Hz, 1H), 8.10-7.93 (m, 2H), 7.73 (dd, J=13.3, 8.3 Hz, 3H), 7.46 (d, J=7.7 Hz, 2H), 7.40-7.33 (m, 1H), 7.24 (d, J=9.9 Hz, 2H), 6.57 (d, J=5.1 Hz, 1H), 6.36 (s, 1H), 3.20 (d, J=11.8 Hz, 2H), 2.97 (d, J=4.4 Hz, 3H), 2.69 (dd, J=25.0, 13.5 Hz, 2H), 1.73 (dd, J=31.8, 11.6 Hz, 4H).

Preparation Example 7 Preparation of Compound S7

Preparation Example 8 Preparation of Compound S8

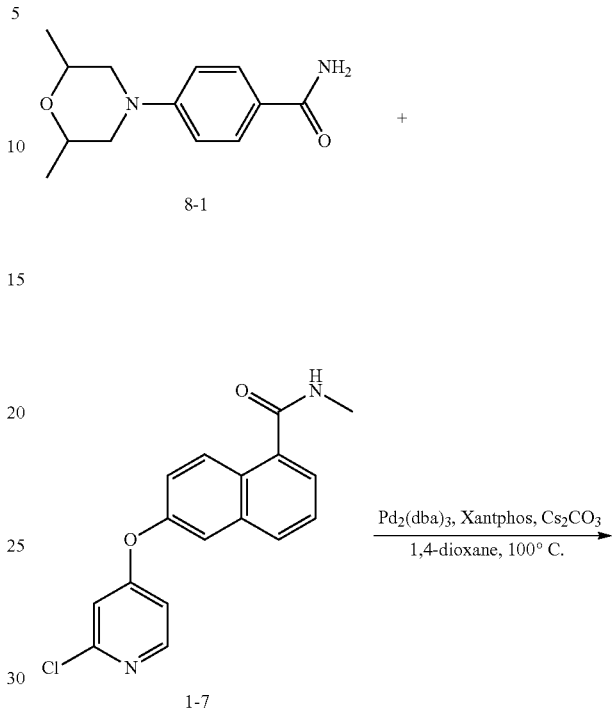

The synthesis of Compound 7-1 was the same as that of 5-5.

The synthesis of Compound S7 was the same as that of S1. The analysis data of S7: $^1$H NMR (300 MHz, CDCl$_3$) δ 8.55 (s, 1H), 8.40 (d, J=9.2 Hz, 1H), 8.15 (d, J=5.8 Hz, 1H), 8.03 (d, J=1.7 Hz, 1H), 7.82 (dd, J=17.4, 8.4 Hz, 3H), 7.57 (d, J=5.6 Hz, 2H), 7.51-7.43 (m, 1H), 7.35 (dd, J=9.1, 2.3 Hz, 1H), 6.89 (d, J=8.8 Hz, 2H), 6.66 (dd, J=5.7, 2.1 Hz, 1H), 6.13 (s, 1H), 3.92-3.81 (m, 4H), 3.36-3.23 (m, 4H), 3.09 (d, J=4.9 Hz, 3H).

The synthesis of Compound 8-1 was the same as that of 5-5.

The synthesis of Compound S8 was the same as that of S1. The analysis data of S8: $^1$H NMR (300 MHz, CDCl$_3$) δ 8.55 (s, 1H), 8.40 (d, J=9.2 Hz, 1H), 8.15 (d, J=5.7 Hz, 1H), 8.03 (s, 1H), 7.81 (dd, J=21.6, 8.4 Hz, 1H), 7.56 (s, 1H), 7.47 (t, J=7.6 Hz, 1H), 7.35 (d, J=8.8 Hz, 1H), 7.26 (s, 1H), 6.88 (d, J=8.6 Hz, 1H), 6.66 (d, J=4.8 Hz, 1H), 6.14 (d, J=4.4 Hz, 1H), 3.87-3.71 (m, 1H), 3.59 (d, J=12.0 Hz, 1H), 3.09 (d, J=4.7 Hz, 1H), 2.51 (t, J=11.3 Hz, 1H), 1.27 (d, J=6.2 Hz, 1H).

Preparation Example 9 Preparation of Compound S9
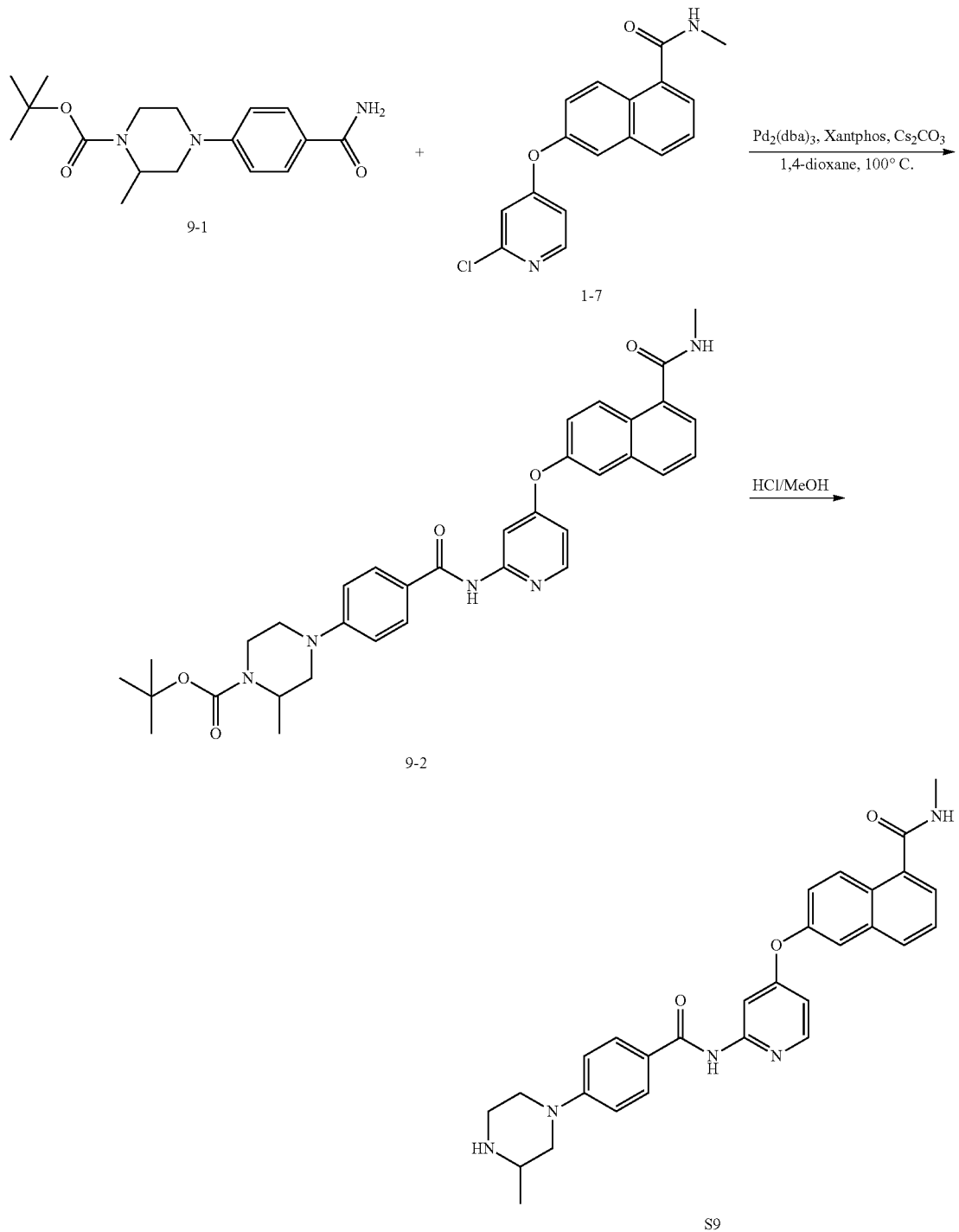
The synthesis of Compound 9-1 was the same as that of 5-5.
The synthesis of Compound 9-2 was the same as that of S1.
The synthesis of Compound S9 was the same as that of S3. The analysis data of S9: $^1$H NMR (300 MHz, CDCl$_3$) δ 8.54 (s, 1H), 8.39 (d, J=8.9 Hz, 1H), 8.15 (d, J=5.7 Hz, 1H), 8.03 (s, 1H), 7.84 (d, J=8.5 Hz, 1H), 7.76 (d, J=8.5 Hz, 2H), 7.56 (s, 2H), 7.46 (t, J=7.6 Hz, 1H), 7.34 (d, J=9.0 Hz, 1H), 6.88 (d, J=8.7 Hz, 2H), 6.66 (d, J=5.9 Hz, 1H), 6.17 (s, 1H), 3.67 (d, J=11.9 Hz, 2H), 3.18-3.01 (m, 5H), 2.96 (d, J=13.2 Hz, 2H), 2.82 (t, J=11.4 Hz, 1H), 2.46 (t, J=11.3 Hz, 1H), 1.14 (d, J=6.2 Hz, 3H).

Preparation Example 10 Preparation of Compound S10
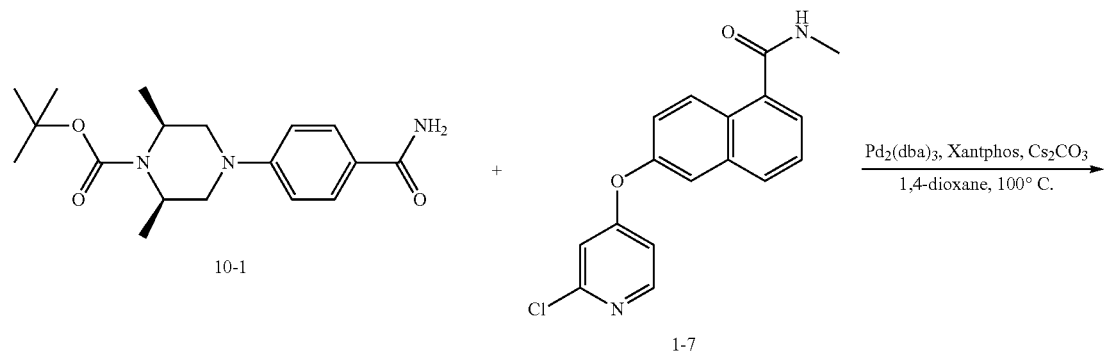
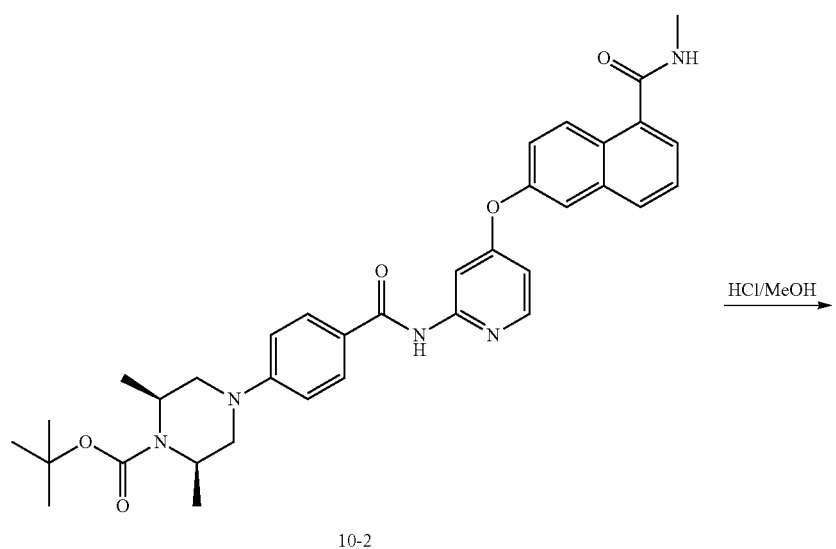
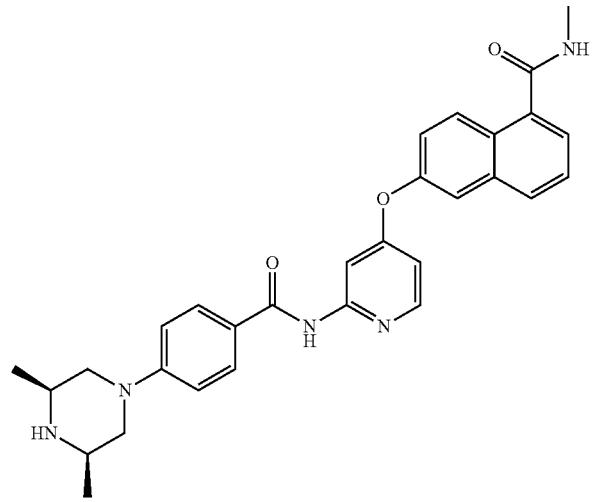

The synthesis of Compound 10-1 was the same as that of 5-5.

The synthesis of Compound 10-2 was the same as that of S1.

The synthesis of Compound S10 was the same as that of S3. The analysis data of S10: $^1$H NMR (300 MHz, CDCl$_3$) δ 8.51 (s, 1H), 8.40 (d, J=9.2 Hz, 1H), 8.15 (d, J=5.7 Hz, 1H), 8.03 (s, 1H), 7.85 (d, J=8.1 Hz, 1H), 7.76 (d, J=8.6 Hz, 2H), 7.57 (d, J=5.9 Hz, 2H), 7.46 (t, J=7.6 Hz, 1H), 7.38-7.31 (m, 1H), 6.89 (d, J=8.7 Hz, 2H), 6.70-6.62 (m, 1H), 6.13 (d, J=3.6 Hz, 1H), 3.67 (d, J=11.1 Hz, 2H), 3.09 (d, J=4.7 Hz, 3H), 2.99 (td, J=9.1, 4.4 Hz, 2H), 2.41 (t, J=11.2 Hz, 2H), 1.15 (d, J=6.2 Hz, 6H).

Preparation Example 11 Preparation of Compound S11

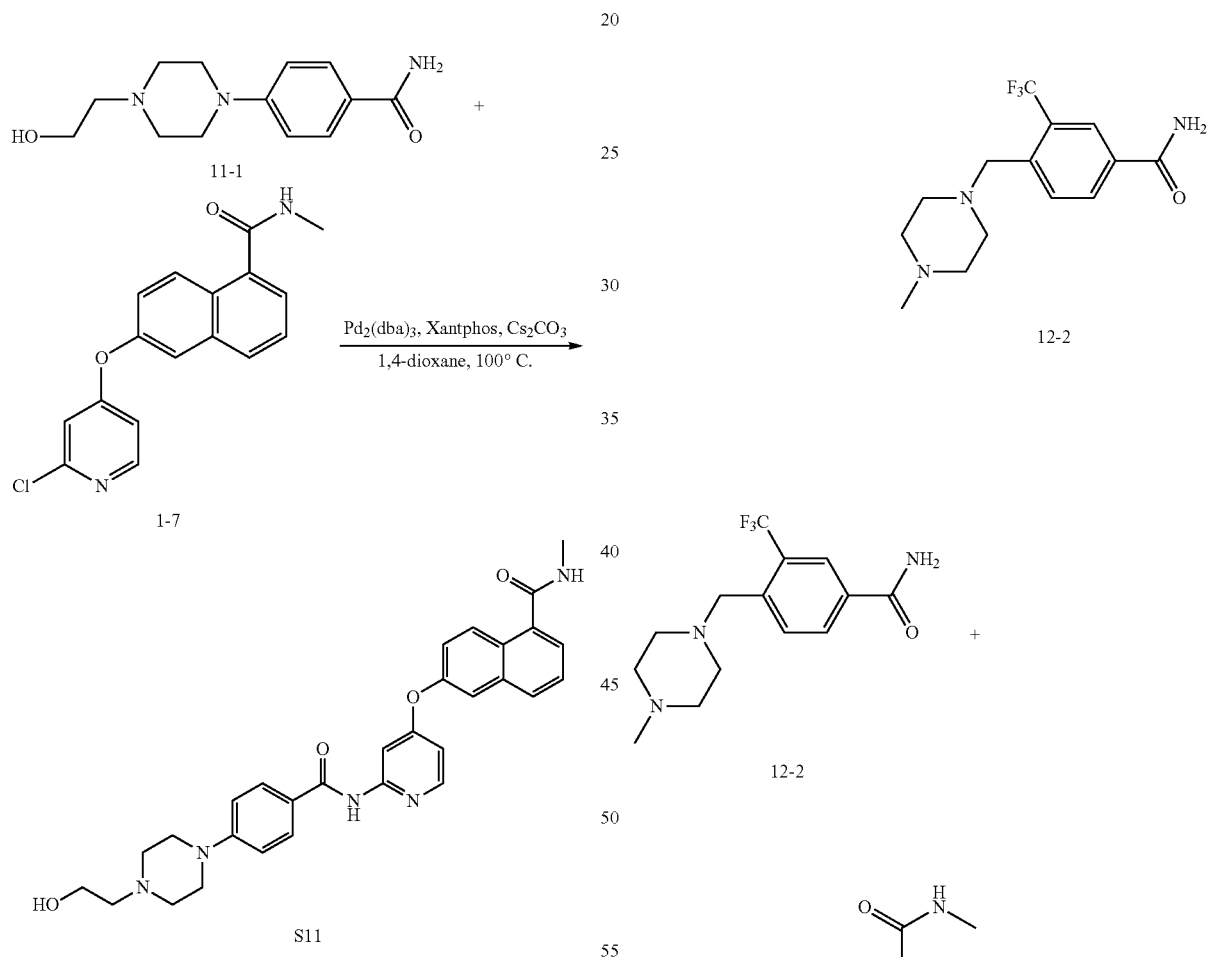

The synthesis of Compound 11-1 was the same as that of 5-5.

The synthesis of Compound S11 was the same as that of S1. The analysis data of S11: $^1$H NMR (300 MHz, CDCl$_3$) δ 8.27 (d, J=9.2 Hz, 1H), 8.06 (d, J=5.7 Hz, 1H), 7.89 (s, 1H), 7.79 (d, J=8.0 Hz, 1H), 7.72 (d, J=8.6 Hz, 2H), 7.52 (d, J=6.8 Hz, 2H), 7.42 (t, J=7.5 Hz, 1H), 7.27 (d, J=5.5 Hz, 2H), 6.84 (d, J=8.8 Hz, 2H), 6.64 (d, J=5.7 Hz, 1H), 3.62 (t, J=5.3 Hz, 2H), 3.28 (s, 6H), 2.61 (s, 5H), 2.54 (t, J=5.4 Hz, 2H).

Preparation Example 12 Preparation of Compound S12

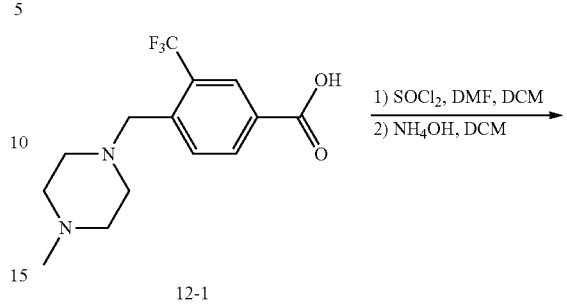

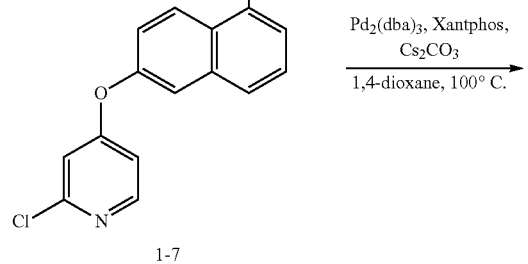

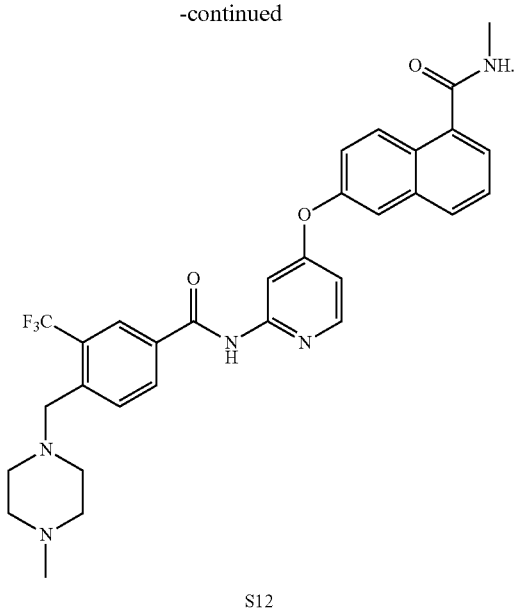
S12
The synthesis of the compound 12-1 was conducted by referring to the method disclosed in WO2013170774.
The synthesis of Compound 12-2 was the same as that of 5-5.
The synthesis of Compound S12 was the same as that of S1. The analysis data of S12: $^1$H NMR (300 MHz, CDCl$_3$) δ 8.71 (s, 1H), 8.43 (d, J=9.2 Hz, 1H), 8.15 (d, J=5.8 Hz, 2H), 8.03 (d, J=6.7 Hz, 1H), 8.00-7.92 (m, 2H), 7.86 (d, J=8.1 Hz, 1H), 7.59 (d, J=6.7 Hz, 2H), 7.49 (t, J=7.6 Hz, 1H), 7.35 (d, J=9.1 Hz, 1H), 6.69 (d, J=5.3 Hz, 1H), 3.71 (s, 2H), 3.11 (d, J=4.8 Hz, 3H), 2.54 (s, 8H), 2.32 (s, 4H).
Preparation Example 13 Preparation of Compound S13
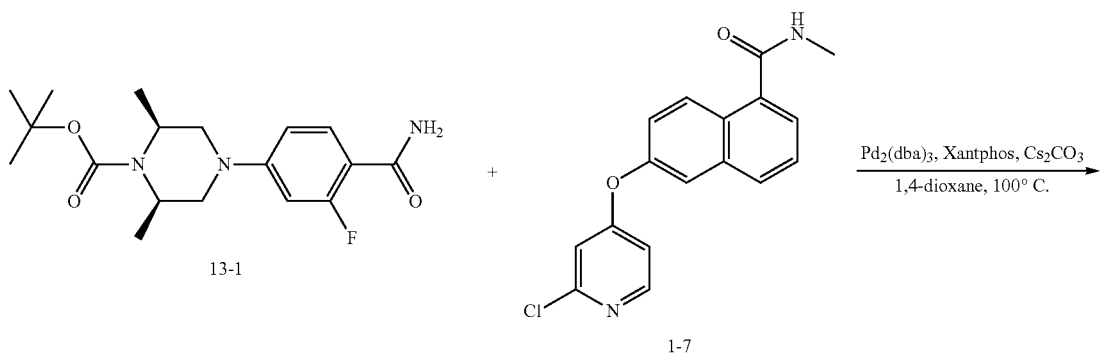
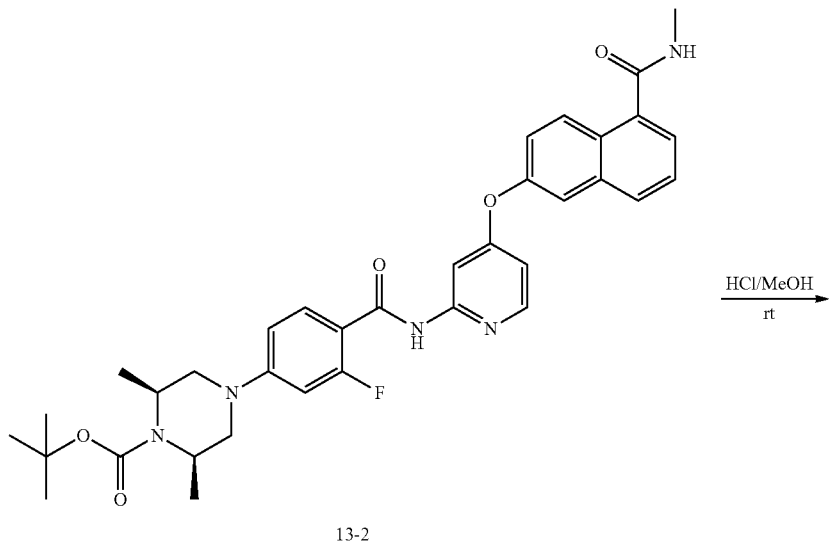
13-2

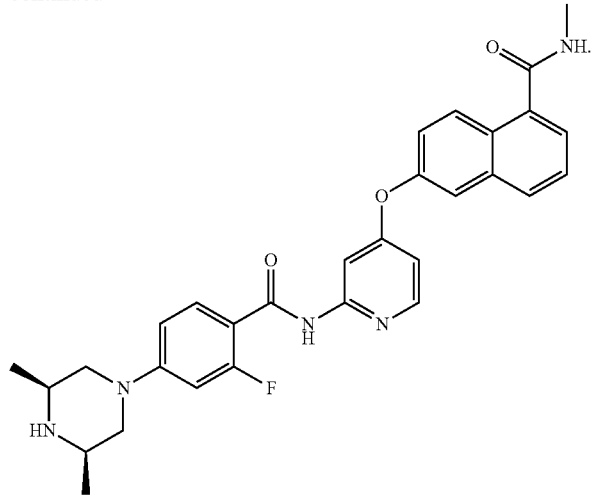
S13
The synthesis of Compound 13-1 was the same as that of 5-5.
The synthesis of Compound 13-2 was the same as that of S1.
The synthesis of Compound S13 was the same as that of S3. The analysis data of S13: $^1$H NMR (300 MHz, CDCl$_3$) δ 12.38 (s, 1H), 8.40 (d, J=9.2 Hz, 1H), 8.21-8.10 (m, 2H), 8.05 (s, 1H), 7.84 (d, J=8.2 Hz, 1H), 7.55 (d, J=6.4 Hz, 2H), 7.45 (t, J=7.6 Hz, 1H), 7.34 (d, J=11.1 Hz, 1H), 6.93 (dd, J=17.1, 8.9 Hz, 2H), 6.64 (d, J=5.5 Hz, 1H), 6.23 (s, 1H), 3.48 (s, 2H), 3.12-3.03 (m, 5H), 2.84 (s, 3H), 2.53 (t, J=10.8 Hz, 2H), 1.14 (d, J=6.3 Hz, 6H).
Preparation Example 14 Preparation of Compound S14
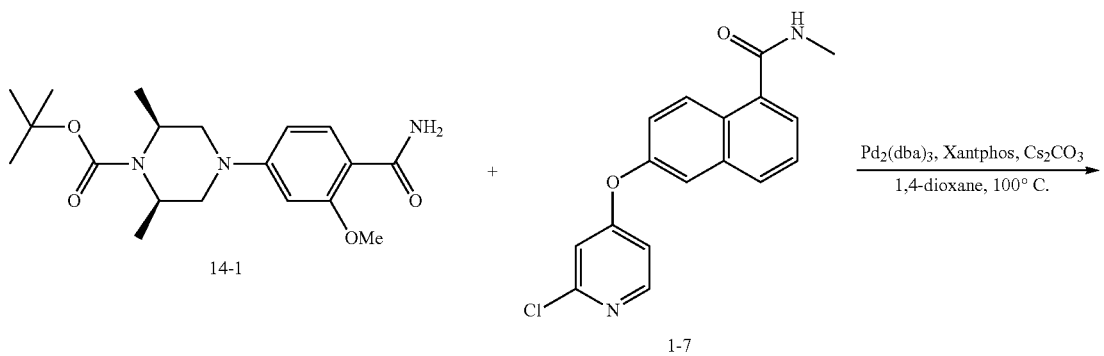

-continued
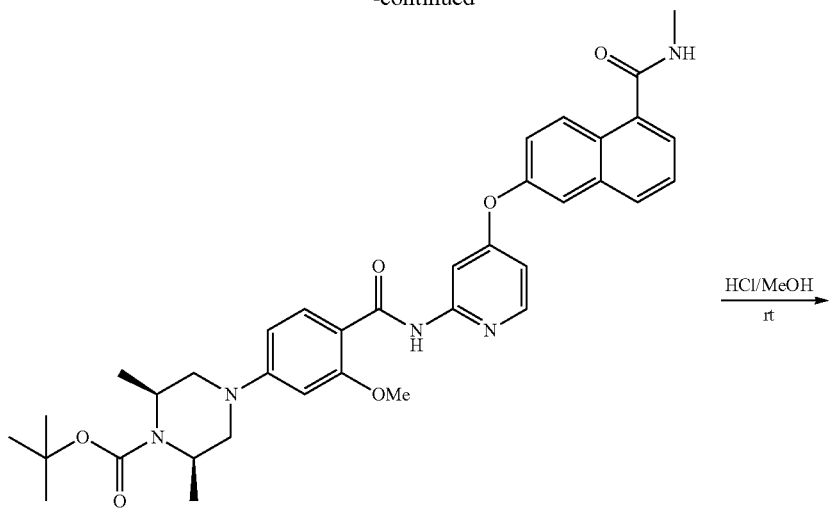
14-2
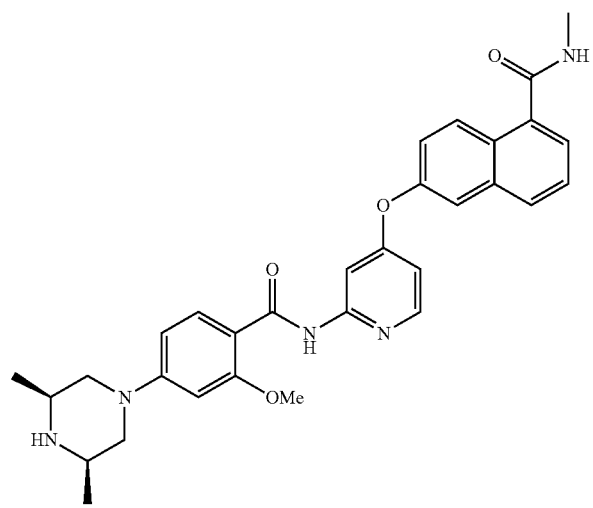
S14
The synthesis of Compound 14-1 was the same as that of 5-5.
The synthesis of Compound 14-2 was the same as that of 5-5.
The synthesis of Compound S14 was the same as that of S3. The analysis data of S14: $^1$H NMR (300 MHz, CDCl3) δ 10.28 (s, 1H), 8.37 (d, J=9.2 Hz, 1H), 8.17 (d, J=5.7 Hz, 1H), 8.09 (s, 1H), 7.98 (d, J=8.9 Hz, 1H), 7.82 (d, J=8.1 Hz, 1H), 7.53 (d, J=6.9 Hz, 2H), 7.45 (d, J=7.8 Hz, 1H), 7.34 (d, J=9.3 Hz, 1H), 6.63 (d, J=6.3 Hz, 1H), 6.53 (d, J=8.8 Hz, 1H), 6.36 (s, 1H), 6.27 (d, J=4.6 Hz, 1H), 4.05 (s, 3H), 3.64 (d, J=11.9 Hz, 2H), 3.05 (d, J=4.8 Hz, 3H), 2.98 (d, J=6.6 Hz, 2H), 2.42 (t, J=11.2 Hz, 2H), 1.15 (d, J=6.2 Hz, 6H).

Preparation Example 15 Preparation of Compound S15
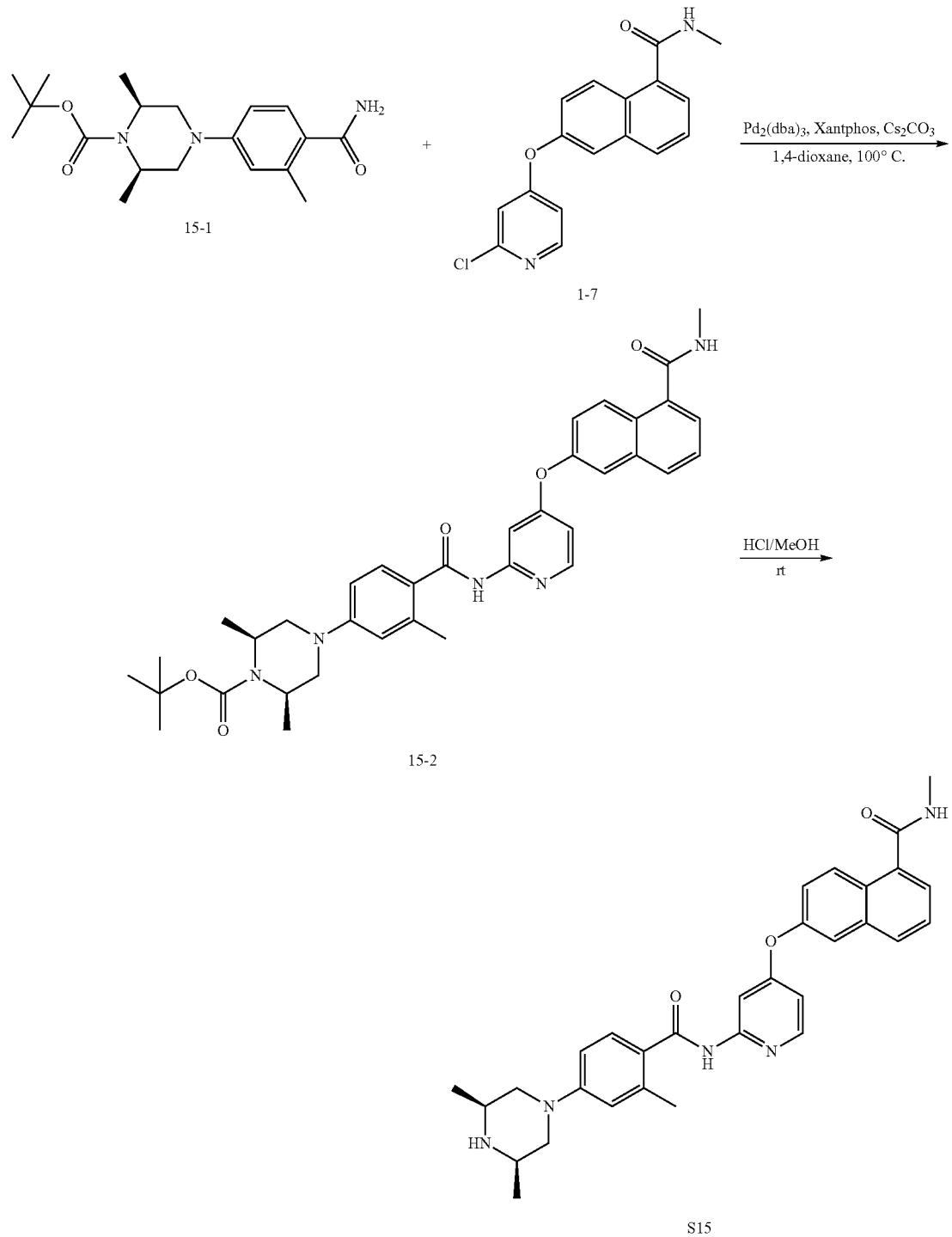
The synthesis of Compound 15-1 was the same as that of 5-5.
The synthesis of Compound 15-2 was the same as that of S1.
The synthesis of Compound S15 was the same as that of S3. The analysis data of S15: $^1$H NMR (300 MHz, CDCl$_3$) δ 8.40 (d, J=9.2 Hz, 1H), 8.12 (d, J=5.6 Hz, 1H), 7.91 (d, J=8.9 Hz, 1H), 7.79 (d, J=8.2 Hz, 1H), 7.50 (d, J=7.0 Hz, 1H), 7.491-7.43 (m, 2H), 7.24 (d, J=2.3 Hz, 1H), 6.75 (d, J=7.7 Hz, 2H), 6.41 (d, J=8.8 Hz, 1H), 6.27 (s, 1H), 6.13 (s, 1H), 3.67 (d, J=10.9 Hz, 2H), 3.12-3.03 (m, 5H), 2.45 (t, J=11.2 Hz, 2H), 2.25 (s, 3H), 1.17 (d, J=6.8 Hz, 6H).

Preparation Example 16 Preparation of Compound S16
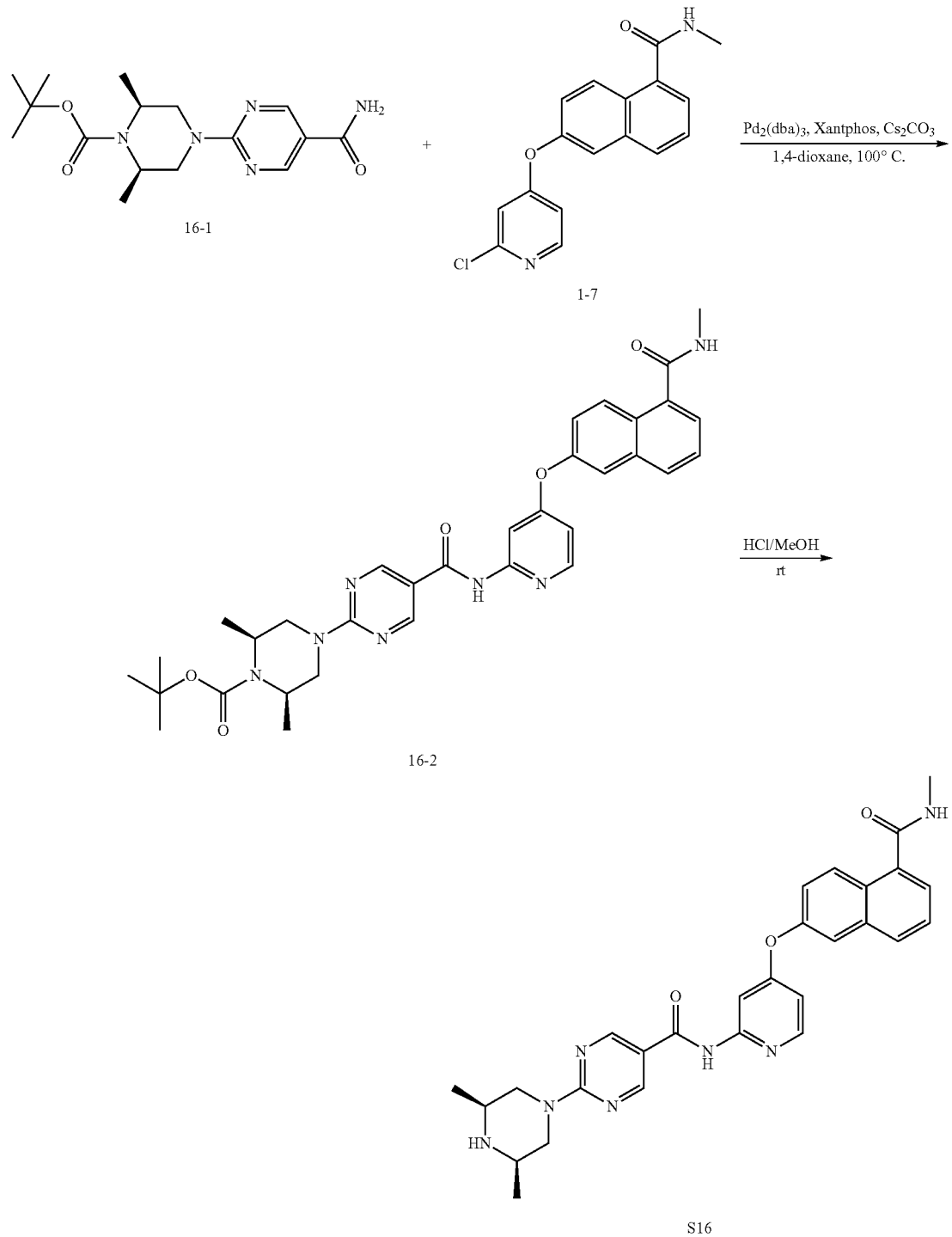
The synthesis of Compound 16-1 was the same as that of 5-5.
The synthesis of Compound 16-2 was the same as that of S1.
The synthesis of Compound S16 was the same as that of S3. The analysis data of S16: $^1$H NMR (300 MHz, CDCl$_3$) δ 8.77 (s, 2H), 8.49-8.36 (m, 2H), 8.15 (d, J=5.7 Hz, 1H), 7.97 (s, 1H), 7.85 (d, J=8.3 Hz, 1H), 7.57 (d, J=6.8 Hz, 2H), 7.51-7.44 (m, 1H), 7.34 (d, J=9.2 Hz, 1H), 6.67 (d, J=3.5 Hz, 1H), 6.11 (d, J=5.7 Hz, 1H), 4.77 (d, J=12.7 Hz, 2H), 3.10 (d, J=4.7 Hz, 3H), 2.94-2.81 (m, 2H), 2.54 (t, J=11.7 Hz, 2H), 1.25 (s, 1H), 1.16 (d, J=6.2 Hz, 6H).

Preparation Example 17 Preparation of Compound S17

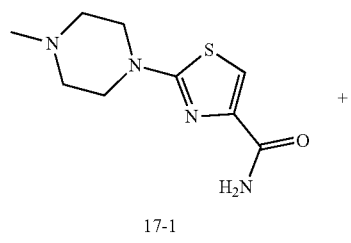

17-1

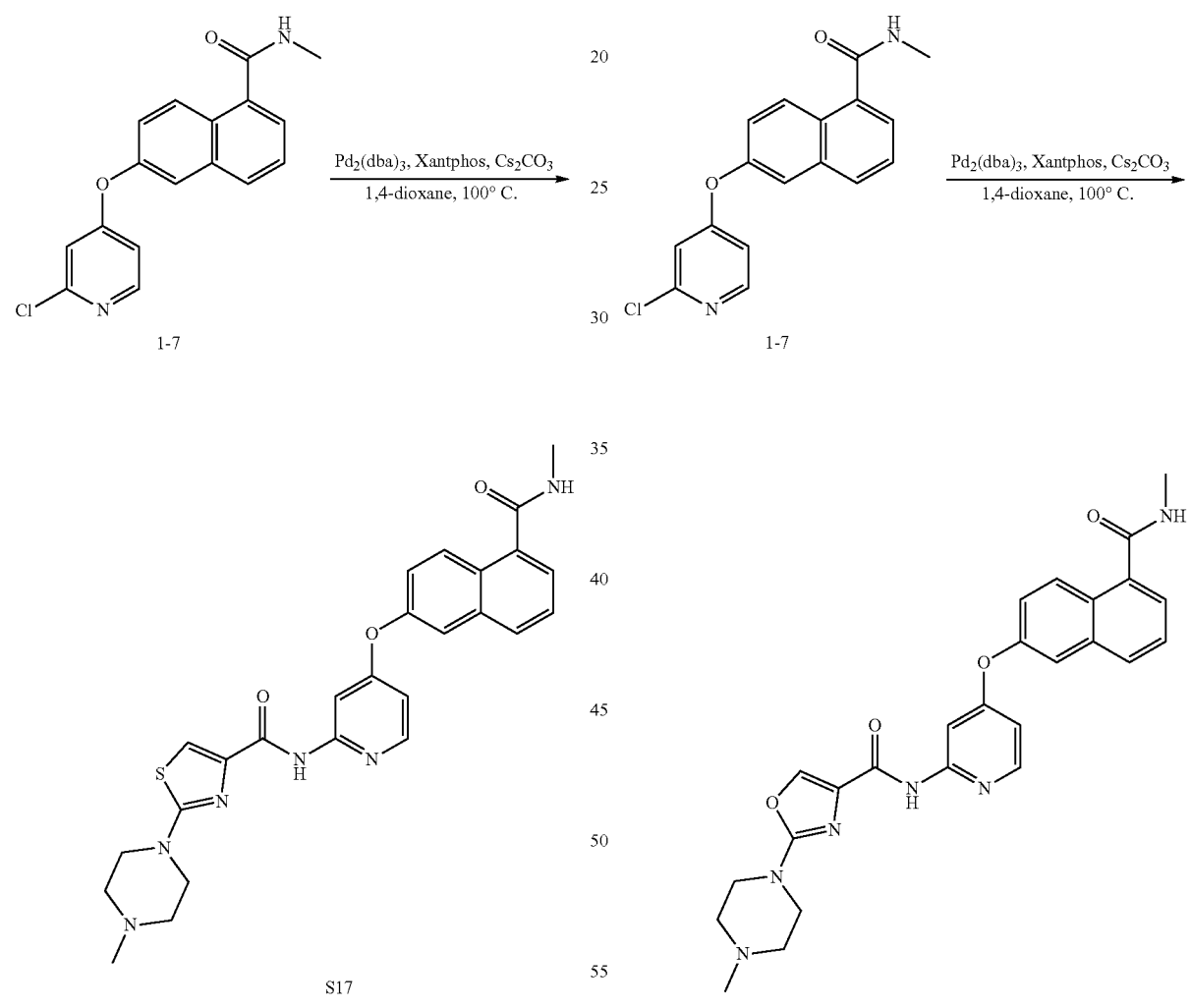

S17

The synthesis of Compound 17-1 was the same as that of 5-5.

The synthesis of Compound S17 was the same as that of S1. The analysis data of S17: $^1$H NMR (300 MHz, CDCl$_3$) δ 9.61 (s, 1H), 8.40 (d, J=9.0 Hz, 1H), 8.19 (d, J=5.6 Hz, 1H), 8.02 (d, J=1.8 Hz, 1H), 7.85 (d, J=8.3 Hz, 1H), 7.57 (d, J=6.7 Hz, 2H), 7.47 (t, J=7.5 Hz, 1H), 7.42 (s, 1H), 7.36 (d, J=9.2 Hz, 1H), 6.71-6.64 (m, 1H), 6.08 (d, J=4.5 Hz, 1H), 3.58-3.52 (m, 4H), 3.10 (d, J=4.9 Hz, 3H), 2.56-2.49 (m, 4H), 2.36 (s, 3H).

Preparation Example 18 Preparation of Compound S18

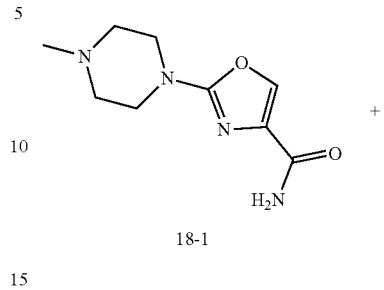

18-1

S18

The synthesis of Compound 18-1 was the same as that of 5-5.

The synthesis of Compound S18 was the same as that of S1. The analysis data of S18: $^1$H NMR (300 MHz, CDCl$_3$) δ 9.26 (s, 1H), 8.40 (d, J=9.2 Hz, 1H), 8.18 (d, J=5.6 Hz, 1H), 7.98 (s, 1H), 7.85 (d, J=8.2 Hz, 1H), 7.76 (s, 1H), 7.58 (d, J=7.1 Hz, 2H), 7.47 (t, J=7.8 Hz, 1H), 7.35 (d, J=9.3 Hz, 1H), 6.67 (d, J=3.8 Hz, 1H), 6.05 (d, J=14.5 Hz, 1H), 3.56 (s, 4H), 3.10 (d, J=4.8 Hz, 3H), 2.49 (s, 4H), 2.34 (s, 3H).

Preparation Example 19 Preparation of Compound S19

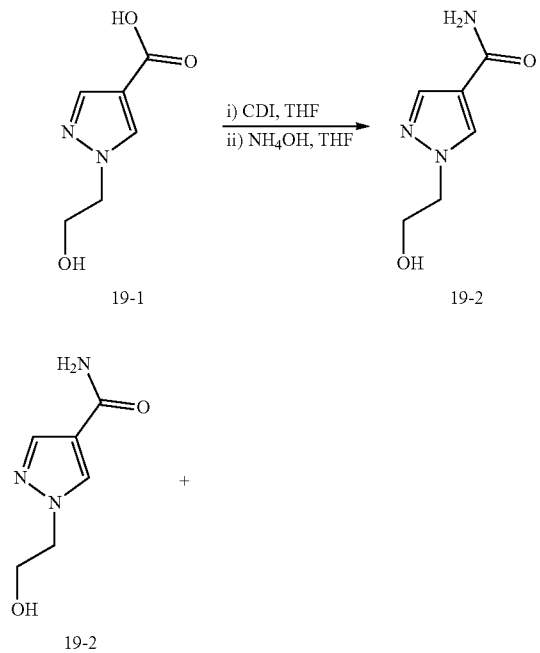

19-1

19-2

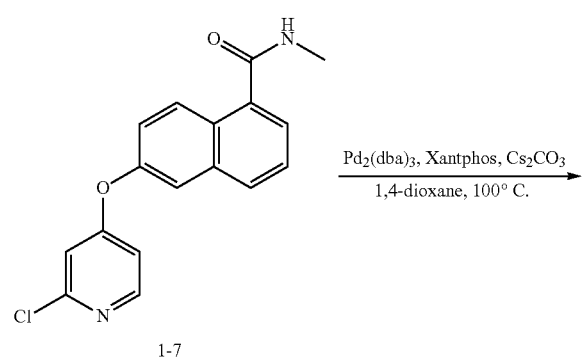

1-7

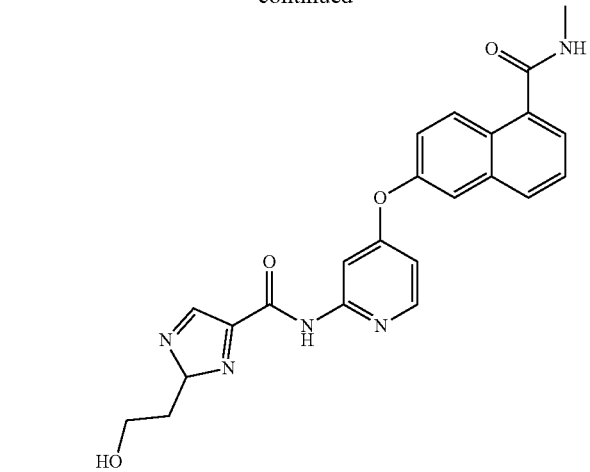

S19

The synthesis method of the compound 19-1 was conducted by referring to the method disclosed in WO2012040137.

Synthesis of Compound 19-2

1 eq of CDI [carbonyldiimidazole] was dissolved in dry THF [tetrahydrofuran], and the compound 19-1 was added thereto, and the mixture was reacted at 40° C. for 30 minutes, and then a solution of aqueous ammonia (20 eq) in tetrahydrofuran was added thereto, and the mixture was reacted at 30° C. overnight. After the reaction was completed, it was extracted with dichloromethane and water, and the organic phase was washed with saturated brine, dried over anhydrous sodium sulfate, and then directly added into the next step.

The synthesis of Compound S19 was the same as that of S1. The analysis data of S19: $^1$H NMR (300 MHz, DMSO-d6) δ 10.62 (s, 1H), 8.63-8.51 (m, 1H), 8.43 (s, 1H), 8.33 (d, J=9.3 Hz, 1H), 8.27 (d, J=5.7 Hz, 1H), 8.10 (s, 1H), 8.02 (dd, J=6.9, 2.0 Hz, 1H), 7.82 (dd, J=6.8, 1.9 Hz, 2H), 7.59 (d, J=7.0 Hz, 2H), 7.45 (dd, J=9.2, 2.5 Hz, 1H), 6.80 (dd, J=5.8, 2.0 Hz, 1H), 4.94 (t, J=5.3 Hz, 1H), 4.14 (t, J=5.2 Hz, 2H), 3.72 (q, J=5.4 Hz, 2H), 2.86 (d, J=4.4 Hz, 3H).

Preparation Example 20 Preparation of Compound S20

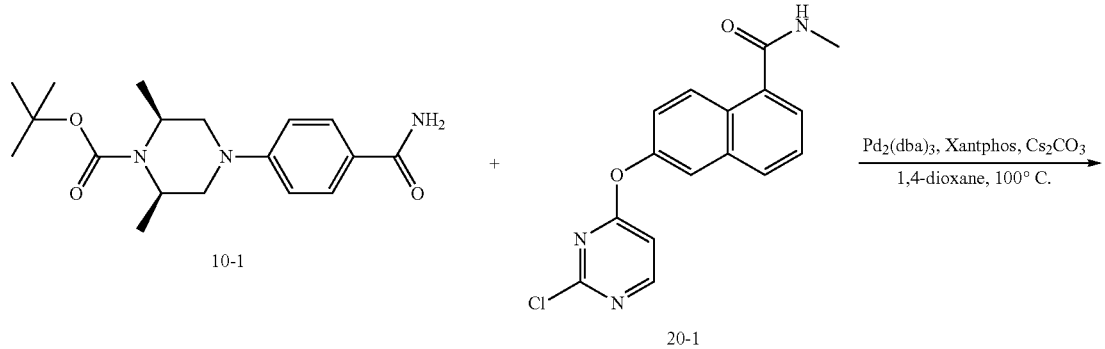

10-1

20-1

-continued
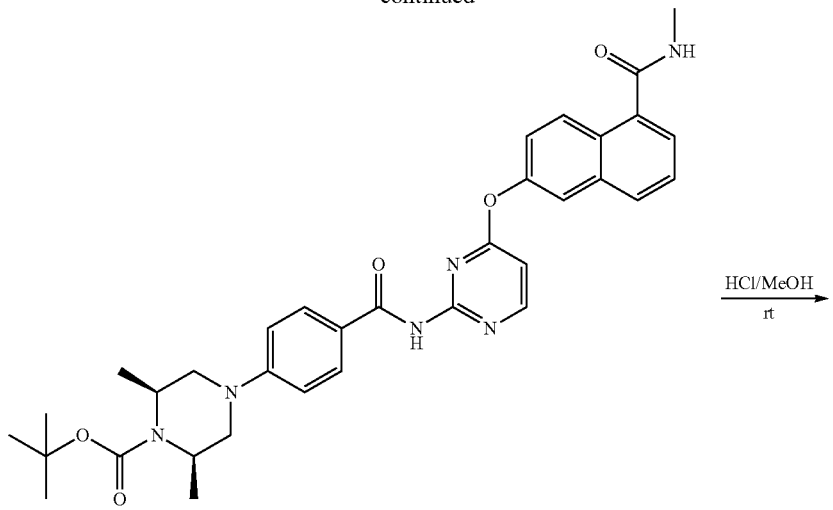
20-2
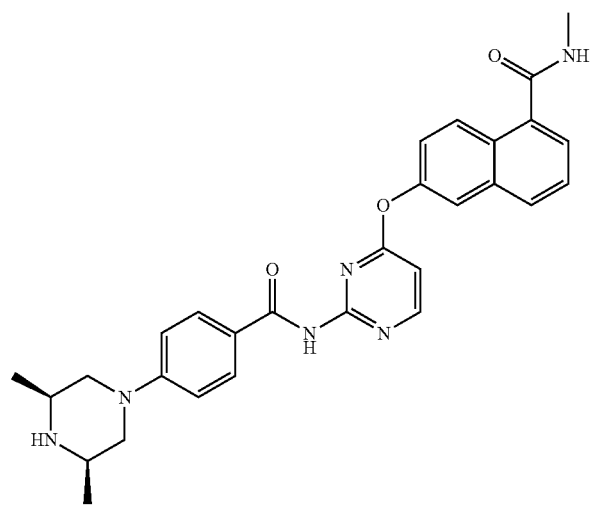
S20
The synthesis of Compound 20-1 was the same as that of 1-7.
The synthesis of Compound 20-2 was the same as that of S1.
The synthesis of Compound S20 was the same as that of S3. The analysis data of S20: $^1$H NMR (300 MHz, CDCl$_3$) δ 9.19 (s, 1H), 8.34 (d, J=5.3 Hz, 1H), 8.17 (d, J=9.2 Hz, 1H), 7.68 (d, J=8.1 Hz, 1H), 7.60 (d, J=8.3 Hz, 2H), 7.51 (s, 1H), 7.41 (dd, J=11.5, 5.6 Hz, 2H), 7.30 (d, J=7.8 Hz, 1H), 7.15 (d, J=9.0 Hz, 1H), 6.63 (d, J=8.5 Hz, 2H), 6.41 (d, J=5.6 Hz, 1H), 3.45 (d, J=12.3 Hz, 2H), 2.91-2.79 (m, 5H), 2.48-2.32 (m, 2H), 1.09 (d, J=6.2 Hz, 6H).
Preparation Example 21 Preparation of Compound S21
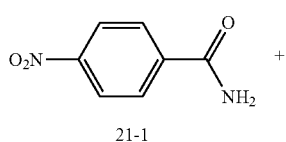
21-1

-continued

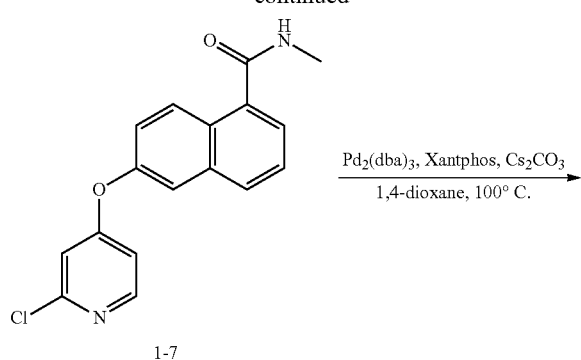

1-7

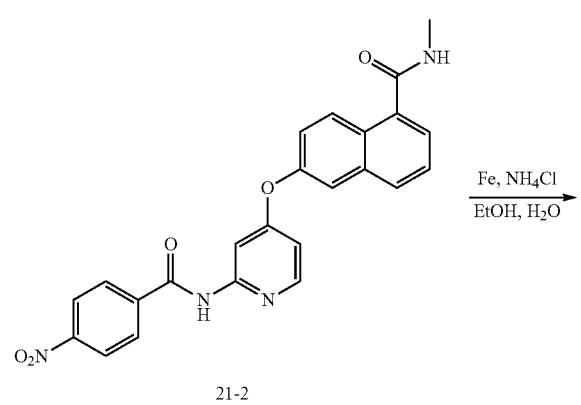

21-2

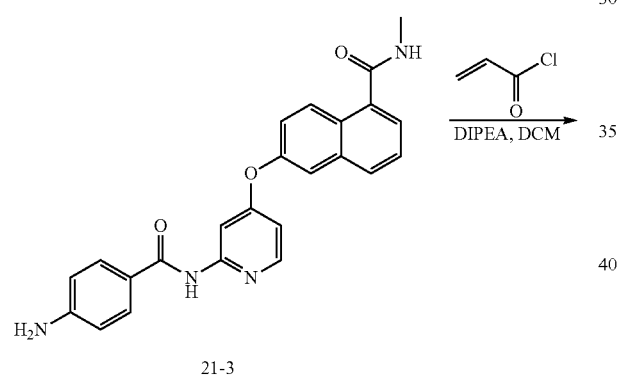

21-3

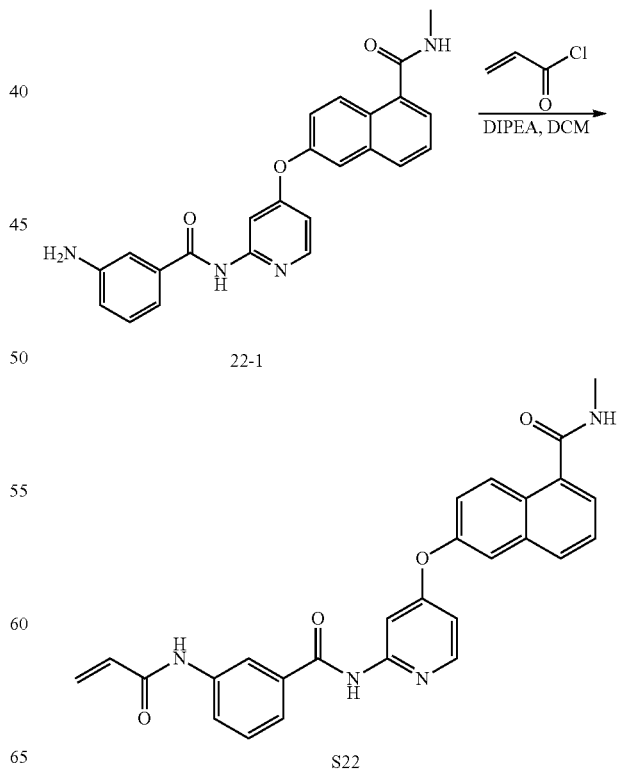

The synthesis of Compound 21-2 was the same as that of S1.

Synthesis of Compound 21-3

Compound 21-2 was dissolved in ethanol, an aqueous solution of ammonium chloride (10 eq) was added, then iron powder (5 eq) was added, and the mixture was reacted at 80° C. for 5 h. After the reaction was completed, the mixture was suction-filtrated, and the filtrate was evaporated to dryness. Then the mixture was extracted with dichloromethane and water, and the organic phase was washed with saturated brine, dried over anhydrous sodium sulfate. The mixture was applied to the column and eluted by DCM:MeOH=30:1 to provide compound 21-3.

The synthesis of compound S21:

Compound 21-3 was dissolved in dry dichloromethane under nitrogen, and acryloyl chloride (1.3 eq) was added under ice bath, and then DIPEA (2 eq) was added, and warmed to room temperature overnight after the addition is completed. After the reaction was completed, it was extracted with dichloromethane and water, and the organic phase was washed with saturated brine, dried over anhydrous sodium sulfate. The mixture was applied to the column and eluted by DCM:MeOH=30:1 to provide compound S21. The analysis data of S21: $^1$H NMR (300 MHz, CDCl$_3$) δ 8.26 (d, J=8.9 Hz, 1H), 8.05 (d, J=5.7 Hz, 2H), 7.85 (s, 1H), 7.76 (d, J=8.4 Hz, 1H), 7.65 (s, 1H), 7.49 (d, J=7.4 Hz, 3H), 7.36 (dt, J=16.1, 8.1 Hz, 2H), 7.25 (d, J=2.3 Hz, 1H), 6.64 (d, J=6.0 Hz, 1H), 6.37-6.15 (m, 2H), 5.65 (d, J=9.9 Hz, 1H), 2.95 (s, 3H).

Preparation Example 22 Preparation of Compound S22

The synthesis of Compound 22-1 was the same as that of 21-3.

The synthesis of Compound S22 was the same as that of S21, The analysis data of S22: ¹H NMR (300 MHz, DMSO) δ 10.76 (s, 1H), 10.41 (s, 1H), 8.53 (d, J=6.5 Hz, 1H), 8.39-8.28 (m, 2H), 8.09-8.00 (m, 1H), 7.97 (d, J=8.6 Hz, 2H), 7.88-7.80 (m, 2H), 7.75 (d, J=8.8 Hz, 2H), 7.59 (d, J=7.0 Hz, 2H), 6.84 (d, J=5.5 Hz, 1H), 6.46 (dd, J=17.4, 10.3 Hz, 1H), 6.29 (d, J=17.3 Hz, 1H), 5.80 (d, J=12.6 Hz, 1H), 2.86 (d, J=4.5 Hz, 3H).

Preparation Example 23 Preparation of Compound S23

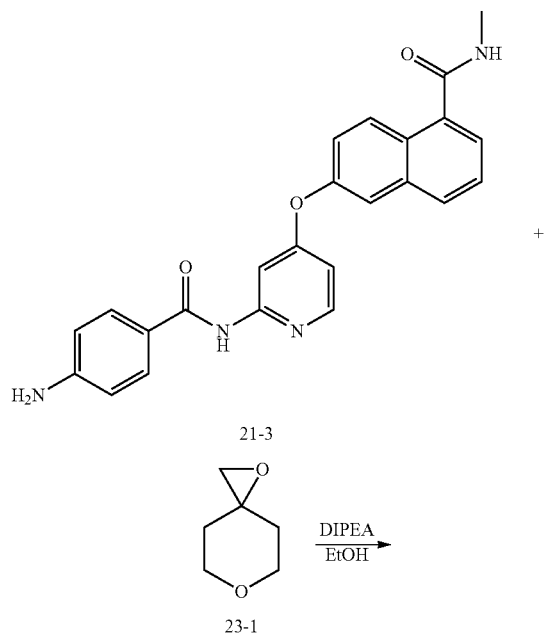

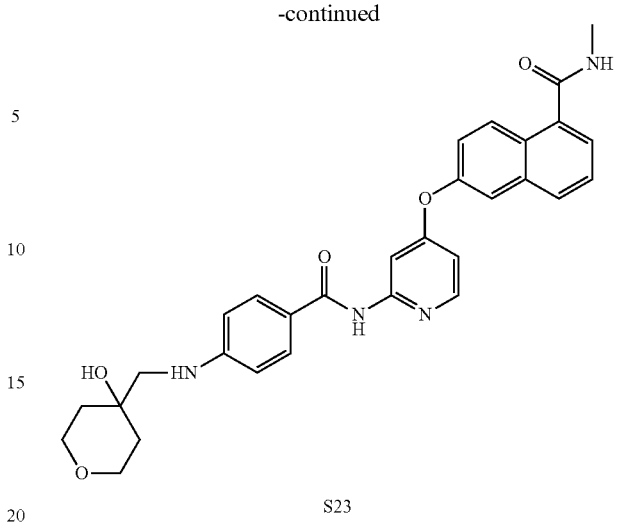

The synthesis method of the compound 23-1 was conducted by referring to the method disclosed in WO2012040137.

The synthesis of compound S23:

Compound 21-3 was dissolved in ethanol, compound 23-1 (2 eq) was added, and then DIPEA (2 eq) was added, then reacted at 75° C. for two days. After the reaction was completed, the reaction mixture was evaporated to dryness, and extracted with dichloromethane and water, and the organic phase was washed with saturated brine, dried over anhydrous sodium sulfate. The mixture was applied to the column and eluted by DCM:MeOH=20:1 to provide compound S23. The analysis data of S23: ¹H NMR (300 MHz, CDCl₃) δ 8.67 (s, 1H), 8.34 (d, J=9.2 Hz, 1H), 8.11 (d, J=5.8 Hz, 1H), 7.97 (d, J=2.3 Hz, 1H), 7.82 (d, J=8.1 Hz, 1H), 7.62 (d, J=8.4 Hz, 2H), 7.56-7.49 (m, 2H), 7.43 (t, J=7.6 Hz, 1H), 7.31 (dd, J=9.1, 2.4 Hz, 1H), 6.65 (dd, J=5.8, 2.3 Hz, 1H), 6.49 (d, J=8.4 Hz, 2H), 6.43 (d, J=5.3 Hz, 1H), 4.54 (t, J=5.9 Hz, 1H), 3.76-3.64 (m, 4H), 3.06 (dd, J=10.8, 5.2 Hz, 5H), 1.82 (s, 1H), 1.73-1.54 (m, 4H).

Preparation Example 24 Preparation of Compound S24

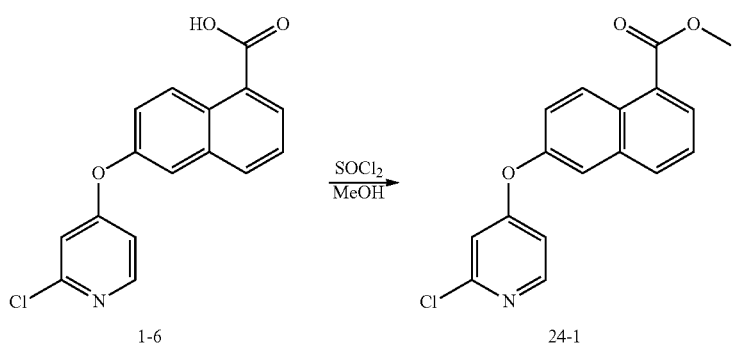

US 11,834,432 B2

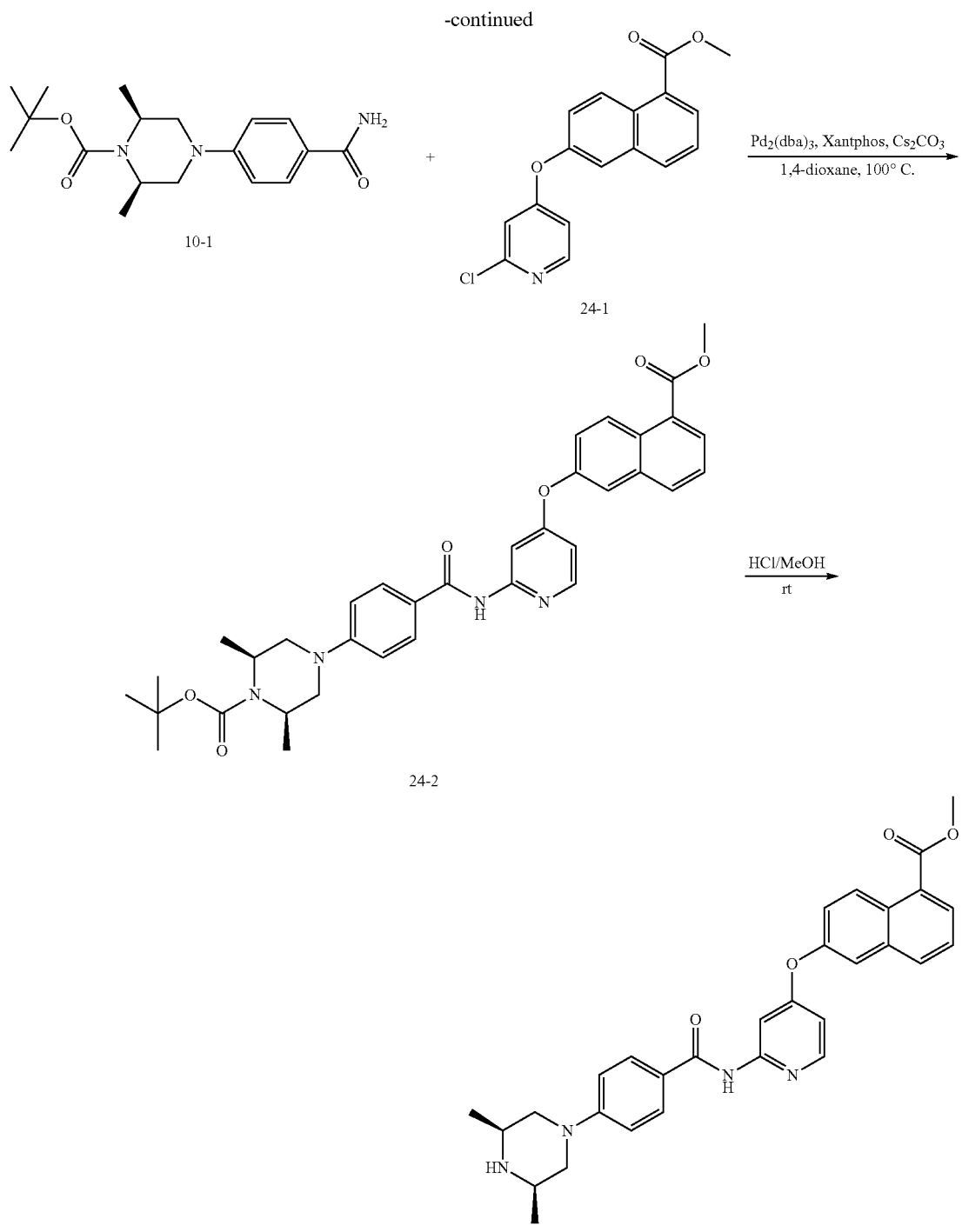

Synthesis of Compound 24-1

Compound 1-6 was dissolved in methanol, and thionyl chloride (1.5 eq) was added under ice-bath, and the mixture was warmed to 60° C. to react for 5 h. After the reaction was completed, the reaction mixture was evaporated to dryness and extracted with DCM and saturated sodium bicarbonate solution, washed with saturated brine, dried over anhydrous sodium sulfate and directly used in the next step.

The synthesis of Compound 24-2 was the same as that of S1.

The synthesis of Compound S24 was the same as that of S3. The analysis data of S24: $^1$H NMR (300 MHz, CDCl$_3$) δ 8.71 (s, 1H), 8.45 (d, J=9.2 Hz, 1H), 8.21 (d, J=5.7 Hz, 1H), 8.09 (s, 1H), 7.92 (d, J=8.1 Hz, 1H), 7.81 (d, J=8.6 Hz, 2H), 7.63 (d, J=5.9 Hz, 2H), 7.51 (t, J=7.6 Hz, 1H), 7.47-7.40 (m, 1H), 6.95 (d, J=8.7 Hz, 2H), 6.85-6.78 (m, 1H), 6.13 (d, J=3.6 Hz, 1H), 3.91 (s, 3H), 3.65 (d, J=11.1 Hz, 2H), 2.94 (td, J=9.1, 4.4 Hz, 2H), 2.39 (t, J=11.2 Hz, 2H), 1.14 (d, J=6.2 Hz, 6H).

II. EXPERIMENTAL EXAMPLE

1. Preliminary Evaluation Inhibition on Receptor Tyrosine Kinase FGFR1 Activity of Compound Experimental method:

1. Enzyme reaction substrate μPoly(Glu,Tyr)4:1 was diluted with PBS without potassium ion (10 mM sodium phosphate buffer, 150 mM NaCl, pH7.2-7.4) to 201 μg/mL, an enzyme plate was coated at 125 μL/well, and incubated at 37° C. for 12-16 hours. The liquid from the well was discarded. The plate was washed for three times with T-PBS (0.1% Tween-20 in potassium-free PBS, 200 μL/well), 5 minutes for each time. The elisa plate was dried in 37° C. dryer for 1-2 hours.

2. 49 μL of ATP solution diluted in reaction buffer (50 mM HEPES pH 7.4, 50 mM $MgCl_2$, 0.5 mM $MnCl_2$, 0.2 mM $Na_3VO_4$, 1 mM DTT) was added into each well, and 1 μL of the test compound was added to each well, and then 50 μL of FGFR1 kinase domain recombinant protein diluted in reaction buffer was added to initiate the reaction, and two control wells without ATP were required for each experiment. The reaction was performed on a Shaker (100 rpm) at 37° C. for 1 hour. The liquid from the well was discarded, and the plate was washed with T-PBS for three times.

3. The antibody PY99 dilution (antibody diluted 1:500 in T-PBS with BSA 5 mg/mL) was added at 100 μL/well, and shaken for 0.5 hours on a 37° C. shaker. The liquid from the well was discarded, and the plate was washed with T-PBS for three times.

4. The horseradish peroxidase-labeled goat anti-mouse second antibody dilution (antibody diluted 1:2000 in T-PBS with BSA 5 mg/mL) was added at 100 μL/well, and shaken for 0.5 hours on a 37° C. shaker. The liquid from the well was discarded, and the plate was washed with T-PBS for three times.

5. 2 mg/mL OPD coloration solution (diluted with 0.1 M citric acid-sodium citrate buffer containing 0.03% $H_2O_2$ (pH=5.4)) was added at 100 μL/well, and reacted for 1-10 minutes at 25° C. in darkness.

6. The reaction was quenched with 50 μL/well of 2M $H_2SO_4$, and the plate was read using a tunable microplate microplate reader VERSAmax at 490 nm.

7. Analysis of results $$\text{inhibition rate (\%)} = \left(1 - \frac{OD \text{ of the compound} - OD \text{ of the control well (without } ATP)}{OD \text{ of the negative control} - OD \text{ of the control well (without } ATP)}\right) \times 100\%$$

The $IC_{50}$ values were obtained by four-parameter regression analysis using the software supplied with the microplate reader.

The inhibition level on receptor tyrosine kinase FGFR1 activity of a compound is shown in the following able:

| Compound | Inhibition ratio (%) @ 0.1 μM | $IC_{50}$ (μM) | Compound | Inhibition ratio (%) @ 0.1 μM | $IC_{50}$ (μM) |
|---|---|---|---|---|---|
| S1 | 72 | <0.1 | S2 | 80 | <0.1 |
| S3 | 90 | <0.01 | S4 | 74 | <0.01 |
| S5 | 87 | <0.01 | S6 | 84 | <0.01 |
| S7 | 91 | <0.01 | S8 | 93 | <0.01 |
| S9 | 95 | <0.01 | S10 | 94 | <0.01 |
| S11 | 89 | <0.01 | S12 | 44 | <1 |
| S13 | 23 | >1 | S14 | 40 | <1 |
| S15 | 71 | <0.1 | S16 | 58 | <0.1 |
| S17 | 59 | <0.1 | S18 | 65 | <0.1 |
| S19 | 86 | <0.01 | S20 | 94 | <0.01 |
| S21 | 78 | <0.1 | S22 | 84 | <0.1 |
| S23 | 86 | <0.01 | S24 | 87 | <0.01 |

Test results at molecular level show that these compounds have strong inhibitory activities on FGFR, and half of the compounds have an $IC_{50}$ less than 10 nM.

2. Evaluation of Activity on Receptor Tyrosine Kinase FGFR Cells of Compound Experimental method:

The inhibitory effect on proliferation of SNU16 cells of a compound was examined by CCK-8 Cell Counting Kit (Dojindo). The steps are as follows: SNUI 6 cells at Logarithmic growth phase were seeded in a 96-well culture plate at appropriate density, 90 ul for each well. After cultured overnight, different concentrations of drugs were added and treated for 72 h, while solvent control well was set (negative control). After 72 h, the influence of the compound on the proliferation of cells was observed by CCK-8 cell counting kit (Dojindo). 10 μL of CCK-8 reagent was added to each well. After incubated for 2-4 hours in a 37° C. incubator, the plate was read with SpectraMax 190 microplate reader at wavelength 450 nm.

The inhibition rate (%) of the compound on tumor cell growth was calculated using the following formula:

Inhibition rate (%)=(OD of control well-OD of drug well)/OD of control well×100%.

The $IC_{50}$ values were obtained by four-parameter regression analysis using the software supplied with the microplate reader.

The inhibitory rates to the proliferation of SNU16 cells of the compounds are as follows:

| Concentration (nM) Number of the sample | 1000 | 100 | 10 | $IC_{50}$ (nM) |
|---|---|---|---|---|
| | Inhibition ratio (%) | | | |
| S4 | 59.0 | 61.0 | 55.3 | 29.2 |
|  | 60.4 | 60.5 | 48.3 |  |
| S5 | 57.8 | 60.1 | 60.4 | 13.8 |
|  | 58.8 | 61.0 | 61.3 |  |
| S6 | 59.6 | 63.5 | 45.1 | 15.9 |
|  | 63.1 | 64.1 | 43.3 |  |
| S7 | 60.5 | 53.3 | 30.1 | $NT^a$ |
|  | 62.5 | 52.6 | 31.9 |  |
| S8 | 48.1 | 36.3 | 23.2 | $NT^a$ |
|  | 45.6 | 36.3 | 24.3 |  |
| S9 | 73.3 | 73.2 | 70.9 | 13.8 |
|  | 71.1 | 71.0 | 67.6 |  |
| S10 | 59.7 | 62.1 | 59.6 | 6.1 |
|  | 60.9 | 63.4 | 60.8 |  |
| S16 | 61.6 | 55.3 | 26.4 | $NT^a$ |
|  | 63.1 | 54.8 | 26.7 |  |
| S21 | 43.5 | 28.5 | 27.8 | $NT^a$ |
|  | 38.9 | 25.9 | 24.6 |  |

$NT^a$ = not tested

Results of inhibitory test on the proliferation of SNU16 cells show that these compounds have strong inhibitory activities on FGFR, and some of the compounds have an $IC_{50}$ less than 10 nM.

3. Inhibition Experiment on FGFR2 and Phosphorylation of Downstream Signaling Molecules of the Compound The results were shown in the figure. The results show that the compound is capable of targeting FGFR at the cellular level and inhibiting signal transduction of the corresponding downstream signaling pathway.

4. In Vitro Screening Test on Tyrosine Kinase Activity Inhibition

Screening method: Enzyme-linked immunosorbent assay (ELISA)

tyrosine kinase: Enzyme spectrum

Time of action: 1 h

TABLE 1

Tyrosine kinase inhibition ratio of the compound (%)

| No. of compound (nM) | Inhibition ratio (%) | | | | | |
|---|---|---|---|---|---|---|
| | c-Met | VEGFR-1 | VEGFR-2 | EGFR | ErbB2 | ErbB4 |
| S10(1000 nM) | 29.5 | 100.0 | 98.7 | 11.3 | 22.2 | 7.0 |
| S10(10 nM) | 11.2 | 75.6 | 90.4 | 9.6 | 17.4 | 2.0 |

TABLE 2

Tyrosine kinase inhibition ratio of the compound (%)

| No. of compound (nM) | Inhibition ratio (%) | | | | | | |
|---|---|---|---|---|---|---|---|
| | c-Src | ABL | EPH-A2 | IGF1R | PDGFR-α | PDGFR-β | RET |
| S10 (1000 nM) | 43.6 | 28.8 | 7.7 | 11.0 | 87.1 | 87.8 | 90.5 |
| S10 (10 nM) | 20.3 | 17.5 | 4.2 | 23.5 | 50.2 | 56.4 | 13.2 |

5. Experimental study on pharmacokinetics of some compounds in rats

1) Dosing Regimen

Seven SD rats, male, weighing 200-220 g, were randomly divided into two groups, 4 or 3 in each group. Compound S10 was administered by intragastric or intravenous administration. The specific arrangement is shown in the following table:

| Group | number of animal | Compound | Route of administration | dosage (mg/kg) | Dose volume (ml/kg) |
|---|---|---|---|---|---|
| 1 | 4 | S10 | gavage | 10 | 10 |
| 2 | 3 | S10 | vein | 5 | 5 |

Rats were fasted for 12 h before test, and had access to water ad libitum. The rats were uniformly fed 2 h after administration of.

Blood sample time point and sample preparation:

intragastric administration: 0.25, 0.5, 1.0, 2.0, 4.0, 6.0, 8.0 and 24 h after administration;

intravenous administration: 5 min, 0.25, 0.5, 1.0, 2.0, 4.0, 6.0, 8.0 and 24 h after administration;

0.3 mL of venous blood was collected at the above time points via the rat eye vein venous plexus, placed in a heparinized test tube, and centrifuged at 11000 rpm for 5 min, and plasma was separated and frozen in a −20° C. refrigerator.

2) Sample Testing and Data Analysis

S10 in rat plasma was determined by LC/MS/MS.

The pharmacokinetic parameters after administration were calculated by a non-compartmental model of WinNonlin 6.3 software (Pharsight, USA).

The peak concentration $C_{max}$ and the peak time $T_{max}$ are measured values; The area under the curve of the drug-time $AUC_{0-t}$ value: calculated by the trapezoidal method; $AUC_{0-\infty}=AUC_{0-t}+C_t/k_e$, $C_t$ is the blood concentration of drug at the last measurable time point;

$k_e$ is the elimination rate constant;

Elimination half-life $t_{1/2}=0.693/k_e$;

Clearance rate $CL=D/AUC_{0-\infty}$;

Volume of steady state distribution $V_{ss}=CL\times MRT$;

Absolute bioavailability $F=(AUC_{intragastric}\times D_{intravenous})/(AUC_{intravenous}\times D_{intragastric})\times 100\%$.

3) Test Results

| | Intragastric 10 mg/kg | | | | | Intravenous 5 mg/kg | | |
|---|---|---|---|---|---|---|---|---|
| Compound | $T_{max}$ (h) | $C_{max}$ (ng/mL) | $AUC_{0-t}$ (ng·h/mL) | $t_{1/2}$(h) | F(%) | CL (L/h/kg) | $V_{ss}$ (L/kg) | $t_{1/2}$ (h) |
| S10 | 4.5 | 399 | 3431 | 3.55 | 79.6 | 2.45 | 11.3 | 3.69 |

6. Inhibitory Effects of Compound on the Growth of Subcutaneously Transplanted Tumor in Human Lung Cancer NCI-H1581 Nude Mice 1) Cell Strain Human lung cancer NCI-H1581 cell strain was preserved in our laboratory. The cell strain was inoculated in the right axilla of the nude mice, and the amount of cells inoculated was $5\times 10^6$/mouse to form transplanted tumor, which was directly inoculated and used.

2) Experimental Method

The tumor tissue in the prosperous growth period was cut into 1.5 mm³, and inoculated subcutaneously in the right axilla of the nude mice under aseptic conditions. The diameter of the transplanted tumor in the nude mice was measured with a vernier caliper, and the animals were randomly grouped when the average volume of tumors was about 150-160 mm³. S10 groups (10 mg/kg, 5 mg/kg, and 2.5 mg/kg) were orally administered once a day for two weeks. The solvent control group was given an equal amount of water for injection. The diameter of the transplanted tumor was measured twice a week during the entire experiment, and the body weight of the mice was also weighed. The calculation formula of tumor volume (TV) is: $TV=1/2\times a\times b^2$, where a and b respectively represent the length and width of the tumor. The relative tumor volume (RTV) was calculated based on the measured results and the formula was: $RTV=V_t/V_0$, where $V_0$ is the tumor volume measured at grouping and dosing $(d_0)$, and $V_t$ is the tumor volume at each measurement. The evaluation index of anti-tumor activity is relative tumor proliferation rate T/C (%), and the formula is as follows: $T/C (\%)=(T_{RTV}/C_{RTV})\times 100\%$, $T_{RTV}$: treatment group RTV; $C_{RTV}$: negative control group RTV;

3) Results

Experimental results are shown in the following table. S10 groups (10 mg/kg, 5 mg/kg, and 2.5 mg/kg) were orally administered once a day for two weeks, which significantly inhibited the growth of subcutaneously transplanted tumors in human lung cancer NCI-H1581 nude mice. On the 14th day, the obtained tumor inhibition rate T/C percentages were 10.03%, 17.18% and 40.19%, respectively. During the experiment, the animals in each group were in good condition and there was no mice died.

Therapeutic effects of compound S10 on transplanted tumor in human lung cancer NCI-H158_1 nude mice.

| Group | Dosage, method of administration | | Number of animal | | Body weight (g) | | TV (mm³, mean SD) | | RTV (mean SD) | T/C (%) |
|---|---|---|---|---|---|---|---|---|---|---|
| | | | $d_0$ | $d_{14}$ | $d_0$ | $d_{14}$ | $d_0$ | $d_{14}$ | | |
| Solvent control | 0.4 ml/20 g qd/14 | po | 12 | 12 | 19.8 | 25.5 | 157 ± 64 | 3122 ± 1136 | 20.81 ± 6.53 | |
| S10 | 10 mg/kg qd/14 | po | 6 | 6 | 19.9 | 23.0 | 155 ± 45 | 338 ± 223 | 2.09 ± 0.77* | 10.03 |
| | 5 mg/kg qd/14 | po | 6 | 6 | 19.0 | 21.5 | 154 ± 53 | 524 ± 122 | 3.57 ± 0.91* | 17.18 |
| | 2.5 mg/kg qd/14 | po | 6 | 6 | 19.8 | 21.8 | 157 ± 43 | 1287 ± 412 | 8.36 ± 2.17* | 40.19 |

7. Inhibitory Effects of Compound S10 on the Growth of Subcutaneously Transplanted Tumor in Human Gastric Cancer SNU-16 Nude Mice 1) Cell Strain The human gastric cancer SNU-16 cell strain was preserved in our laboratory. The cell strain was inoculated in the right axilla of the nude mice, and the amount of cells inoculated was 5×10⁶/mouse to form a transplanted tumor, which was passaged in vivo in nude mice for 2 generations and then used.

2) Experimental Method

The tumor tissue in the prosperous growth period was cut into 1.5 mm³, and inoculated subcutaneously in the right axilla of the nude mice under aseptic conditions. The diameter of the transplanted tumor in the nude mice was measured by a vernier caliper, and the animals were randomly grouped when the average volume of tumors was about 100 mm³. S10 groups (30 mg/kg and 10 mg/kg) were orally administered once a day for 21 days; AZD4547 group (10 mg/kg) was administered orally once a day for 21 days; solvent control group was given the same amount of water for injection. The diameter of the transplanted tumor was measured twice a week during the entire experiment, and the body weight of the mice was also weighed. The calculation formula of tumor volume (TV) is: TV=1/2×a×b², where a and b respectively represent the length and width of the tumor. The relative tumor volume (RTV) was calculated based on the measured results and the formula was: RTV=$V_t$/$VN_0$, where $V_0$ is the tumor volume measured at grouping and dosing ($d_0$), and $V_t$ is the tumor volume at each measurement. The evaluation index of anti-tumor activity is relative tumor proliferation rate T/C (%), and the formula is as follows: T/C (%)=($T_{RTV}$/$C_{RTV}$)×100%, $T_{RTV}$: treatment group RTV; $C_{RTV}$: negative control group RTV.

3) Results

The experimental results are listed in the following table. S10 groups (30 mg/kg, and 10 mg/kg) were orally administered once a day for 21 days, which significantly inhibited the growth of subcutaneously transplanted tumors in human gastric cancer SNU-16 nude mice. On the 21th day, the obtained T/C percentages were 8.67% and 25.35%, respectively. The positive control AZD4547 group (10 mg/kg) was orally administered once a day for 21 days, in which the growth of subcutaneously transplanted tumors in human gastric cancer SNU-16 nude mice was partially inhibited. On the 21th day, the obtained T/C percentages of the group was 59.80%. During the experiment, only the average weight of mice in the S10 group (30 mg/kg) was decreased, but the mice were still in good condition and no mice died. Inhibitory effect of compound S10 on the growth of subcutaneously transplanted tumor in human gastric cancer SNU-16 nude mice was significantly improved over compound AZD4547.

Therapeutic effect of S10 on transplanted tumor in human gastric cancer SNU-16 nude mice.

| Group | Dosage, method of administration | | Number of animal | | Body weight (g) | | TV (mm³, mean ± SD) | | RTV (mean ± SD) | T/C (%) |
|---|---|---|---|---|---|---|---|---|---|---|
| | | | $d_0$ | $d_{21}$ | $d_0$ | $d_{21}$ | $d_0$ | $d_{21}$ | | |
| Solvent control | 0.2 ml/mouse qd/21 | po | 12 | 12 | 20.6 | 21.0 | 101 ± 30 | 1319 ± 386 | 13.73 ± 4.20 | |
| AZD4547 | 10 mg/kg qd/21 | po | 6 | 6 | 20.1 | 22.4 | 103 ± 18 | 790 ± 247 | 8.21 ± 3.91* | 59.80 |
| S10 | 30 mg/kg qd/21 | po | 6 | 6 | 21.2 | 17.0 | 106 ± 22 | 125 ± 47 | 1.19 ± 0.38* | 8.67 |
| | 10 mg/kg qd/21 | po | 6 | 6 | 19.9 | 21.4 | 106 ± 33 | 322 ± 107 | 3.48 ± 2.29* | 25.35 |

8. When Compared with E7090 (FGFR Inhibitor, Clinical Phase I), which Also has an Aminopyridine Core while the Side Chain is Indole, Inhibitory Effect of Compound S10 on the Growth of Transplanted Tumor in Human Lung Cancer NCI-H1581 Nude Mice was More Obvious, and the Comparison Results are Shown in the Table Below.

| Number of compound | Dosage (mg/Kg) | Relative tumor proliferation rate T/C (%) |
|---|---|---|
| S10 | 2.5 | 40 |
|  | 5 | 17 |
|  | 10 | 10 |
| E7090 | 6.25 | 46 |
|  | 12.5 | 21 |
|  | 25 | 13 |
|  | 50 | 8 |

T/C is the relative tumor proliferation rate, and the smaller the value, the higher the antitumor activity. When the dose of Compound S10 was 2.5 mg/Kg, the T/C value was 40%, and when the dose of compound E7090 was 6.25 mg/Kg, the T/C value was 46%, which indicated that compound E7090 need to be administered in a dose of 2 to 3 times that of S10 to achieve the same anti-tumor inhibition effect. Comparing with other results, it also showed that the inhibitory effect of compound S10 on the growth of transplanted tumor in human lung cancer NCI-H1581 nude mice was significantly higher than that of E7090 compound.

9. Compared with E7090, the Inhibitory Effect of Compound S10 on the Growth of Transplanted Tumor in Human Gastric Cancer SNU-16 Nude Mice was More Significant, and the Comparison Results are Shown in the Following Table

| Number of compound | Dosage (mg/Kg) | Relative tumor proliferation rate T/C (%) |
|---|---|---|
| S10 | 10 | 25 |
|  | 30 | 9 |
| E7090 | 6.25 | 49 |
|  | 12.5 | 26 |
|  | 25 | 17 |
|  | 50 | 18 |

When the dose of compound S10 was 30 mg/Kg, the relative tumor proliferation rate T/C value was 9%, while the relative tumor proliferation rate T/C value was 18% when the compound E7090 dose was 50 mg/Kg. The comparison results demonstrated that in the human gastric cancer SNU-16 nude mouse xenograft model, the dose of compound S10 was significantly lower than that of E7090 for achieving the same anti-tumor activity in vivo.

Thus, the newly designed compounds have excellent enzyme inhibitory activity against FGFR and significant inhibitory activity against FGFR-dependent cell proliferation, which is able to target FGFR at the cellular level and inhibit signal transduction of the corresponding downstream signaling pathway. The representative compound S10 also has good pharmacokinetic properties, and is highly sensitive to FGFR-dependent gastric cancer and lung cancer, which exhibit a significantly higher inhibitory effects on the growth of human lung cancer NCI-H1581 nude mice xenografts and the growth of human gastric cancer SNU-16 nude mice xenografts as compared with the compound E7090. Therefore, such compounds have good prospects for research and development as novel FGFR inhibitors.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of the following formula I, or pharmaceutically acceptable salts thereof:

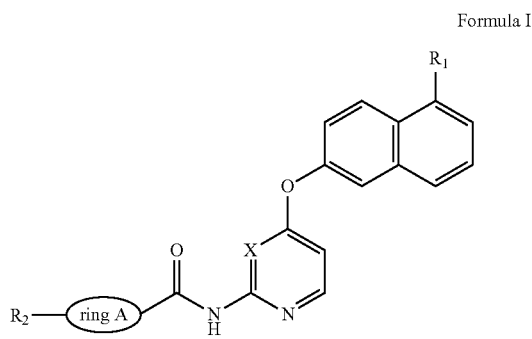

Formula I wherein:

X is selected from the group consisting of CH and N;

Ring A may be selected from the group consisting of a substituted or unsubstituted 6-10 membered aryl, substituted or unsubstituted 5-12 membered heteroaryl, wherein "substituted" means that one or more hydrogen atoms on a group are substituted by a substituent selected from the group consisting of a C1-C8 alkyl, C1-C8 alkoxy, C1-C8 alkylamino, halogen, halogenated C1-C8 alkyl;

$R_1$ is selected from —CONHR$_3$, —COOR$_3$;

$R_2$ is selected from the group consisting of a substituted or unsubstituted C1-C8 alkyl, substituted or unsubstituted C1-C8 alkoxy, substituted or unsubstituted 4-10 membered heterocyclic group, substituted or unsubstituted amino, substituted or unsubstituted C1-C8 alkylamino, —NHCOR$_3$; wherein the substituent is further substituted by one or more substituents selected from the group consisting of a C1-C8 alkyl, hydroxy, hydroxy C1-C8 alkyl, —COOR$_3$, amino-substituted C3-C10 cycloalkyl group, 4-10 membered heterocycloalkyl which is unsubstituted or substituted by one or more halogen atoms, hydroxyl or C1-C8 alkyl;

$R_3$ is hydrogen or C1-C8 alkyl.

2. The compound of claim 1, wherein, in the formula I compound, $R_2$ is selected from the group consisting of a substituted or unsubstituted C1-C4 alkyl, substituted or unsubstituted C1-C4 alkoxy, substituted or unsubstituted 5-6 membered heterocyclic group, substituted or unsubstituted amino, substituted or unsubstituted C1-C4 alkylamino, —NHCOR$_3$;

wherein the substituent group is further substituted by one or more substituents selected from the group consisting of a C1-C8 alkyl, hydroxy, hydroxy C1-C8 alkyl, —COOR$_3$, amino-substituted C3-C10 cycloalkyl, 4-10 membered heterocycloalkyl which is unsubstituted or substituted by one or more halogen atoms, hydroxyl or C1-C8 alkyl.

3. The compound of claim 1, wherein, in the formula I compound, ring A is selected from a substituted or unsubstituted 6-10 membered aryl or substituted or unsubstituted 5-6 membered heteroaryl.

4. The compound of claim 1, wherein, in the formula I compound, ring A is a substituted or unsubstituted group selected from the group consisting of benzene ring, naphthalene ring, pyridine ring, pyrazine ring, thiophene ring, furan ring, imidazole ring, pyrrole ring, oxazole ring, thiazole ring, pyrazole ring, indole ring, pyrimidine ring, benzofuran ring, benzo thiazole ring, benzimidazole ring, quinoline ring, isoquinoline ring.

5. The compound of claim 1, wherein $R_3$ is hydrogen or C1-C4 alkyl.

6. The compound of claim 1, wherein, in the formula I compound, ring A is selected from the group consisting of a substituted or unsubstituted benzene ring, substituted or unsubstituted thiazole ring, substituted or unsubstituted oxazole ring, substituted or unsubstituted pyrimidine ring.

7. The compound of claim 1, wherein, in the formula I compound, $R_3$ is hydrogen or methyl.

8. The compound of claim 1, wherein the compound is selected from the following group:

| Compound | Structure |
|---|---|
| S1 | 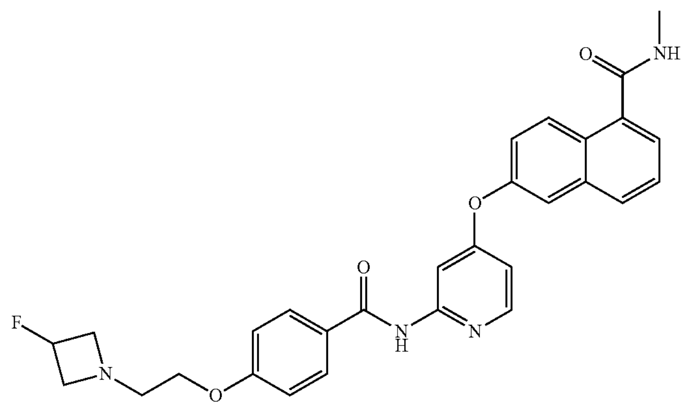 [SMILES: CNC(=O)c1cccc2cc(Oc3ccnc(NC(=O)c4ccc(OCCN5CC(F)C5)cc4)c3)ccc12] |
| S2 | 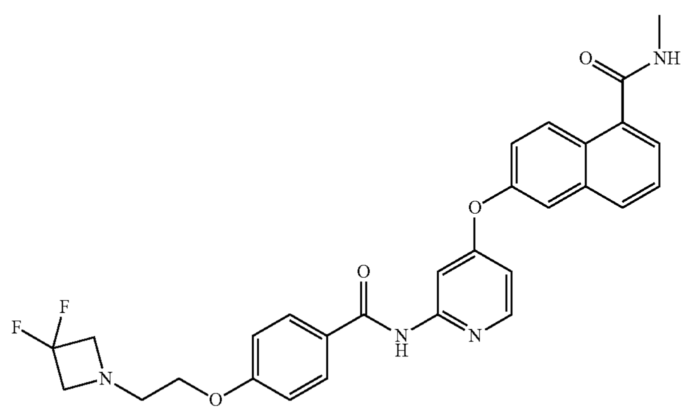 [SMILES: CNC(=O)c1cccc2cc(Oc3ccnc(NC(=O)c4ccc(OCCN5CC(F)(F)C5)cc4)c3)ccc12] |
| S3 | 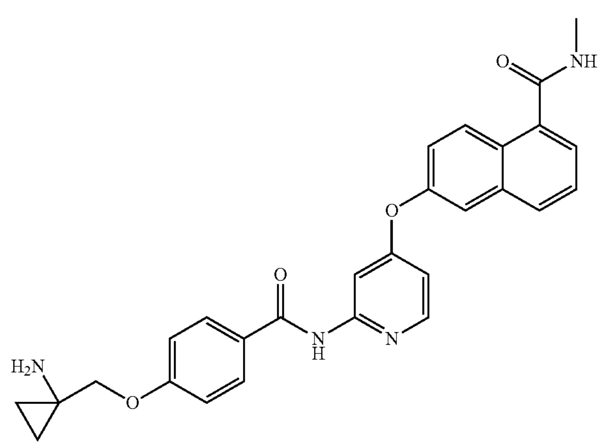 [SMILES: CNC(=O)c1cccc2cc(Oc3ccnc(NC(=O)c4ccc(OCC5(N)CC5)cc4)c3)ccc12] |

-continued

| Compound | Structure |
|---|---|
| S4 | 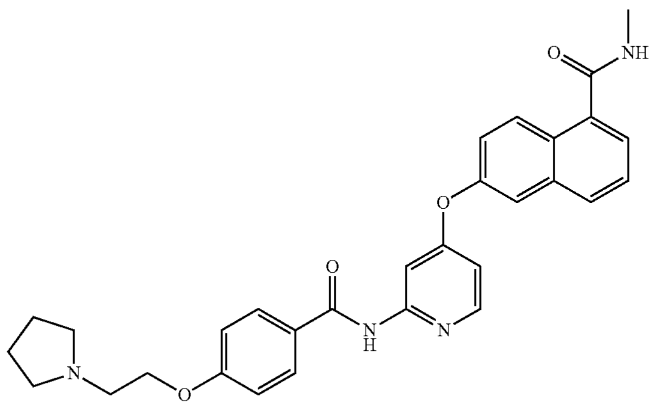 [SMILES: CNC(=O)c1cccc2cc(Oc3ccnc(NC(=O)c4ccc(OCCN5CCCC5)cc4)c3)ccc12] |
| S5 | 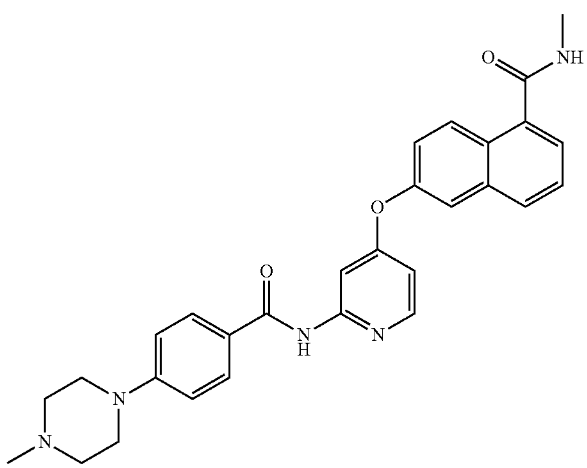 |
| S6 | 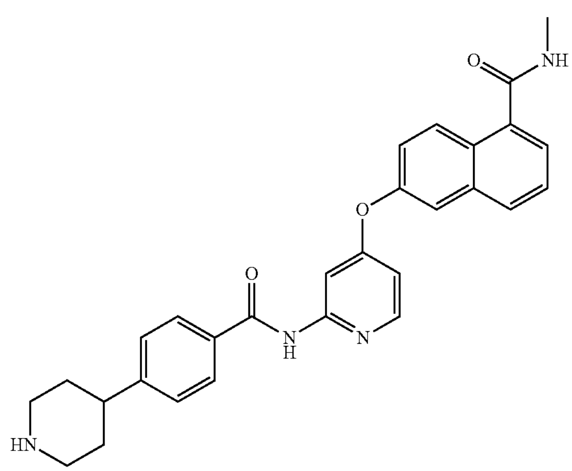 [SMILES: CNC(=O)c1cccc2cc(Oc3ccnc(NC(=O)c4ccc(C5CCNCC5)cc4)c3)ccc12] |

-continued
| Compound | Structure |
|---|---|
| S7 | 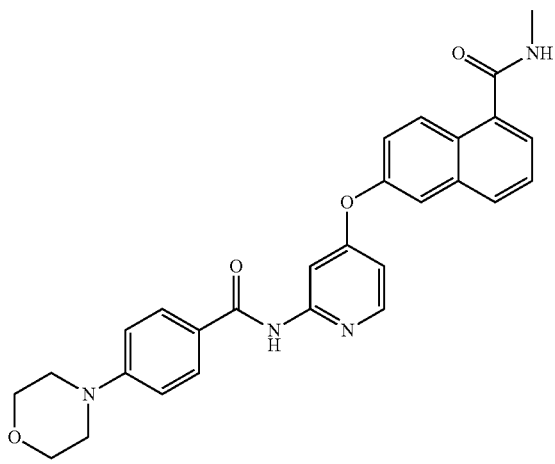 [SMILES: CNC(=O)c1cccc2cc(Oc3ccnc(NC(=O)c4ccc(N5CCOCC5)cc4)c3)ccc12] |
| S8 | 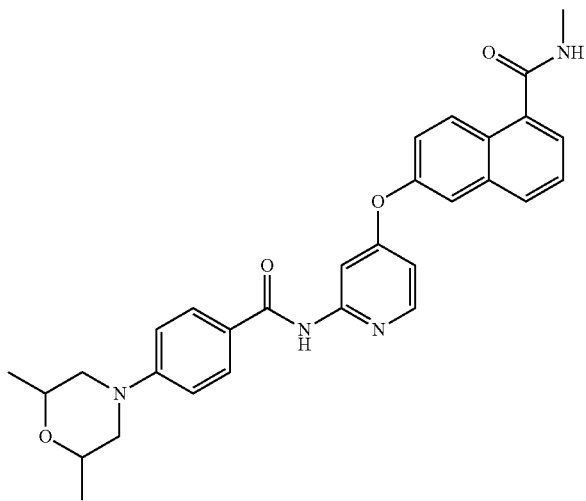 |
| S9 | 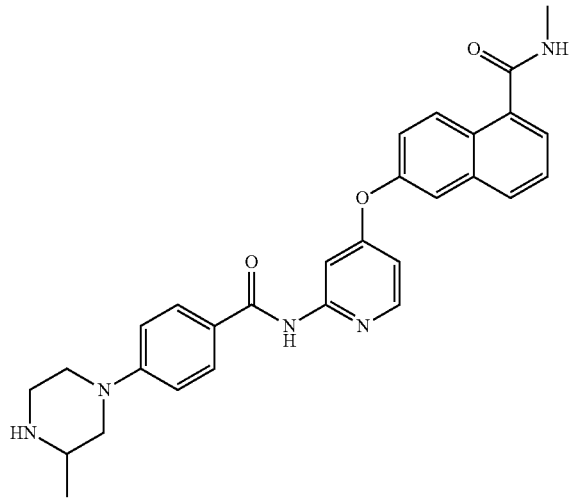 [SMILES: CNC(=O)c1cccc2cc(Oc3ccnc(NC(=O)c4ccc(N5CCNC(C)C5)cc4)c3)ccc12] |

-continued
| Compound | Structure |
|---|---|
| S10 | 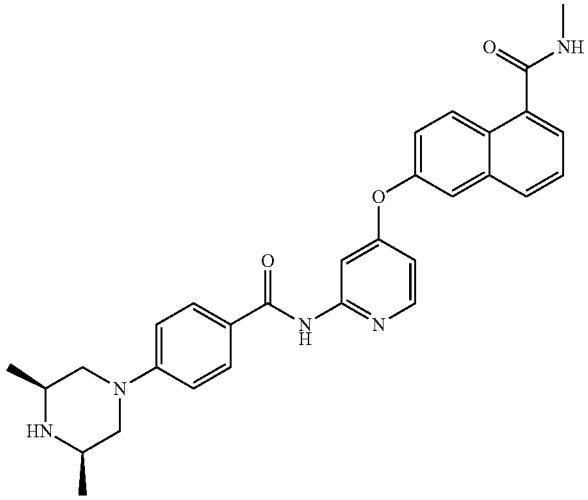 |
| S11 | 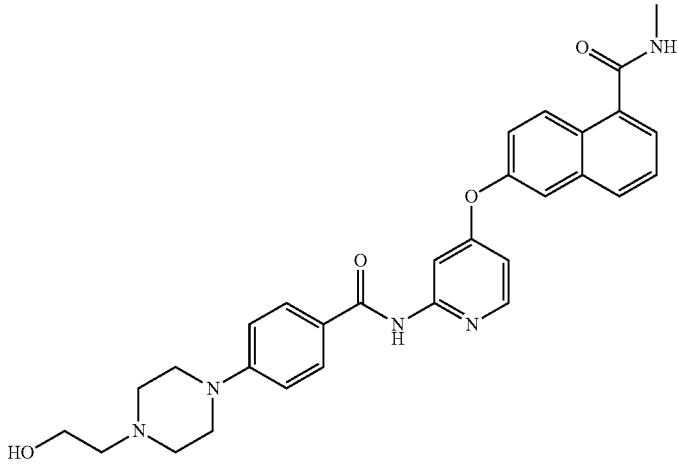 [SMILES: CNC(=O)c1cccc2cc(Oc3ccnc(NC(=O)c4ccc(N5CCN(CCO)CC5)cc4)c3)ccc12] |
| S12 | 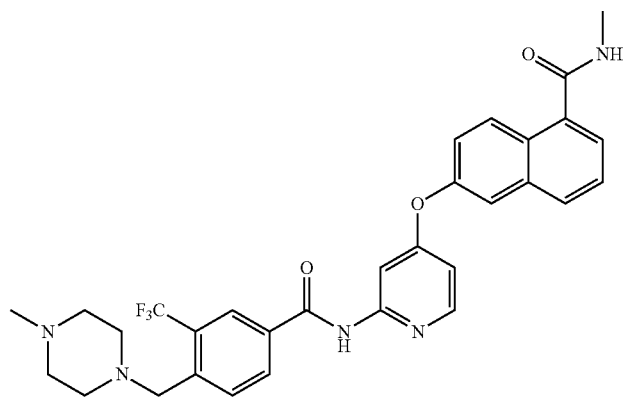 |

-continued
| Compound | Structure |
|---|---|
| S13 | 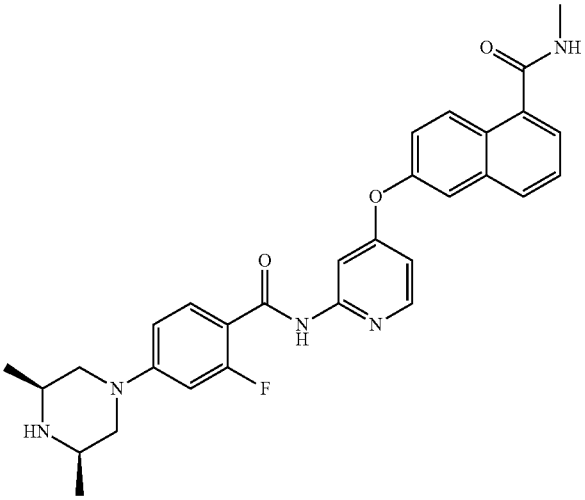 |
| S14 | 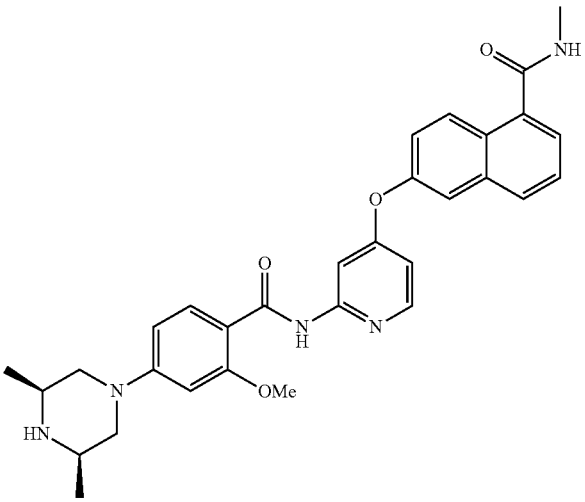 |
| S15 | 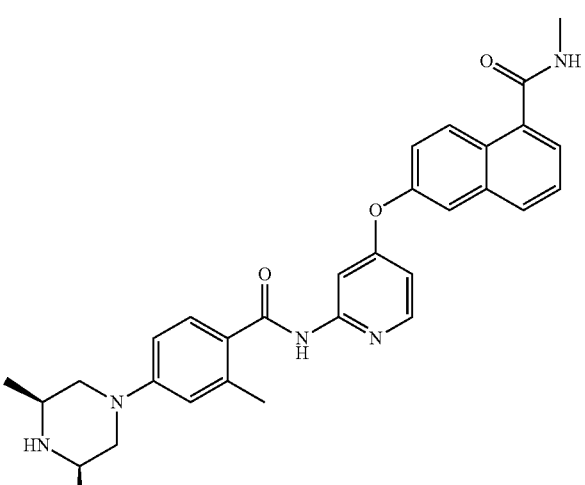 |

-continued
| Compound | Structure |
|---|---|
| S16 | 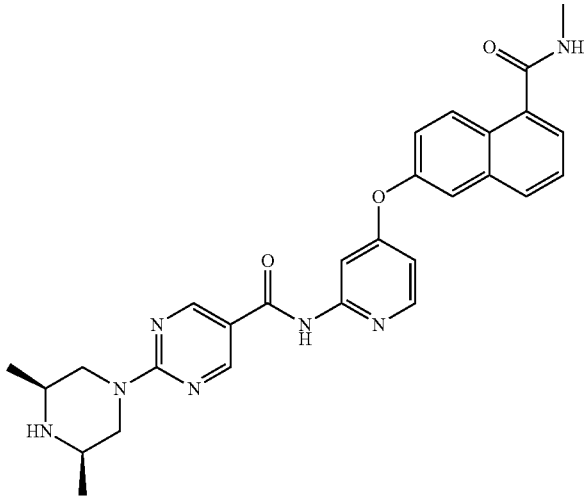 |
| S17 | 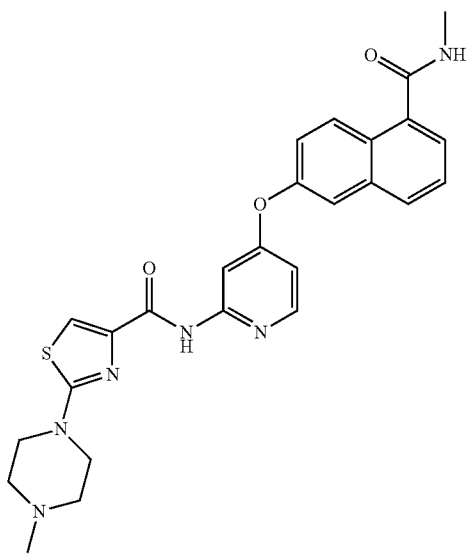 |
| S18 | 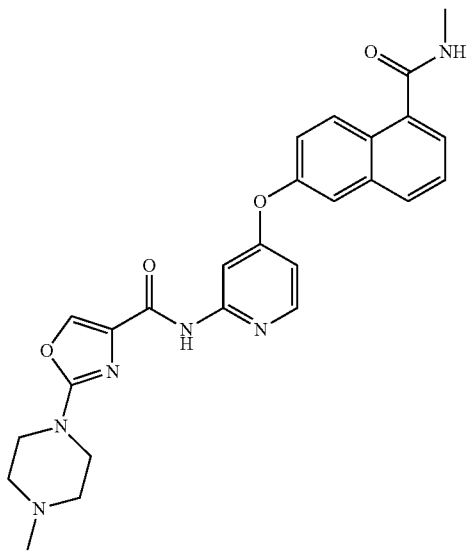 [SMILES: CNC(=O)c1cccc2cc(Oc3ccnc(NC(=O)c4coc(N5CCN(C)CC5)n4)c3)ccc12] |

-continued

| Compound | Structure |
|---|---|
| S19 | 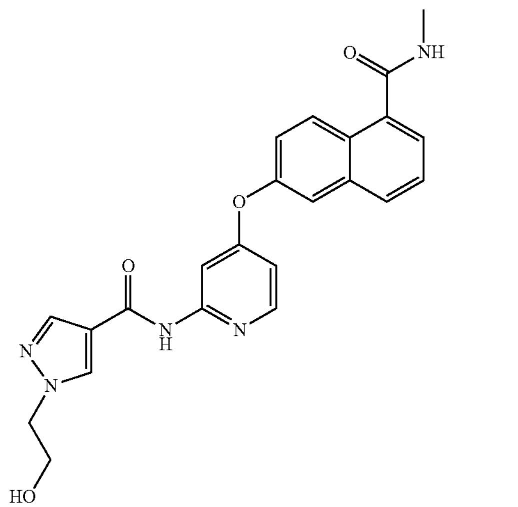 [SMILES: CNC(=O)c1cccc2cc(Oc3ccnc(NC(=O)c4cnn(CCO)c4)c3)ccc12] |
| S20 | 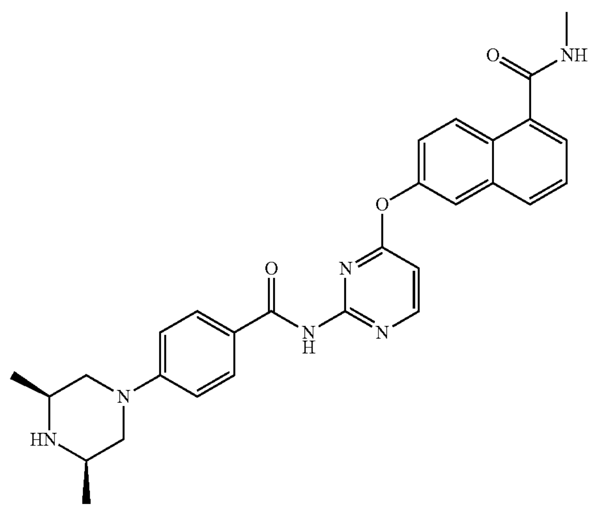 |
| S23 | 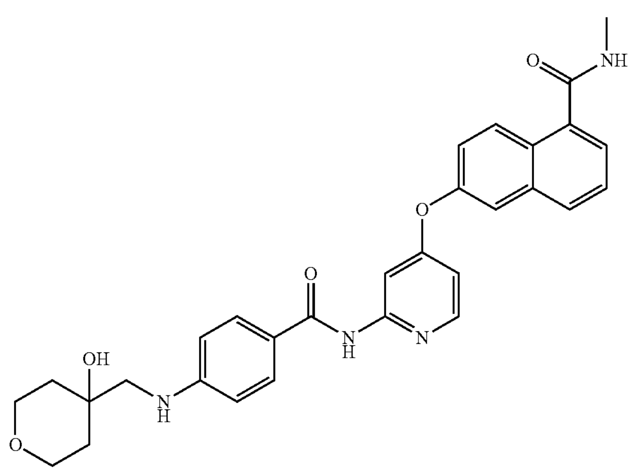 [SMILES: CNC(=O)c1cccc2cc(Oc3ccnc(NC(=O)c4ccc(NCC5(O)CCOCC5)cc4)c3)ccc12] |

| Compound | Structure |
|---|---|
| S24 | 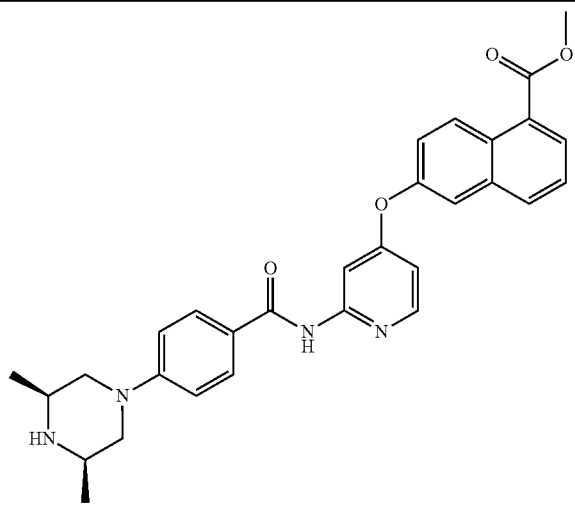 |

9. A preparation method for the compound of claim 1, comprising the following step:

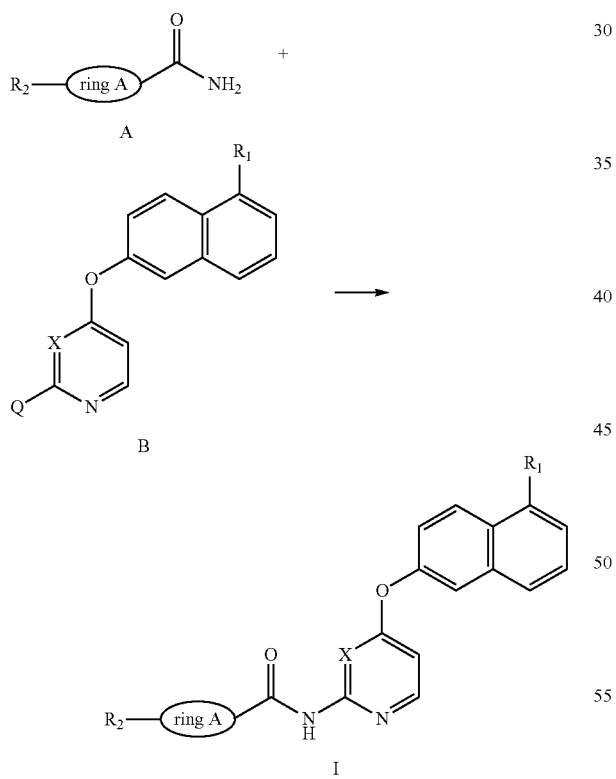

in an inert solvent, reacting formula A compound with formula B compound to obtain formula I compound; wherein Q is a leaving group; ring A, X, $R_1$ and $R_2$ are defined as in claim 1.

10. A pharmaceutical composition, comprising: therapeutically effective amount of the compound of claim 1, or a pharmaceutically acceptable salt thereof, and optionally a pharmaceutically acceptable carrier or excipient.

11. A method for treating cancer or a disease associated with protein tyrosine kinase activity, comprising: administering a therapeutically or prophylactically effective amount of compound according to claim 1, or a pharmaceutically acceptable salt thereof, or a pharmaceutical composition according to the invention to a subject to be treated, wherein the cancer or disease is gastric cancer.

12. A compound of the following formula I, or pharmaceutically acceptable salts thereof:

Formula I

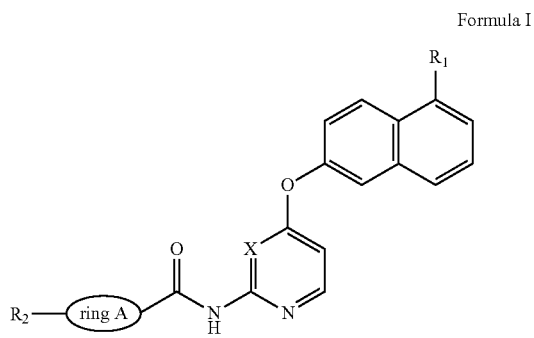

wherein:
X is selected from the group consisting of CH and N;
Ring A may be selected from the group consisting of a substituted or unsubstituted 6-10 membered aryl, substituted or unsubstituted 5-12 membered heteroaryl, wherein "substituted" means that one or more hydrogen atoms on a group are substituted by a substituent selected from the group consisting of a C1-C8 alkyl, C1-C8 alkoxy, C1-C8 alkylamino, halogen, halogenated C1-C8 alkyl;
$R_1$ is selected from —CONHR$_3$, —COOR$_3$;
$R_2$ is selected from the group consisting of a substituted or unsubstituted C1-C8 alkyl, substituted or unsubstituted C1-C8 alkoxy, substituted or unsubstituted 4-10 membered heterocyclic group, substituted or unsubstituted amino, substituted or unsubstituted C1-C8 alkylamino, —NHCOR$_3$; wherein the substituent is further substituted by one or more substituents selected from the group consisting of a C1-C8 alkyl, hydroxy, hydroxy C1-C8 alkyl, —COOR₃, amino-substituted C3-C10 cycloalkyl group, 4-10 membered heterocycloalkyl which is unsubstituted or substituted by one or more halogen atoms, hydroxyl or C1-C8 alkyl;

R₃ is hydrogen or C1-C8 alkyl, or the compound is selected from

S21

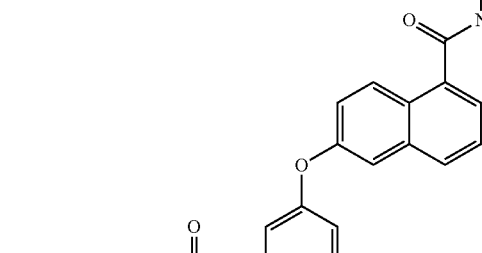

S22

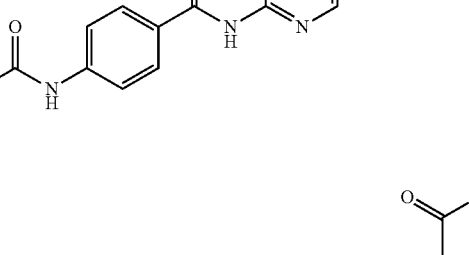

13. The compound of claim 12, wherein, in the formula I compound:

R₂ is selected from the group consisting of a substituted or unsubstituted C1-C4 alkyl, substituted or unsubstituted C1-C4 alkoxy, substituted or unsubstituted 5-6 membered heterocyclic group, substituted or unsubstituted amino, substituted or unsubstituted C1-C4 alkylamino, —NHCOR₃; wherein the substituent group is further substituted by one or more substituents selected from the group consisting of a C1-C8 alkyl, hydroxy, hydroxy C1-C8 alkyl, —COOR₃, amino-substituted C3-C10 cycloalkyl, 4-10 membered heterocycloalkyl which is unsubstituted or substituted by one or more halogen atoms, hydroxyl or C1-C8 alkyl; and ring A is selected from a substituted or unsubstituted 6-10 membered aryl or substituted or unsubstituted 5-6 membered heteroaryl.

14. The compound of claim 13, wherein, in the formula I compound, ring A is a substituted or unsubstituted group selected from the group consisting of benzene ring, naphthalene ring, pyridine ring, pyrazine ring, thiophene ring, furan ring, imidazole ring, pyrrole ring, oxazole ring, thiazole ring, pyrazole ring, indole ring, pyrimidine ring, benzofuran ring, benzo thiazole ring, benzimidazole ring, quinoline ring, isoquinoline ring.

15. The compound of claim 14, wherein R₃ is hydrogen or C1-C4 alkyl.

16. The compound of claim 15, wherein the compound is selected from the following group:

| Compound | Structure |
| --- | --- |
| S1 | 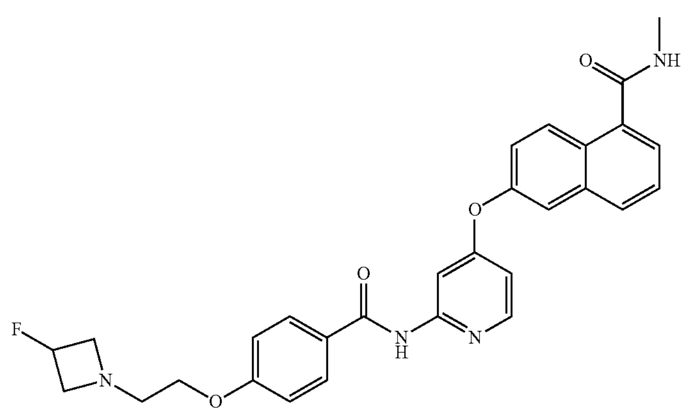 [SMILES: CNC(=O)c1cccc2cc(Oc3ccnc(NC(=O)c4ccc(OCCN5CC(F)C5)cc4)c3)ccc12] |

-continued

| Compound | Structure |
|---|---|
| S2 | 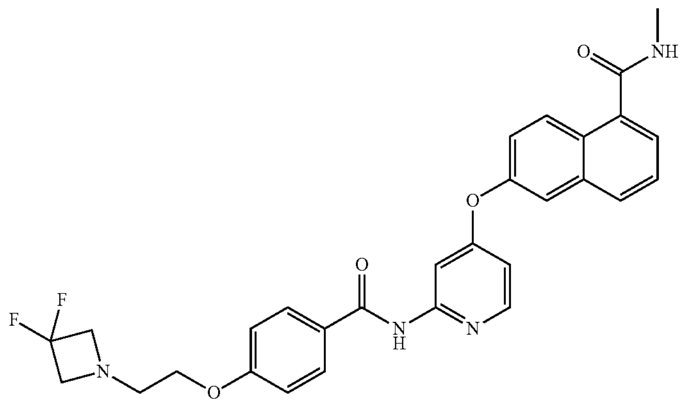 [SMILES: CNC(=O)c1cccc2cc(Oc3ccnc(NC(=O)c4ccc(OCCN5CC(F)(F)C5)cc4)c3)ccc12] |
| S3 | 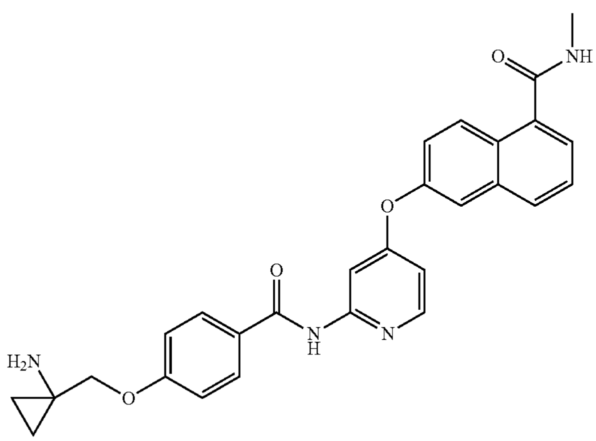 [SMILES: CNC(=O)c1cccc2cc(Oc3ccnc(NC(=O)c4ccc(OCC5(N)CC5)cc4)c3)ccc12] |
| S4 | 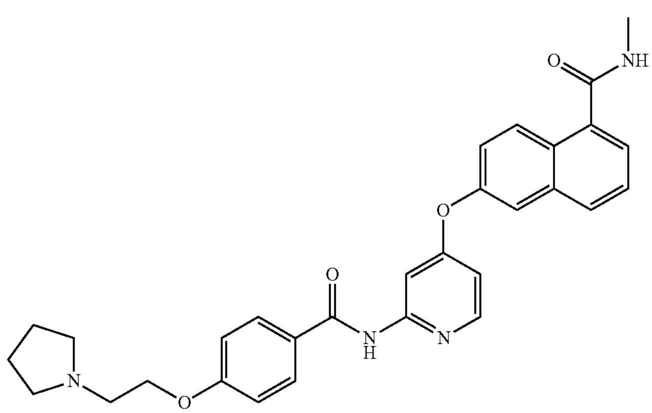 [SMILES: CNC(=O)c1cccc2cc(Oc3ccnc(NC(=O)c4ccc(OCCN5CCCC5)cc4)c3)ccc12] |

-continued
| Compound | Structure |
|---|---|
| S5 | 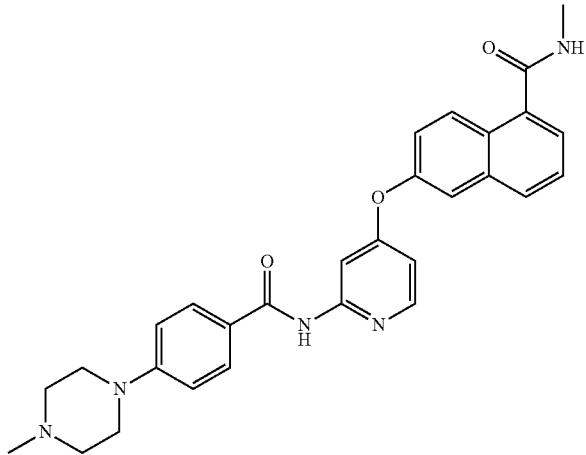 |
| S6 | 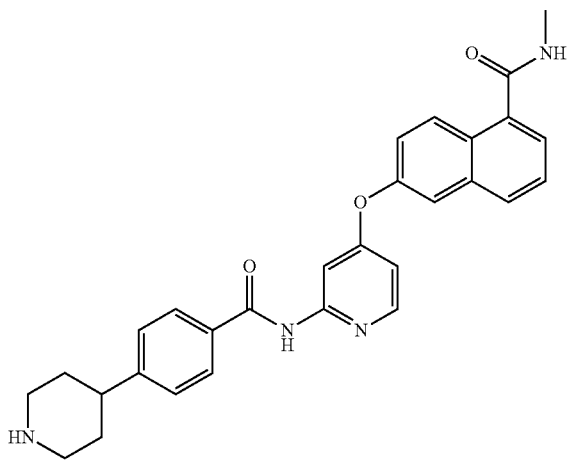 [SMILES: CNC(=O)c1cccc2cc(Oc3ccnc(NC(=O)c4ccc(C5CCNCC5)cc4)c3)ccc12] |
| S7 | 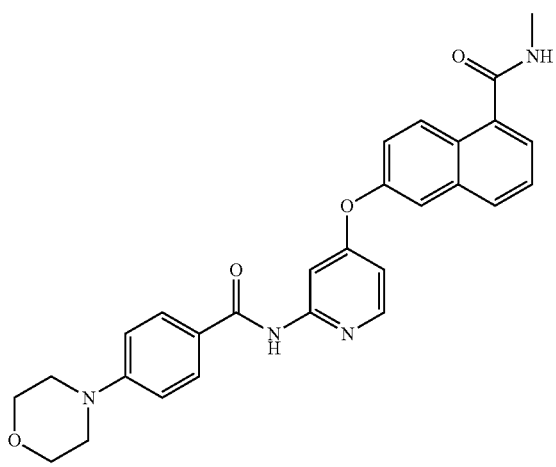 [SMILES: CNC(=O)c1cccc2cc(Oc3ccnc(NC(=O)c4ccc(N5CCOCC5)cc4)c3)ccc12] |

| Compound | Structure |
|---|---|
| S8 | 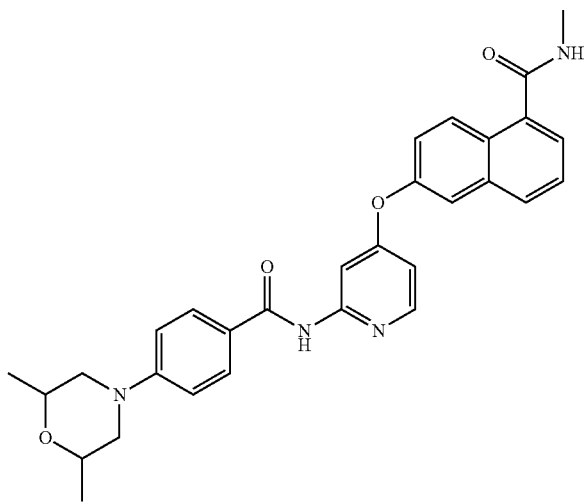 |
| S9 | 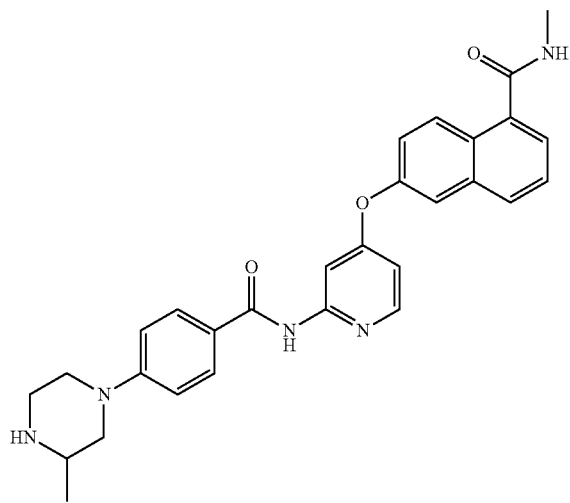 [SMILES: CNC(=O)c1cccc2cc(Oc3ccnc(NC(=O)c4ccc(N5CCNC(C)C5)cc4)c3)ccc12] |
| S10 | 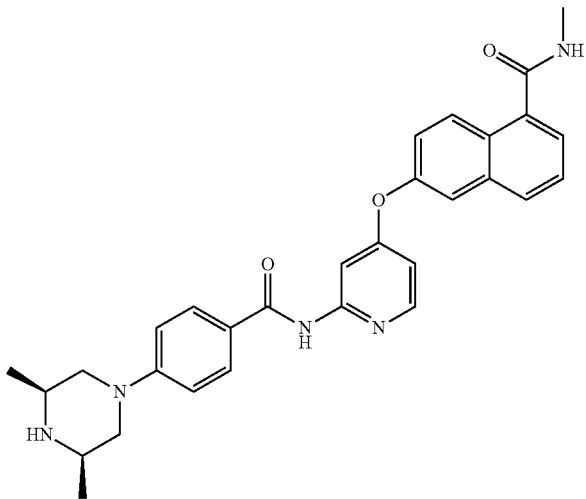 |

| Compound | Structure |
|---|---|
| S11 | 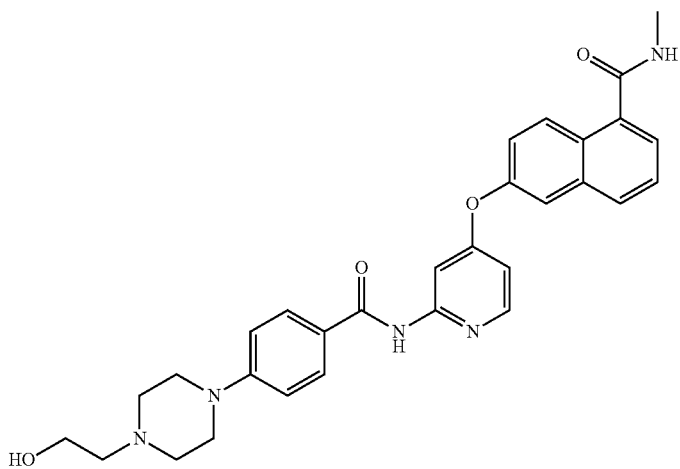 [SMILES: CNC(=O)c1cccc2cc(Oc3ccnc(NC(=O)c4ccc(N5CCN(CCO)CC5)cc4)c3)ccc12] |
| S12 | 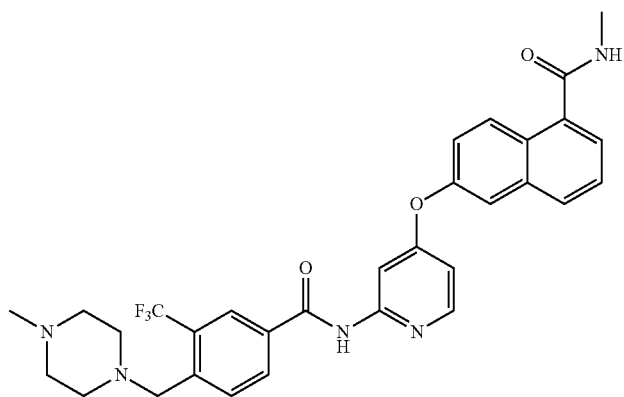 |
| S13 | 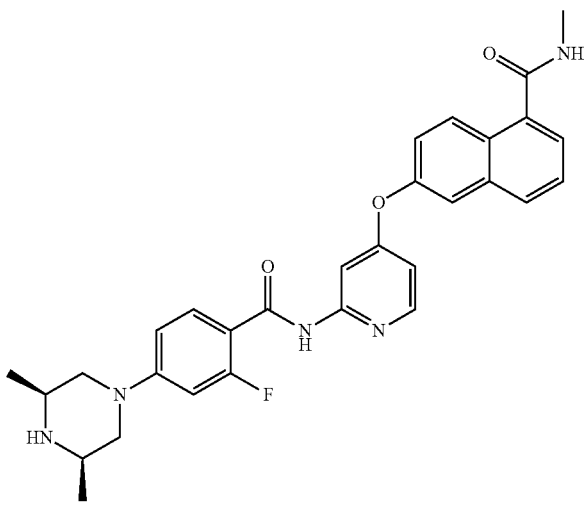 |

| Compound | Structure |
|---|---|
| S14 | 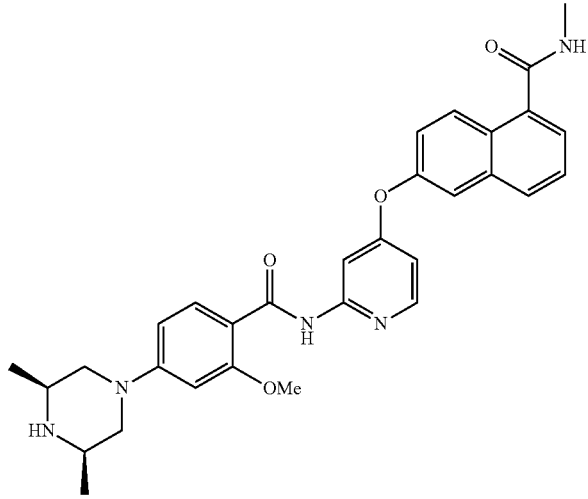 |
| S15 | 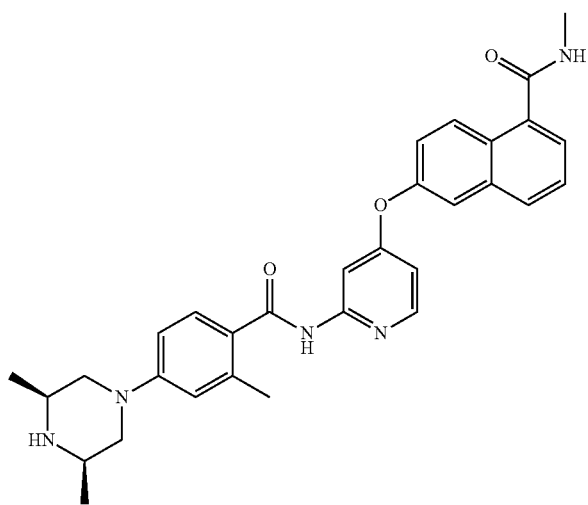 |
| S16 | 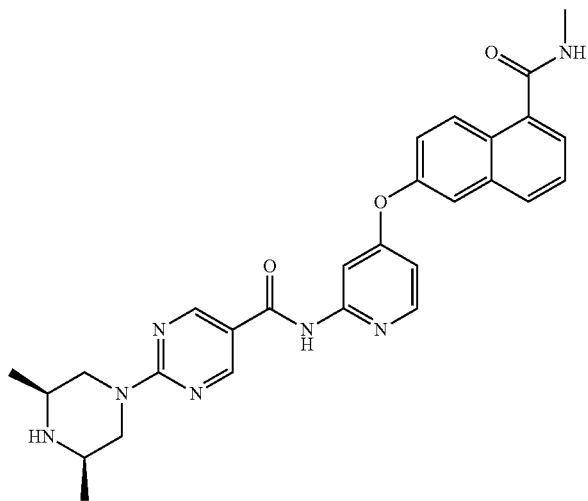 |

-continued
| Compound | Structure |
|---|---|
| S17 | 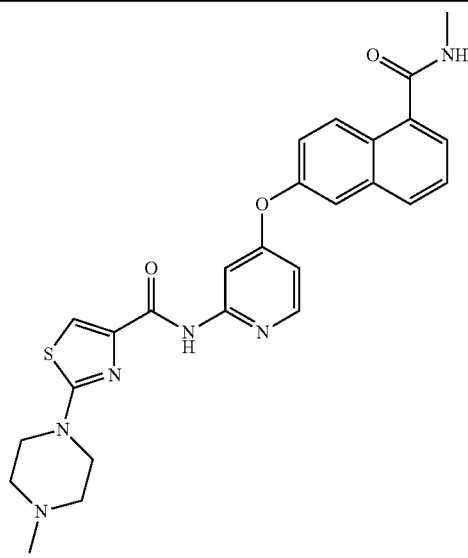 |
| S18 | 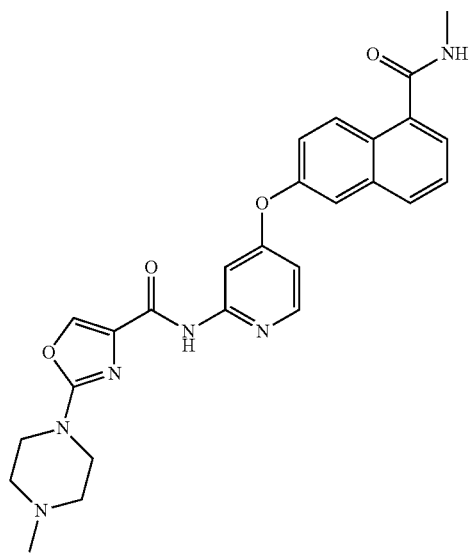 [SMILES: CNC(=O)c1cccc2cc(Oc3ccnc(NC(=O)c4coc(N5CCN(C)CC5)n4)c3)ccc12] |
| S19 | 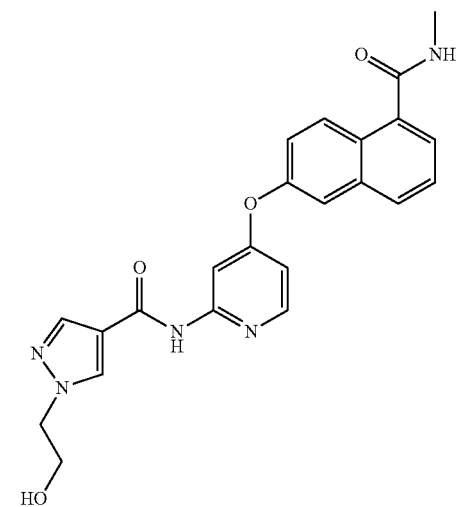 [SMILES: CNC(=O)c1cccc2cc(Oc3ccnc(NC(=O)c4cnn(CCO)c4)c3)ccc12] |

-continued
| Compound | Structure |
|---|---|
| S20 | 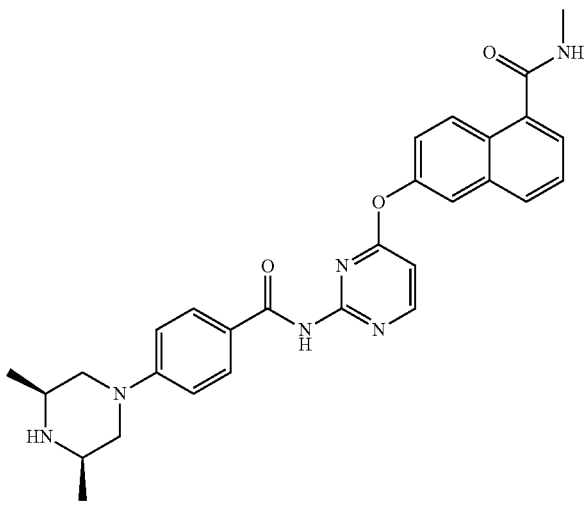 |
| S23 | 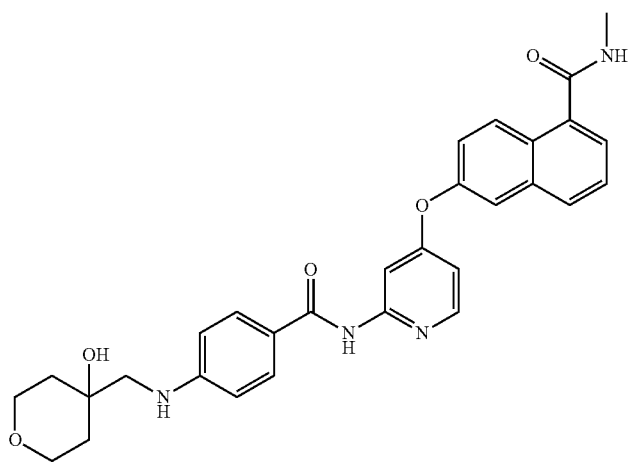 [SMILES: CNC(=O)c1cccc2cc(Oc3ccnc(NC(=O)c4ccc(NCC5(O)CCOCC5)cc4)c3)ccc12] |
| S24 | 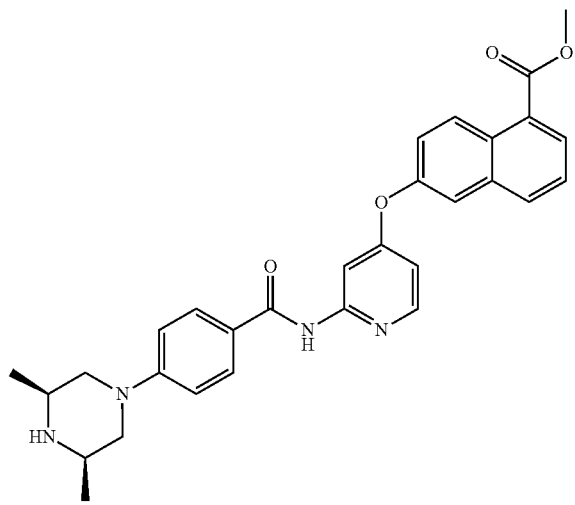 |
* * * * *

UNITED STATES PATENT AND TRADEMARK OFFICE
CERTIFICATE OF CORRECTION

| | | |
|---|---|---|
| PATENT NO. | : 11,834,432 B2 | Page 1 of 1 |
| APPLICATION NO. | : 15/998927 | |
| DATED | : December 5, 2023 | |
| INVENTOR(S) | : Zhang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this
Twelfth Day of November, 2024

*Katherine Kelly Vidal*

Katherine Kelly Vidal
*Director of the United States Patent and Trademark Office*